US009855442B2

(12) United States Patent
Deisseroth et al.

(10) Patent No.: US 9,855,442 B2
(45) Date of Patent: *Jan. 2, 2018

(54) METHOD FOR OPTICALLY CONTROLLING A NEURON WITH A MAMMALIAN CODON OPTIMIZED NUCLEOTIDE SEQUENCE THAT ENCODES A VARIANT OPSIN POLYPEPTIDE DERIVED FROM NATROMONAS PHARAONIS (NPHR)

(71) Applicant: The Board of Trustees of the Leland Stanford Junior University, Stanford, CA (US)

(72) Inventors: Karl Deisseroth, Stanford, CA (US); Feng Zhang, Cambridge, MA (US); Viviana Gradinaru, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/063,296

(22) Filed: Mar. 7, 2016

(65) Prior Publication Data

US 2016/0175607 A1 Jun. 23, 2016

Related U.S. Application Data

(63) Continuation of application No. 13/855,413, filed on Apr. 2, 2013, now Pat. No. 9,284,353, which is a (Continued)

(51) Int. Cl.

| | |
|---|---|
| ***C12N 13/00*** | (2006.01) |
| ***A61N 5/06*** | (2006.01) |
| ***A01K 67/033*** | (2006.01) |
| ***A61K 48/00*** | (2006.01) |
| ***C07K 14/195*** | (2006.01) |
| ***C07K 14/215*** | (2006.01) |
| ***C12N 15/86*** | (2006.01) |
| ***C07K 14/00*** | (2006.01) |
| *A61K 38/00* | (2006.01) |

(52) U.S. Cl.

CPC .......... *A61N 5/062* (2013.01); *A01K 67/0333* (2013.01); *A61K 48/005* (2013.01); *A61K 48/0058* (2013.01); *A61K 48/0083* (2013.01); *A61N 5/0613* (2013.01); *A61N 5/0622* (2013.01); *C07K 14/00* (2013.01); *C07K 14/195* (2013.01); *C07K 14/215* (2013.01); *C12N 13/00* (2013.01); *C12N 15/86* (2013.01); *A01K 2217/052* (2013.01); *A01K 2227/703* (2013.01); *A01K 2267/0356* (2013.01); *A61K 38/00* (2013.01); *C12N 2710/10343* (2013.01); *C12N 2710/16643* (2013.01); *C12N 2740/16043* (2013.01); *C12N 2740/16071* (2013.01); *C12N 2750/14143* (2013.01); *C12N 2830/002* (2013.01)

(58) Field of Classification Search

CPC .... C07K 14/00; C07K 14/195; C07K 14/215; A61N 5/062; A61N 5/0613; A61N 5/0622; C12N 13/00; C12N 15/86; C12N 2710/10343; C12N 2740/16071; C12N 2830/002; C12N 2740/16043; C12N 2750/14143; C12N 2710/16643; A61K 48/0058; A61K 48/0083; A61K 48/005; A61K 38/00; A01K 67/0333; A01K 2267/0356; A01K 2217/052; A01K 2227/703

See application file for complete search history.

(56) References Cited

U.S. PATENT DOCUMENTS 2,968,302 A 1/1961 Fry et al.
3,131,690 A 5/1964 Innis et al.
(Continued)

FOREIGN PATENT DOCUMENTS

CN 1079464 A 12/1993
CN 102076866 A 5/2011
(Continued)

OTHER PUBLICATIONS

Jones, et al.; "Animal Models of Schizophrenia"; British Journal of Pharmacology; vol. 164, pp. 1162-1194 (2011).
Chow, et al.; "High-performance genetically targetable optical neural silencing by light-driven proton pumps"; Nature; vol. 463, pp. 98-102 (Jan. 7, 2010).
Gong, et al.; "Enhanced Archaerhodopsin Fluorescent Protein Voltage Indicators"; PLOS One; vol. 8, Issue 6, 10 pages (Jun. 2013).
Han, et al.; "A high-light sensitivity optical neural silencer: development and application to optogenetic control of non-human primate cortex"; Frontiers in Systems Neuroscience; vol. 5, Article 18, pp. 1-8 (Apr. 2011).
(Continued)

*Primary Examiner* — Titilayo Moloye
(74) *Attorney, Agent, or Firm* — Bozicevic, Field & Francis LLP; Paula A. Borden

(57) ABSTRACT

Stimulation of target cells using light, e.g., in vivo or in vitro, is implemented using a variety of methods and devices. One example involves a vector for delivering a light-activated NpHR-based molecule comprising a nucleic acid sequence that codes for light-activated NpHR-based molecule and a promoter. Either a high expression of the molecule manifests a toxicity level that is less than about 75%, or the light-activated NpHR-based proteins are expressed using at least two NpHR-based molecular variants. Each of the variants characterized in being useful for expressing a light-activated NpHR-based molecule that responds to light by producing an inhibitory current to dissuade depolarization of the neuron. Other aspects and embodiments are directed to systems, methods, kits, compositions of matter and molecules for ion pumps or for controlling inhibitory currents in a cell (e.g., in in vivo and in vitro environments).

15 Claims, 20 Drawing Sheets

Related U.S. Application Data continuation of application No. 13/208,419, filed on Aug. 12, 2011, now Pat. No. 9,757,587, which is a continuation of application No. 12/041,628, filed on Mar. 3, 2008, now abandoned.

(60) Provisional application No. 60/904,303, filed on Mar. 1, 2007.

(56) References Cited

U.S. PATENT DOCUMENTS 3,499,437 A 3/1970 Balamuth et al.
3,567,847 A 3/1971 Price
4,343,301 A 8/1982 Indech
4,559,951 A 12/1985 Dahl et al.
4,616,231 A 10/1986 Autrey et al.
4,865,042 A 9/1989 Umemura et al.
4,879,284 A 11/1989 Lang et al.
5,032,123 A 7/1991 Katz et al.
5,041,224 A 8/1991 Ohyama et al.
5,082,670 A 1/1992 Gage et al.
5,249,575 A 10/1993 Di Mino et al.
5,267,152 A 11/1993 Yang et al.
5,290,280 A 3/1994 Daikuzono et al.
5,330,515 A 7/1994 Rutecki et al.
5,382,516 A 1/1995 Bush
5,411,540 A 5/1995 Edell et al.
5,445,608 A 8/1995 Chen et al.
5,460,950 A 10/1995 Barr et al.
5,460,954 A 10/1995 Lee et al.
5,470,307 A 11/1995 Lindall
5,495,541 A 2/1996 Murray et al.
5,520,188 A 5/1996 Hennige et al.
5,527,695 A 6/1996 Hodges et al.
5,550,316 A 8/1996 Mintz
5,641,650 A 6/1997 Turner et al.
5,703,985 A 12/1997 Owyang et al.
5,722,426 A 3/1998 Kolff
5,738,625 A 4/1998 Gluck
5,739,273 A 4/1998 Engelman et al.
5,741,316 A 4/1998 Chen et al.
5,755,750 A 5/1998 Petruska et al.
5,756,351 A 5/1998 Isacoff et al.
5,782,896 A 7/1998 Chen et al.
5,795,581 A 8/1998 Segalman et al.
5,807,285 A 9/1998 Vaitekunas et al.
5,816,256 A 10/1998 Kissinger et al.
5,836,941 A 11/1998 Yoshihara et al.
5,898,058 A 4/1999 Nichols
5,939,320 A 8/1999 Littman et al.
6,056,738 A 5/2000 Marchitto et al.
6,057,114 A 5/2000 Akong
6,108,081 A 8/2000 Holtom et al.
6,134,474 A 10/2000 Fischell et al.
6,161,045 A 12/2000 Fischell et al.
6,180,613 B1 1/2001 Kaplitt et al.
6,253,109 B1 6/2001 Gielen
6,303,362 B1 10/2001 Kay et al.
6,334,846 B1 1/2002 Ishibashi et al.
6,336,904 B1 1/2002 Nikolchev
6,346,101 B1 2/2002 Alfano et al.
6,364,831 B1 4/2002 Crowley
6,377,842 B1 4/2002 Pogue et al.
6,436,708 B1 8/2002 Leone et al.
6,473,639 B1 10/2002 Fischell et al.
6,480,743 B1 11/2002 Kirkpatrick et al.
6,489,115 B2 12/2002 Lahue et al.
6,497,872 B1 12/2002 Weiss et al.
6,506,154 B1 1/2003 Ezion et al.
6,536,440 B1 3/2003 Dawson
6,551,346 B2 4/2003 Crossley
6,567,690 B2 5/2003 Giller et al.
6,597,954 B1 7/2003 Pless et al.
6,609,020 B2 8/2003 Gill
6,615,080 B1 9/2003 Unsworth et al.
6,631,283 B2 10/2003 Storrie et al.
6,632,672 B2 10/2003 Calos
6,647,296 B2 11/2003 Fischell et al.
6,685,656 B1 2/2004 Duarte et al.
6,686,193 B2 2/2004 Maher et al.
6,721,603 B2 4/2004 Zabara et al.
6,729,337 B2 5/2004 Dawson
6,780,490 B1 8/2004 Tanaka et al.
6,790,652 B1 9/2004 Terry et al.
6,790,657 B1 9/2004 Arya
6,805,129 B1 10/2004 Pless et al.
6,808,873 B2 10/2004 Murphy et al.
6,810,285 B2 10/2004 Pless et al.
6,889,085 B2 5/2005 Dawson
6,921,413 B2 7/2005 Mahadevan-Jansen et al.
6,969,449 B2 11/2005 Maher et al.
6,974,448 B2 12/2005 Petersen
7,045,344 B2 5/2006 Kay et al.
7,091,500 B2 8/2006 Schnitzer
7,144,733 B2 12/2006 Miesenbock et al.
7,175,596 B2 2/2007 Vitek et al.
7,191,018 B2 3/2007 Gielen et al.
7,211,054 B1 5/2007 Francis et al.
7,220,240 B2 5/2007 Struys et al.
7,298,143 B2 11/2007 Jaermann et al.
7,313,442 B2 12/2007 Velasco et al.
7,603,174 B2 10/2009 De Ridder
7,610,100 B2 10/2009 Jaax et al.
7,613,520 B2 11/2009 De Ridder
7,686,839 B2 3/2010 Parker
7,824,869 B2 11/2010 Hegemann et al.
7,883,536 B1 2/2011 Bendett
7,988,688 B2 8/2011 Webb et al.
8,386,312 B2 2/2013 Pradeep et al.
8,398,692 B2 3/2013 Deisseroth et al.
8,401,609 B2 3/2013 Deisseroth et al.
8,603,790 B2 12/2013 Deisseroth et al.
8,696,722 B2 4/2014 Deisseroth et al.
8,716,447 B2 5/2014 Deisseroth et al.
8,729,040 B2 5/2014 Deisseroth et al.
8,815,582 B2 8/2014 Deisseroth et al.
8,834,546 B2 9/2014 Deisseroth et al.
8,864,805 B2 10/2014 Deisseroth et al.
8,906,360 B2 12/2014 Deisseroth et al.
8,926,959 B2 1/2015 Deisseroth et al.
8,932,562 B2 1/2015 Deisseroth et al.
8,956,363 B2 2/2015 Deisseroth et al.
8,962,589 B2 2/2015 Deisseroth et al.
9,057,734 B2 6/2015 Cohen
9,079,940 B2 7/2015 Deisseroth et al.
9,084,885 B2 7/2015 Deisseroth et al.
9,101,690 B2 8/2015 Deisseroth et al.
9,101,759 B2 8/2015 Deisseroth et al.
9,175,095 B2 11/2015 Deisseroth et al.
9,187,745 B2 11/2015 Deisseroth et al.
9,238,150 B2 1/2016 Deisseroth et al.
9,249,200 B2 2/2016 Deisseroth et al.
9,249,234 B2 2/2016 Deisseroth et al.
9,271,674 B2 3/2016 Deisseroth et al.
9,274,099 B2 3/2016 Deisseroth et al.
9,278,159 B2 3/2016 Deisseroth et al.
9,284,353 B2 3/2016 Deisseroth et al.
9,359,449 B2 6/2016 Deisseroth et al.
9,458,208 B2 10/2016 Deisseroth et al.
9,522,288 B2 12/2016 Deisseroth et al.
9,604,073 B2 3/2017 Deisseroth et al.
2001/0023346 A1 9/2001 Loeb
2002/0094516 A1 7/2002 Calos et al.
2002/0155173 A1 10/2002 Chopp et al.
2002/0164577 A1 11/2002 Tsien et al.
2002/0190922 A1 12/2002 Tsao
2002/0193327 A1 12/2002 Nemerow et al.
2003/0009103 A1 1/2003 Yuste et al.
2003/0026784 A1 2/2003 Koch et al.
2003/0040080 A1 2/2003 Miesenbock et al.
2003/0050258 A1 3/2003 Calos
2003/0082809 A1 5/2003 Quail et al.
2003/0088060 A1 5/2003 Benjamin et al.
2003/0097122 A1 5/2003 Ganz et al.

(56) References Cited

U.S. PATENT DOCUMENTS

2003/0104512 A1 6/2003 Freeman et al.
2003/0125719 A1 7/2003 Furnish
2003/0144650 A1 7/2003 Smith
2003/0204135 A1 10/2003 Bystritsky
2003/0232339 A1 12/2003 Shu et al.
2004/0013645 A1 1/2004 Monahan et al.
2004/0015211 A1 1/2004 Nurmikko et al.
2004/0023203 A1 2/2004 Miesenbock et al.
2004/0034882 A1 2/2004 Vale et al.
2004/0039312 A1 2/2004 Hillstead et al.
2004/0049134 A1 3/2004 Tosaya et al.
2004/0068202 A1 4/2004 Hansson et al.
2004/0073278 A1 4/2004 Pachys
2004/0076613 A1 4/2004 Mazarkis et al.
2004/0122475 A1 6/2004 Myrick et al.
2004/0203152 A1 10/2004 Calos
2004/0216177 A1 10/2004 Jordan et al.
2004/0267118 A1 12/2004 Dawson
2005/0058987 A1 3/2005 Shi et al.
2005/0088177 A1 4/2005 Schreck et al.
2005/0107753 A1 5/2005 Rezai et al.
2005/0112759 A1 5/2005 Radisic et al.
2005/0119315 A1 6/2005 Fedida et al.
2005/0124897 A1 6/2005 Chopra
2005/0143295 A1 6/2005 Walker et al.
2005/0143790 A1 6/2005 Kipke et al.
2005/0153885 A1 7/2005 Yun et al.
2005/0197679 A1 9/2005 Dawson
2005/0202398 A1 9/2005 Hegemann et al.
2005/0215764 A1 9/2005 Tuszynski et al.
2005/0240127 A1 10/2005 Seip et al.
2005/0267011 A1 12/2005 Deisseroth et al.
2005/0267454 A1 12/2005 Hissong et al.
2005/0279354 A1 12/2005 Deutsch et al.
2006/0025756 A1 2/2006 Francischelli et al.
2006/0034943 A1 2/2006 Tuszynski
2006/0057192 A1 3/2006 Kane
2006/0057614 A1 3/2006 Heintz
2006/0058671 A1 3/2006 Vitek et al.
2006/0058678 A1 3/2006 Vitek et al.
2006/0100679 A1 5/2006 DiMauro et al.
2006/0106543 A1 5/2006 Deco et al.
2006/0155348 A1 7/2006 de Charms
2006/0161227 A1 7/2006 Walsh et al.
2006/0167500 A1 7/2006 Towe et al.
2006/0179501 A1 8/2006 Chan et al.
2006/0184069 A1 8/2006 Vaitekunas
2006/0190044 A1 8/2006 Libbus et al.
2006/0206172 A1 9/2006 DiMauro et al.
2006/0216689 A1 9/2006 Maher et al.
2006/0236525 A1 10/2006 Sliwa et al.
2006/0241697 A1 10/2006 Libbus et al.
2006/0253177 A1 11/2006 Taboada et al.
2006/0271024 A1 11/2006 Gertner et al.
2007/0027443 A1 2/2007 Rose et al.
2007/0031924 A1 2/2007 Li et al.
2007/0053996 A1 3/2007 Boyden et al.
2007/0054319 A1 3/2007 Boyden et al.
2007/0060915 A1 3/2007 Kucklick
2007/0060984 A1 3/2007 Webb et al.
2007/0135875 A1 6/2007 Demarais et al.
2007/0156180 A1 7/2007 Jaax et al.
2007/0191906 A1 8/2007 Lyer et al.
2007/0196838 A1 8/2007 Chesnut et al.
2007/0197918 A1 8/2007 Vitek et al.
2007/0219600 A1 9/2007 Gertner et al.
2007/0220628 A1 9/2007 Glassman et al.
2007/0239080 A1 10/2007 Schaden et al.
2007/0239210 A1 10/2007 Libbus et al.
2007/0253995 A1 11/2007 Hildebrand
2007/0260295 A1 11/2007 Chen et al.
2007/0261127 A1 11/2007 Boyden et al.
2007/0282404 A1 12/2007 Cottrell et al.
2007/0295978 A1 12/2007 Coushaine et al.
2008/0020465 A1 1/2008 Padidam
2008/0027505 A1 1/2008 Levin et al.
2008/0046053 A1 1/2008 Wagner et al.
2008/0033569 A1 2/2008 Ferren et al.
2008/0050770 A1 2/2008 Zhang et al.
2008/0051673 A1 2/2008 Kong et al.
2008/0060088 A1 3/2008 Shin et al.
2008/0065158 A1 3/2008 Ben-Ezra et al.
2008/0065183 A1 3/2008 Whitehurst et al.
2008/0077200 A1 3/2008 Bendett et al.
2008/0085265 A1 4/2008 Schneider et al.
2008/0088258 A1 4/2008 Ng
2008/0103551 A1 5/2008 Masoud et al.
2008/0119421 A1 5/2008 Tuszynski et al.
2008/0125836 A1 5/2008 Streeter et al.
2008/0167261 A1 7/2008 Sclimenti
2008/0175819 A1 7/2008 Kingsman et al.
2008/0176076 A1 7/2008 Van Veggel et al.
2008/0200749 A1 8/2008 Zheng et al.
2008/0221452 A1 9/2008 Njemanze
2008/0227139 A1 9/2008 Deisseroth et al.
2008/0228244 A1 9/2008 Pakhomov et al.
2008/0262411 A1 10/2008 Dobak
2008/0287821 A1 11/2008 Jung et al.
2008/0290318 A1 11/2008 Van Veggel et al.
2009/0030930 A1 1/2009 Pradeep et al.
2009/0054954 A1 2/2009 Foley et al.
2009/0069261 A1 3/2009 Dodge et al.
2009/0088680 A1 4/2009 Deisseroth et al.
2009/0093403 A1 4/2009 Zhang et al.
2009/0099038 A1 4/2009 Deisseroth et al.
2009/0112133 A1 4/2009 Deisseroth et al.
2009/0118800 A1 5/2009 Deisseroth et al.
2009/0131837 A1 5/2009 Granville
2009/0148861 A1 6/2009 Pegan et al.
2009/0157145 A1 6/2009 Cauller
2009/0254134 A1 10/2009 Nikolov et al.
2009/0268511 A1 10/2009 Birge et al.
2009/0319008 A1 12/2009 Mayer
2009/0326603 A1 12/2009 Boggs et al.
2010/0009444 A1 1/2010 Herlitze et al.
2010/0016783 A1 1/2010 Bourke et al.
2010/0021982 A1 1/2010 Herlitze
2010/0145418 A1 6/2010 Zhang et al.
2010/0146645 A1 6/2010 Vasar et al.
2010/0190229 A1 7/2010 Zhang et al.
2010/0234273 A1 9/2010 Deisseroth et al.
2011/0221970 A1 1/2011 Vo-Dihn et al.
2011/0092800 A1 4/2011 Yoo et al.
2011/0105998 A1 5/2011 Deisseroth et al.
2011/0112463 A1 5/2011 Silver et al.
2011/0125077 A1 5/2011 Denison et al.
2011/0125078 A1 5/2011 Denison et al.
2011/0159562 A1 6/2011 Deisseroth et al.
2011/0165681 A1 7/2011 Boyden et al.
2011/0166632 A1 7/2011 Delp et al.
2011/0233046 A1 9/2011 Nikolenko et al.
2011/0301529 A1 12/2011 Zhang et al.
2011/0311489 A1 12/2011 Deisseroth et al.
2012/0093772 A1 4/2012 Horsager et al.
2012/0121542 A1 5/2012 Chuong et al.
2012/0253261 A1 10/2012 Poletto et al.
2013/0030275 A1 1/2013 Seymour et al.
2013/0089503 A1 4/2013 Deisseroth et al.
2013/0144359 A1 6/2013 Kishawi et al.
2013/0284920 A1 10/2013 Deisseroth et al.
2013/0286181 A1 10/2013 Betzig et al.
2013/0288365 A1 10/2013 Deisseroth et al.
2013/0289669 A1 10/2013 Deisseroth et al.
2013/0289675 A1 10/2013 Deisseroth et al.
2013/0296406 A1 11/2013 Deisseroth et al.
2013/0317569 A1 11/2013 Deisseroth et al.
2013/0317575 A1 11/2013 Deisseroth et al.
2013/0330816 A1 12/2013 Deisseroth et al.
2013/0343998 A1 12/2013 Deisseroth et al.
2013/0347137 A1 12/2013 Deisseroth et al.
2014/0082758 A1 3/2014 Deisseroth et al.
2014/0148880 A1 5/2014 Deisseroth et al.
2014/0235826 A1 8/2014 Deisseroth et al.
2014/0271479 A1 9/2014 Lammel et al.

(56) References Cited

U.S. PATENT DOCUMENTS

| | | | |
|---|---|---|---|
| 2014/0324133 | A1 | 10/2014 | Deisseroth et al. |
| 2015/0040249 | A1 | 2/2015 | Deisseroth et al. |
| 2015/0072394 | A1 | 3/2015 | Deisseroth et al. |
| 2015/0112411 | A1 | 4/2015 | Beckman et al. |
| 2015/0165227 | A1 | 6/2015 | Deisseroth et al. |
| 2015/0174244 | A1 | 6/2015 | Deisseroth et al. |
| 2015/0217128 | A1 | 8/2015 | Deisseroth et al. |
| 2015/0218547 | A1 | 8/2015 | Deisseroth et al. |
| 2015/0297719 | A1 | 10/2015 | Deisseroth et al. |
| 2016/0002302 | A1 | 1/2016 | Deisseroth et al. |
| 2016/0015996 | A1 | 1/2016 | Deisseroth et al. |
| 2016/0038761 | A1 | 2/2016 | Deisseroth et al. |
| 2016/0038764 | A1 | 2/2016 | Deisseroth et al. |
| 2016/0045599 | A1 | 2/2016 | Deisseroth et al. |

FOREIGN PATENT DOCUMENTS

| | | | |
|---|---|---|---|
| CN | 103313752 | A | 9/2013 |
| CN | 103476456 | A | 12/2013 |
| EP | 1197144 | | 4/2002 |
| EP | 1334748 | | 8/2003 |
| EP | 1444889 | | 8/2004 |
| EP | 1873566 | | 1/2008 |
| JP | 6295350 | | 10/1994 |
| JP | H09505771 | A | 6/1997 |
| JP | 2004534508 | | 11/2004 |
| JP | 2005034073 | A | 2/2005 |
| JP | 2007530027 | A | 11/2007 |
| JP | 2008010422 | A | 1/2008 |
| JP | 2010227537 | A | 10/2010 |
| JP | 2012508581 | | 4/2012 |
| WO | WO 1995/005214 | | 2/1995 |
| WO | WO 1996/032076 | | 10/1996 |
| WO | WO 2000/027293 | | 5/2000 |
| WO | WO 2001/025466 | | 4/2001 |
| WO | WO 2003/016486 | | 2/2003 |
| WO | WO 2003/040323 | | 5/2003 |
| WO | WO 2003/046141 | | 6/2003 |
| WO | WO 2003/084994 | | 10/2003 |
| WO | WO 2003/102156 | | 12/2003 |
| WO | WO 2004/033647 | | 4/2004 |
| WO | WO 2005/093429 | | 10/2005 |
| WO | WO 2006/103678 | | 10/2006 |
| WO | WO 2007/024391 | | 3/2007 |
| WO | WO 2007/131180 | | 11/2007 |
| WO | WO 2008/086470 | | 7/2008 |
| WO | WO 2008/106694 | | 9/2008 |
| WO | WO 2009/025819 | | 2/2009 |
| WO | WO 2009/072123 | | 6/2009 |
| WO | WO 2009/119782 | | 10/2009 |
| WO | WO 2009/131837 | | 10/2009 |
| WO | WO 2009/148946 | | 12/2009 |
| WO | WO 2010/006049 | | 1/2010 |
| WO | WO 2010/011404 | | 1/2010 |
| WO | WO 2010/056970 | | 5/2010 |
| WO | WO 2010/123993 | | 10/2010 |
| WO | WO 2011/005978 | | 1/2011 |
| WO | WO 2011/066320 | | 6/2011 |
| WO | WO 2011/106783 | | 9/2011 |
| WO | WO 2011/116238 | | 9/2011 |
| WO | WO 2011/127088 | | 10/2011 |
| WO | WO 2012/032103 | | 3/2012 |
| WO | WO 2012/061676 | | 5/2012 |
| WO | WO 2012/061681 | | 5/2012 |
| WO | WO 2012/061684 | | 5/2012 |
| WO | WO 2012/061688 | | 5/2012 |
| WO | WO 2012/061690 | | 5/2012 |
| WO | WO 2012/061741 | | 5/2012 |
| WO | WO 2012/061744 | | 5/2012 |
| WO | WO 2012/106407 | | 8/2012 |
| WO | WO 2012/134704 | | 10/2012 |
| WO | WO 2013/003557 | | 1/2013 |
| WO | WO 2013/016486 | | 1/2013 |
| WO | WO 2013/090356 | | 6/2013 |
| WO | WO 2013/126521 | | 8/2013 |
| WO | WO 2013/126762 | | 8/2013 |
| WO | WO 2013/142196 | | 9/2013 |
| WO | WO 2014/081449 | | 5/2014 |
| WO | WO 2014/117079 | | 7/2014 |
| WO | WO 2016/019075 | | 2/2016 |

OTHER PUBLICATIONS

Definition of Implant; Merriam-Webster Dictionary; retrieved Nov. 7, 2016 (http://www.merriam-webster.com/dictionary/implant).
Ferenczi, et al.; "Optogenetic approaches addressing extracellular modulation of neural excitability"; Scientific Reports; vol. 6, 20 pages (Apr. 5, 2016).
Li, et al.; "A Method for Activiation of Endogenous Acid-sensing Ion Channel 1a (ASIC1a) in the Nervous System with High Spatial and Temporal Precision"; The Journal of Biological Chemistry; vol. 289, No. 22, pp. 15441-15448 (May 30, 2014).
Shimizu, et al.; "NMDA Receptor-Dependent Synaptic Reinforcement as a Crucial Process for Memory Consolidation"; Science; vol. 290, pp. 1170-1174 (Nov. 10, 2000).
Zeng, et al.; "Activation of acid-sensing ion channels by localized proton transient reveals their role in proton signaling"; Scientific Reports; vol. 5, 14 pages (Sep. 15, 2015).
Zeng, et al.; "Proton production, regulation and pathophysiological roles in the mammalian brain"; Neuroscience Bulletin; vol. 28, No. 1, pp. 1-13 (Feb. 1, 2012).
Davidson, et al.; "Viral Vectors for Gene Delivery to the Nervous System"; Nature Reviews Neuroscience; vol. 4, pp. 353-364 (May 2003).
Fanselow, et al.; "Why We Think Plasticity Underlying Pavlovian Fear Conditioning Occurs in the Basolateral Amygdala"; Neuron; vol. 23, pp. 229-232 (Jun. 1999).
Rogers, et al.; "Effects of ventral and dorsal CA1 subregional lesions on trace fear conditioning"; Neurobiology of Learning and Memory; vol. 86, pp. 72-81 (2006).
Johnson, et al.; "Differential Biodistribution of Adenoviral Vector in Vivo as Monitored by Bioluminescence Imaging and Quantitative Polymerase Chain Reaction"; Human Gene Therapy; vol. 17, pp. 1262-1269 (Dec. 2006).
Schester, et al.; "Biodistribution of adeno-associated virus serotype 9 (AAV9) vector after intrathecal and intravenous delivery in mouse"; Frontiers in Neuroanatomy; vol. 8, Article 42, pp. 1-41 (Jun. 10, 2014).
Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.
Aebischer, et al. "Long-Term Cross-Species Brain Transplantation of a Polymer-Encapsulated Dopamine-Secreting Cell Line", Experimental Neurology, 1991, vol. 111, pp. 269-275.
Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.
Ahmad, et al. "The Drosophila rhodopsin cytoplasmic tail domain is required for maintenance of rhabdomere structure." The FASEB Journal, 2007, vol. 21, p. 449-455.
Airan, et al., "Temporally Precise in vivo Control of Intracellular Signaling", 2009, Nature, vol. 458, No. 7241, pp. 1025-1029.
Akirav, et al. "The role of the medial prefrontal cortex-amygdala circuit in stress effects on the extinction of fear", Neural Plasticity, 2007: vol. 2007 Article ID:30873, pp. 1-11.
Ali; "Gene and stem cell therapy for retinal disorders"; vision-research.en—The Gateway to European Vision Research; accessed from http://www.vision-research.eu/index.php?id=696, 10 pages (accessed Jul. 24, 2015).
Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.
Araki, et al. "Site-Directed Integration of the cre Gene Mediated by Cre Recombinase Using a Combination of Mutant lox Sites", Nucleic Acids Research, 2002, vol. 30, No. 19, pp. 1-8.

(56) References Cited

OTHER PUBLICATIONS

Aravanis, et al. "An optical neural interface: in vivo control of rodent motor cortex with integrated fiberoptic and optogenetic technology," J. Neural. Eng., 2007, vol. 4(3):S143-S156.
Arenkiel, et al. "In vivo light-induced activation of neural circuitry in transgenic mice expressing Channelrhodopsin-2", Neuron, 2007, 54:205-218.
Argos, et al. "The integrase family of site-specific recombinases: regional similarities and global diversity", The EMBO Journal, 1986, vol. 5, No. 2, pp. 433-440.
Asano, et al.; "Optically Controlled Contraction of Photosensitive Skeletal Muscle Cells"; Biotechnology & Bioengineering; vol. 109, No. 1, pp. 199-204 (Jan. 2012).
Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.
Babin et al., "Zebrafish Models of Human Motor Neuron Diseases: Advantages and Limitations", Progress in Neurobiology (2014), 118:36-58.
Balint et al., "The Nitrate Transporting Photochemical Reaction Cycle of the Pharanois Halorhodopsin", Biophysical Journal, 2004, 86:1655-1663.
Bamberg et al. "Light-driven proton or chloride pumping by halorhodopsin." Proc. Natl. Academy Science USA, 1993, vol. 90, No. 2, p. 639-643.
Banghart, et al. "Light-activated ion channels for remote control of neuronal firing". Nature Neuroscience, 2004, vol. 7, No. 12 pp. 1381-1386.
Barchet, et al.; "Challenges and opportunities in CNS delivery of therapeutics for neurodegenerative diseases"; Expert Opinion on Drug Delivery; vol. 6, No. 3, pp. 211-225 (Mar. 16, 2009).
Basil et al.; "Is There Evidence for Effectiveness of Transcranial Magnetic Stimulation in the Treatment of Psychiatric Disorders?"; Psychiatry; vol. 1, No. 11, pp. 64-69 (Nov. 2005).
Bebbington et al., "The use of vectors based on gene amplification for the expression of cloned genes in mammalian cells in DNA cloning" vol. 3, Academic Press, New York, 1987.
Benabid "Future strategies to restore brain functions," Conference proceedings from Medicine Meets Millennium: World Congress of Medicine and Health, 2000, 6 pages.
Benoist et al. "In vivo sequence requirements of the SV40 early promotor region" Nature (London), 1981, vol. 290(5804): pp. 304-310.
Berges et al., "Transduction of Brain by Herpes Simplex Virus Vectors", Molecular Therapy, 2007, vol. 15, No. 1: pp. 20-29.
Berke, et al. "Addiction, Dopamine, and the Molecular Mechanisms of Memory", Molecular Plasticity, 2000, vol. 25: pp. 515-532.
Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).
Berndt et al. "Bi-stable neural state switches", Nature Neuroscience, 2008, vol. 12, No. 2: pp. 229-234.
Berndt et al., "Structure-guided transformation of channelrhodopsin into a light-activated chloride channel", Science, 2014, 344:420-424.
Berridge et al., "The Versatility and Universality of Calcium Signaling", Nature Reviews: Molecular Cell Biology, 2000, vol. 1: pp. 11-21.
Bi, et al. "Ectopic Expression of a Microbial-Type Rhodopsin Restores Visual Responses in Mice with Photoreceptor Degeneration", Neuron, 2006, vol. 50, No. 1: pp. 23-33.
Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-10472.
Blomer et al., "Highly Efficient and Sustained Gene Transfer in Adult Neurons with Lentivirus Vector", Journal of Virology,1997, vol. 71, No. 9: pp. 6641-6649.
Bocquet et al. "A prokaryotic proton-gated ion channel from the nicotinic acetylcholine receptor family." Nature Letters, 2007, vol. 445, p. 116-119.
Bowers, et al.; "Genetic therapy for the nervous system"; Human Molecular Genetics; vol. 20, No. 1, pp. R28-R41 (2011).
Boyden, et al. "Millisecond-timescale, genetically targeted optical control of neural activity" Nature Neuroscience, 2005, vol. 8, No. 9: pp. 1263-1268.
Braun, "Two Light-activated Conductances in the Eye of the Green Alga Volvox carteri", 1999, Biophys J., vol. 76, No. 3, pp. 1668-1678.
Brewin; "The Nature and Significance of Memory Disturbance in Posttraumatic Stress Disorder"; Ann. Rev. Clin. Psychol.; vol. 7, pp. 203-227 (2011).
Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.
Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.
Brown, et al. "Long-term potentiation induced by θ frequency stimulation is regulated by a protein phosphate-operated gate." The Journal of Neuroscience, 2000, vol. 20, No. 21, pp. 7880-7887.
Bruegmann, et al.; "Optogenetic control of heart muscle in vitro and in vivo"; Nature Methods; vol. 7, No. 11, pp. 897-900(Nov. 2010).
Bruegmann, et al.; "Optogenetics in cardiovascular research: a new tool for light-induced depolarization of cardiomyocytes and vascular smooth muscle cells in vitro and in vivo"; European Heart Journal; vol. 32, No. Suppl . 1, p. 997 (Aug. 2011).
Callaway, et al. "Photostimulation using caged glutamate reveals functional circuitry in living brain slices", Proc. Natl. Acad. Sci. USA., 1993, vol. 90: pp. 7661-7665.
Campagnola et al. "Fiber-coupled light-emitting diode for localized photostimulation of neurons expressing channelrhodopsin-2." Journal of Neuroscience Methods , 2008, vol. 169, Issue 1. Abstract only.
Cardin, et al. "Driving Fast spiking Cells Induces Gamma Rhythm and Controls Sensory Responses", 2009, Nature, vol. 459, vol. 7247, pp. 663-667.
Castagne, et al.; "Rodent Models of Depression: Forced Swim and Tail Suspension Behavioral Despair Tests in Rats and Mice"; Current Protocols in Pharmacology; Supp. 49, Unit 5.8.1-5.8.14 (Jun. 2010).
Cazillis, et al., "VIP and PACAP induce selective neuronal differentiation of mouse embryonic stem cells", Eur J Neurosci, 2004, 19(4):798-808.
Cenatiempo "Prokaryotic gene expression in vitro: transcription-translation coupled systems", Biochimie, 1986, vol. 68(4): pp. 505-515.
Chow et al., "Optogenetics and translation medicine", Sci Transl Med., 2013, 5(177):177.
Clark, et al.; "A future for transgenic livestock"; Nature Reviews Genetics; vol. 4, No. 10, pp. 825-833 (Oct. 2003).
Claudio et al. "Nucleotide and deduced amino acid sequences of Torpedo californica acetylcholine receptor gamma subunit." PNAS USA,1983, vol. 80, p. 1111-1115.
Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of the Medial Prefrontal Cortex." Journal of Neuroscience, 2010, vol. 30(48), pp. 16082-16090.
Cowan et al., "Targeting gene expression to endothelium in transgenic animals: a comparison of the human ICAM-2, PECAM-1, and endoglin promoters", Xenotransplantation, 2003, vol. 10, pp. 223-231.
Crouse, et al. "Expression and amplification of engineered mouse dihydrofolate reductase minigenes" Mol. Cell. Biol. 1983, vol. 3(2): pp. 257-266.
Cucchiaro et al., "Electron-Microscopic Analysis of Synaptic Input from the Perigeniculate Nucleus to A-Laminae of the Lateral

(56) References Cited

OTHER PUBLICATIONS

Geniculate Nucleus in Cats", The Journal of Comparitive Neurology, 1991, vol. 310, pp. 316-336.
Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.
Cui, et al., "Electrochemical deposition and characterization of conducting polymer polypyrrole/PSS on multichannel neural probes," Sensors and Actuators, 2001, vol. 93(1): pp. 8-18.
Dalva, et al. "Rearrangements of Synaptic Connections in Visual Cortex Revealed by Laser Photostimulation", Science, 1994,vol. 265, pp. 255-258.
Date, et al. "Grafting of Encapsulated Dopamine-Secreting Cells in Parkinson's Disease: Long-Term Primate Study", Cell Transplant, 2000, vol. 9, pp. 705-709.
Davis; "The many faces of epidermal growth factor repeats," The New Biologist; vol. 2, No. 5, pp. 410-419 (1990).
Day, et al.; "The Nucleus Accumbens and Pavlovian Reward Learning"; Neuroscientist; vol. 13, No. 2, pp. 148-159 (Apr. 2007).
De Foubert et al. "Fluoxetine-Induced Change in Rat Brain Expression of Brain-Derived Neurotrophic Factor Varies Depending on Length of Treatment," Neuroscience, 2004, vol. 128, pp. 597-604.
De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).
Dederen, et al. "Retrograde neuronal tracing with cholera toxin B subunit: comparison of three different visualization methods", Histochemical Journal, 1994, vol. 26, pp. 856-862.
Definition of Psychosis (2015).
Deisseroth "Next-generation optical technologies for illuminating genetically targeted brain circuits," The Journal of Neuroscience, 2006, vol. 26, No. 41, pp. 10380-10386.
Deisseroth et al., "Excitation-neurogenesis Coupling in Adult Neural Stem/Progenitor Cells", 2004, Neuron, vol. 42, pp. 535-552.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.
Deisseroth et al., "Signaling from Synapse to Nucleus: the logic Behind the Mechanisms", Currrent Opinion in Neurobiology, 2003, vol. 13, pp. 354-365.
Deisseroth et al., "Translocation of Calmodulin to the Nucleus Supports CREB Phosphorylation in Hippocampal Neurons", Nature, 1998, vol. 392, pp. 198-202.
Deisseroth, et al., "Controlling the Brain with Light", Scientific American, 2010, vol. 303, pp. 48-55.
Delaney et al., "Evidence for a long-lived 13-cis-containing intermediate in the photocycle of the leu 93 → ala bacteriorhodopsin mutant", J. Physical Chemistry B, 1997, vol. 101, No. 29, pp. 5619-5621.
Denk, W., et al. "Anatomical and functional imaging of neurons using 2-photon laser scanning microscopy", Journal of Neuroscience Methods, 1994, vol. 54, pp. 151-162.
Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their optical and electrophysiological monitoring in vivo", PNAS, 2004, vol. 101, No. 52, pp. 18206-18211.
Do Carmo, et al.; "Modeling Alzheimer's disease in transgenic rats"; Molecular Neurodegeneration; vol. 8, No. 37, 11 pages (2013).
Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.
Ebert et al., "A Moloney MLV-rat somatotropin fusion gene produces biologically active somatotropin in a transgenic pig", Mol. Endocrinology, 1988, vol. 2, pp. 277-283.
EBI accession No. EMBL: J05199; "N. pharaonis halorhodopsin (hop) gene, complete cds"; (Nov. 22, 1990).
EBI accession No. UNIPROT: A7U0Y6; "SubName: Full=Bacteriorhodopsin"; (Aug. 10, 2010).
EBI accession No. UNIPROT: B0R5N9; "Subname: Full= Bacteriorhodopsin"; (Apr. 8, 2008).
EBI accession No. UNIPROT: B4Y103; "SubName: Full=Channelrhodopsin-1"; (Sep. 23, 2008).
EBI accession No. UNIPROT: P15647; "RecName: Full=Halorhodopsin; Short=HR; Alt Name: Full=NpHR"; (Apr. 1, 1990).
Ehrlich I. et al. "Amygdala inhibitory circuits and the control of fear memory", Neuron, 2009, vol. 62: pp. 757-771.
Eijkelkamp, et al. "Neurological perspectives on voltage-gated sodium channels", Brain, 2012, 135:2585-2612.
Eisen, "Treatment of amyotrophic lateral sclerosis", Drugs Aging, 1999; vol. 14, No. 3, pp. 173-196.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.
Ensell, et al. "Silicon-based microelectrodes for neurophysiology, micromachined from silicon-on-insulator wafers," Med. Biol. Eng. Comput., 2000, vol. 38, pp. 175-179.
Ernst, et al. "Photoactivation of Channelrhodopsin", J. Biol. Chem., 2008, vol. 283, No. 3, pp. 1637-1643.
Esposito et al. "The integrase family of tyrosine recombinases: evolution of a conserved active site domain" , Nucleic Acids Research, 1997, vol. 25, No. 18, pp. 3605-3614.
Evanko "Optical excitation yin and yang" Nature Methods, 2007, 4:384.
Fabian et al. "Transneuronal transport of lectins" Brain Research, 1985, vol. 344, pp. 41-48.
Falconer et al. "High-throughput screening for ion channel modulators," Journal of Biomolecular Screening, 2002, vol. 7, No. 5, pp. 460-465.
Farber, et al. "Identification of Presynaptic Neurons by Laser Photostimulation", Science, 1983, vol. 222, pp. 1025-1027.
Feng, et al. "Imaging Neuronal Subsets in Transgenic Mice Expressing Multiple Spectral Variants of GFP", Neuron, 2000, vol. 28, pp. 41-51.
Fenno et al., "The development and application of optogenetics", Annual Review of Neuroscience, 2011, vol. 34, No. 1, pp. 389-412.
Fiala et al., "Optogenetic approaches in neuroscience", Current Biology, Oct. 2010, 20(20):R897-R903.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Fitzsimons et al., "Promotors and Regulatory Elements that Improve Adeno-Associated Virus Transgene Expression in the Brain", 2002, Methods, vol. 28, pp. 227-236.
Foster, "Bright blue times", Nature, 2005, vol. 433, pp. 698-699.
Fox et al., "A gene neuron expression fingerprint of C. elegans embryonic motor neurons", BMC Genomics, 2005, 6(42):1-23.
Friedman, et al.; "Programmed Acute Electrical Stimulation of Ventral Tegmental Area Alleviates Depressive-Like Behavior"; Neuropsychopharmacology; vol. 34, pp. 1057-1066 (2009).
Garrido et al., "A targeting motif involved in sodium channel clustering at the axonal initial segment", Science, 2003, vol. 300, No. 5628, pp. 2091-2094.
Gelvich et al. "Contact flexible microstrip applicators (CFMA) in a range from microwaves up to short waves," IEEE Transactions on Biomedical Engineering, 2002, vol. 49, Issue 9: 1015-1023.
Genbank Accession No. AAG01180.1; Idnurm, et al.; pp. 1 (Mar. 21, 2001).
Genbank Accession No. ABT17417.1; Sharma, et al.; pp. 1 (Aug. 15, 2007).
GenBank Accession No. AC096118.6; Rattus norvegicus clone CH230-11 B15, 1-4, 24-25, Working Draft Sequence, 3 unordered pieces. May 10, 2003.
Genbank Accession No. BAA09452.1; Mukohata et al.; pp. 1 (Feb. 10, 1999).
Genbank Accession No. DQ094781 (Jan. 15, 2008).
GenBank Accession No. U79717.1; Rattus norvegicus dopamine 02 receptor 1-4, 24-25 gene, promoter region and exon 1. Jan. 31, 1997.

(56) References Cited

OTHER PUBLICATIONS

Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from *Bacillus subtilis* DNA" Gene, 1984, vol. 32(1-2): pp. 11-20.
Glick et al."Factors affecting the expression of foreign proteins in *Escherichia coli*", Journal of Industrial Microbiology, 1987, vol. 1(5): pp. 277-282.
Goekoop, R. et al. "Cholinergic challenge in Alzheimer patients and mild cognitive impairment differentially affects hippocampal activation-a pharmacological fMRI study." Brain, 2006, vol. 129, pp. 141-157.
Gold, et al. "Representation of a perceptual decision in developing oculomotor commands", Nature, 2000, vol. 404, pp. 390-394.
Gonzalez, et al., "Cell-Based Assays and Instrumentation for Screening Ion-Channel Targets", DDT, 1999, vol. 4, No. 9, pp. 431439.
Gordon, et al. "Regulation of Thy-1 Gene Expression in Transgenic Mice", Cell, 1987, vol. 50, pp. 445-452.
Gorelova et al. , "The course of neural projection from the prefrontal cortex to the nucleus accumbens in the rat", Neuroscience, 1997, vol. 76, No. 3, pp. 689-706.
Goshen et al. "Dynamics of Retrieval Strategies for Remote Memories", Cell, 2011, Col. 147: pp. 678-589.
Gottesman et al."Bacterial regulation: global regulatory networks," Ann. Rev. Genet. , 1984, vol. 18, pp. 415-441.
Gradinaru et al., "Optical Deconstruction of Parkinsonian neural circuitry," Science, Apr. 2009, 324(5925):354-359.
Gradinaru et al., "Targeting and readout strategies for fast optical neural control in vitro and in vivo", J Neuroscience, 2007, 27(52):14231-14238.
Gradinaru, et al. "ENpHR: a Natronomonas Halorhodopsin Enhanced for Optogenetic Applications", 2008, Brain Cell Biol., vol. 36 (1-4), pp. 129-139.
Gradinaru, et al., "Molecular and Cellular Approaches for Diversifying and Extending Optogenetics", Cell, 2010, vol. 141, No. 1, pp. 154-165.
Greenberg, et al. "Three-year outcomes in deep brain stimulation for highly resistant obsessive-compulsive disorder," Neuropsychopharmacology, 2006, vol. 31, pp. 2384-2393.
Gregory, et al. "Integration site for *Streptomyces* phage φBT1 and development of site-specific integrating vectors", Journal of Bacteriology, 2003, vol. 185, No. 17, pp. 5320-5323.
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol. , 2005, vol. 94, pp. 3069-3080.
Gulick, et al. "Transfection using DEAE-Dextran" Supplement 40, Current Protocols in Molecular Biology, 1997, Supplement 40, 9.2.1-9.2.10.
Gunaydin et al., "Ultrafast optogenetic control", Nature Neuroscience, 2010, vol. 13, No. 3, pp. 387-392.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Haim, et al.; "Gene Therapy to the Nervous System"; Stem Cell and Gene-Based Therapy; Section 2, pp. 133-154 (2006).
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation in Vivo of a cloned mammalian gene: cadmium induces the transcription of a mouse metallothionein gene in SV40 vectors," Journal of Molecular Applied Genetics, 1982, vol. 1, No. 4, pp. 273-288.
Hammer et al., "Spontaneous inflammatory disease in transgenic rats expressing HLA-B27 and Human $B_2$m: an animal model of HLA-B27-associated human disorders", Cell, 1990, vol. 63, pp. 1099-1112.
Han, et a.; "Virogenetic and optogenetic mechanisms to define potential therapeutic targets in psychiatric disorders"; Neuropharmacology; vol. 62, pp. 89-100 (2012).
Han, et al., "Millisecond-Timescale Optical Control of Neural Dynamics in the Nonhuman Primate Brain"; Neuron; vol. 62, pp. 191-198 (Apr. 30, 2009).
Han, et al., "Multiple-Color Optical Activation, Silencing, and Desynchronization of Neural Activity with Single-Spike Temporal Resolution", PLoS One, 2007, vol. 2, No. 3, pp. 1-12.
Han; et al., "Two-color, bi-directional optical voltage control of genetically-targeted neurons", CoSyne Abstract Presentation, Presented Feb. 24, 2007.
Hausser, et al. "Tonic Synaptic Inhibition Modulates Neuronal Output Pattern and Spatiotemporal Synaptic Integration", Neuron, 1997, vol. 19, pp. 665-678.
Hegemann et al., "All-trans Retinal Constitutes the Functional Chromophore in *Chlamydomonas* rhodopsin", Biophys. J. , 1991, vol. 60, pp. 1477-1489.
Herlitze, et al., "New Optical Tools for Controlling Neuronal Activity", 2007, Curr Opin Neurobiol, vol. 17, No. 1, pp. 87-94.
Herry, et al. "Switching on and off fear by distinct neuronal circuits," Nature, 2008, vol. 454, pp. 600-606.
Heymann, et al.; "Expression of Bacteriorhodopsin in Sf9 and COS-1 Cells"; Journal of Bioenergetics and Biomembranes; vol. 29, No. 1, pp. 55-59 (1997).
Hikida et al., "Acetlycholine enhancement in the nucleus accumbens prevents addictive behaviors of cocaine and morphine", PNAS, May 2003, 100(10):6169-6173.
Hikida et al., "Increased sensitivity to cocaine by cholingergic cell ablation in nucleus accumbens," PNAS, Nov. 2001, 98(23):13351-13354.
Hildebrandt et al, "Bacteriorhodopsin expressed in *Schizosaccharomyces pombe* pumps protons through the plasma membrane," PNAS, 1993, vol. 90, pp. 3578-3582.
Hira et al., "Transcranial optogenetic stimulation for functional mapping of the motor cortex", J Neurosci Methods, 2009, vol. 179, pp. 258-263.
Hirase, et al. "Multiphoton stimulation of neurons", J Neurobiol, 2002, vol. 51, No. 3: pp. 237-247.
Hodaie, et al., "Chronic Anterior Thalamus Stimulation for Intractable Epilepsy," Epilepsia, 2002, vol. 43, pp. 603-608.
Hoffman et al., "K+ Channel Regulation of Signal Propagation in Dendrites of Hippocampal Pyramidal Neurons", 1997, Nature, vol. 387: pp. 869-874.
Hofherr et al. "Selective Golgi export of Kir2.1 controls the stoichiometry of functional Kir2.x channel heteromers"Journal of Cell Science, 2005, vol. 118, p. 1935-1943.
Hosokawa, T. et al. "Imaging spatio-temporal patterns of long-term potentiation in mouse hippocampus." Philos. Trans. R. Soc. Lond. B., 2003, vol. 358, pp. 689-693.
Hustler; et al., "Acetylcholinesterase staining in human auditory and language cortices: regional variation of structural features", Cereb Cortex (Mar.-Apr. 1996), 6(2):260-70.
Hynynen, et al. "Clinical applications of focused ultrasound—The brain." Int. J. Hyperthermia, 2007, vol. 23, No. 2: pp. 193-202.
Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
International Search Report for International Application No. PCT/US2009/053474, dated Oct. 8, 2009.

(56) References Cited

OTHER PUBLICATIONS

Isenberg et al.; "Cloning of a Putative Neuronal Nicotinic Aceylcholine Receptor Subunit"; Journal of Neurochemistry; vol. 52, No. 3, pp. 988-991 (1989).
Iyer et al., "Virally mediated optogenetic excitation and inhibition of pain in freely moving nontransgenic mice", Nat Biotechnol., 2014, 32(3):274-8.
Jekely, "Evolution of Phototaxis", 2009, Phil. Trans. R. Soc. B, vol. 364, pp. 2795-2808.
Jennings et al., "Distinct extended amygdala circuits for divergent motivational states," Nature, 2013, 496:224-228.
Ji et al., "Light-evoked Somatosensory Perception of Transgenic Rats that Express Channelrhodopsin-2 in Dorsal Root Ganglion Cells", PLoS One, 2012 7(3):e32699.
Jimenez S.A & Maren S. et al/ "Nuclear disconnection within the amygdala reveals a direct pathway to fear", Learning Memory, 2009, vol. 16: pp. 766-768.
Johansen, et al., "Optical Activation of Lateral Amygdala Pyramidal Cells Instructs Associative Fear Learning", 2010, PNAS, vol. 107, No. 28, pp. 12692-12697.
Johnston et al. "Isolation of the yeast regulatory gene GAL4 and analysis of its dosage effects on the galactose/melibiose regulon," PNAS, 1982, vol. 79, pp. 6971-6975.
Kaiser; "Clinical research. Death prompts a review of gene therapy vector"; Science; 317(5838):580, 1 page (Aug. 3, 2007).
Kandel, E.R.,et al. "Electrophysiology of Hippocampal Neurons: I. Sequential Invasion and Synaptic Organization," J Neurophysiol, 1961, vol. 24, pp. 225-242.
Kandel, E.R.,et al. "Electrophysiology of Hippocampal Neurons: II. After-Potentials and Repetitive Firing", J Neurophysiol., 1961, vol. 24, pp. 243-259.
Karra, et al. "Transfection Techniques for Neuronal Cells", The Journal of Neuroscience, 2010, vol. 30, No. 18, pp. 6171-6177.
Karreman et al. "On the use of double FLP recognition targets (FRTs) in the LTR of retroviruses for the construction of high producer cell lines" , Nucleic Acids Research, 1996, vol. 24, No. 9: pp. 1616-1624.
Kato et al. "Present and future status of noninvasive selective deep heating using RF in hyperthermia." Med & Biol. Eng. & Comput 31 Supp: S2-11, 1993. Abstract. p. S2 only.
Katz, et al. "Scanning laser photostimulation: a new approach for analyzing brain circuits," Journal of Neuroscience Methods, 1994, vol. 54, pp. 205-218.
Kay; "State-of-the-art gene-based therapies: the road ahead"; Nature Reviews Genetics; vol. 12, pp. 316-328 (May 2011).
Kelder et al., "Glycoconjugates in human and transgenic animal milk", Advances in Exp. Med. and Biol., 2001, vol. 501, pp. 269-278.
Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).
Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.
Khosravani et al., "Voltage-Gated Calcium Channels and Idiopathic Generalized Epilepsies", Physiol. Rev., 2006, vol. 86: pp. 941-966.
Kianianmomeni, et al. "Channelrhodopsins of Volvox carteri are Photochromic Proteins that are Specifically Expressed in Somatic Cells under Control of Light, Temperature, and the Sex Inducer", 2009, Plant Physiology, vol. 151, No. 1, pp. 347-366.
Kim et al., "Diverging neural pathways assemble a behavioural state from separable features in anxiety" Nature, 2013, 496(7444):219-23.
Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.
Kim et al., "PDZ domain proteins of synapses", Nature Reviews Neuroscience, 2004, vol. 5, No. 10, pp. 771-781.
Kingston et al. "Transfection and Expression of Cloned DNA," Supplement 31, Current Protocols in Immunology, 1999, 10.13.1-1 0.13.9.
Kingston et al. "Transfection of DNA into Eukaryotic Cells," Supplement 63, Current Protocols in Molecular Biology, 1996, 9.1.1-9.1.11, 11 pages.
Kinoshita, et al., "Optogenetically Induced Supression of Neural Activity in the Macaque Motor Cortex", Poster Sessions Somatomotor System, Others, Society for Neuroscience Meeting, 2010, pp. 141-154.
Kita, H. et al. "Effects of dopamine agonists and antagonists on optical responses evoked in rat frontal cortex slices after stimulation of the subcortical white matter," Exp. Brain Research, 1999, vol. 125, pp. 383-388.
Kitabatake et al., "Impairment of reward-related learning by cholinergic cell ablationn in the striatum", PNAS, Jun. 2003, 100(13):7965-7970.
Kitayama, et al. "Regulation of neuronal differentiation by N-methyl-D-aspartate receptors expressed in neural progenitor cells isolated from adult mouse hippocampus," Journal of Neurosci Research, 2004, vol. 76, No. 5: pp. 599-612.
Klausberger, et al. "Brain-state- and cell-type-specific firing of hippocampal interneurons in vivo", Nature, 2003, vol. 421: pp. 844-848.
Knopfel, et al. "Optical Probing of Neuronal Circuit Dynamics: Gentically Encoded Versus Classical Fluorescent Sensors", 2006, Trends Neurosci, vol. 29, No. 3, pp. 160-166.
Knopfel, et al.; "A comprehensive concept of optogenetics"; Progress in Brain Research; vol. 196, pp. 1-28 (2012).
Kocsis et al., "Regenerating Mammalian Nerve Fibres: Changes in Action Potential Wavefrom and Firing Characteristics Following Blockage of Potassium Conductance", 1982, Proc. R. Soc. Lond., vol. B 217: pp. 77-87.
Kokel et al., "Photochemical activation of TRPA1 channels in neurons and animals", Nat Chem Biol, 2013, 9(4):257-263.
Kuhlman et al. (2008) "High-Resolution Labeling and Functional Manipulation of Specific Neuron Types in Mouse Brain by Cre-Activated Viral Gene Expression" PLoS One, e2005, vol. 3, No. 4, pp. 1-11.
Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.
Lalumiere, R., "A new technique for controlling the brain: optogenetics and its potential for use in research and the clinic", Brain Stimulation, 2011, vol. 4, pp. 1-6.
Lammel et al., "Input-specific control of reward and aversion in the ventral tegmental area", Nature, 2012, 491(7423): 212-217.
Landy, A. "Mechanistic and structural complexity in the site-specific recombination pathways of Int and FLP", Current Opinion in Genetics and Development, 1993, vol. 3, pp. 699-707.
Lanyi et al. "The primary structure of a Halorhodopsin from Natronobacterium Pharaonis" Journal of Biological Chemistry, 1990, vol. 265, No. 3, p. 1253-1260.
Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.
Lee et al., "Potassium Channel Gene Therapy Can Prevent Neuron Death Resulting from Necrotic and Apoptotic Insults", Journal of Neurochemistry, 2003, vol. 85: pp. 1079-1088.
Levitan et al. "Surface Expression of Kv1 Voltage-Gated K+ Channels is Governed by a C-terminal Motif," Trends Cardiovasc. Med., 2000, vol. 10, No. 7, pp. 317-320.
Li et al. "Fast noninvasive activation and inhibition of neural and network activity by vertebrate rhodopsin and green algae channelrhodopsin." PNAS, 2005, vol. 102, No. 49, p. 17816-17821.
Li et al., "Surface Expression of Kv1 Channels is Governed by a C-Terminal Motif", J. Bioi. Chem. (2000), 275(16):11597-11602.
Lim et al., "A Novel Targeting Signal for Proximal Clustering of the Kv2.1K+ Channel in Hippocampal Neurons", Neuron, 2000, vol. 25: pp. 385-397.

(56) References Cited

OTHER PUBLICATIONS

Lima, et al. "Remote Control of Behavior through Genetically Targeted Photostimulation of Neurons", Cell, 2005, vol. 121: pp. 141-152.
Liman, et al. "Subunit Stoichiometry of a Mammalian K+ Channel Determined by Construction of Multimeric cDNAs," Neuron, 1992,vol. 9, pp. 861-871.
Lin, "A user's guide to channelrhodopsin variants: features, limitations and future developments", Exp Physiol, 2010, vol. 96, No. 1, pp. 19-25.
Liske et al., "Optical inhibition of motor nerve and muscle activity in vivo", Muscle Nerve, 2013, 47(6):916-21.
Liu et al., "Optogenetics 3.0", Cell, Apr. 2010, 141(1):22-24.
Llewellyn et al., "Orderly recruitment of motor units under optical control in vivo", Nat Med., 2010, 16(10):1161-5.
Loetterle, et al., "Cerebellar Stimulation: Pacing the Brain", American Journal of Nursing, 1975, vol. 75, No. 6, pp. 958-960.
Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.
Louis et al. "Cloning and sequencing of the cellular-viral junctions from the human adenovirus type 5 transformed 293 cell line," Virology, 1997, vol. 233, pp. 423-429.
Luecke, et al. "Structural Changes in Bacteriorhodopsin During Ion Transport at 2 Angstrom Resolution," Science, 1999, vol. 286, pp. 255-260.
Lyznik, et al. "FLP-mediated recombination of FRT sites in the maize genome," Nucleic Acids Research , 1996, vol. 24, No. 19: pp. 3784-3789.
Ma et al. "Role of ER Export Signals in Controlling Surface Potassium Channel Numbers," Science, 2001, vol. 291, pp. 316-319.
Malin et al., "Involvement of the rostral anterior cingulate cortex in consolidation of inhibitory avoidance memory: Interaction with the basolateral amygdala", Neurobiol Learn Mem., Feb. 2007, 87(2):295-302.
Mancuso et al., "Optogenetic probing of functional brain circuitry", Experimental Physiology, 2010, vol. 96.1, pp. 26-33.
Mann et at. "Perisomatic Feedback Inhibition Underlies Cholinergically Induced Fast Network Oscillations in the Rat Hippocampus in Vitro," Neuron, 2005, vol. 45, 2005, pp. 105-117.
Mann; "Synapses"; The Nervous System in Action; Chapter 13, http://michaeldmann.net/mann13.html (downloaded Apr. 2014).
Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.
Mattis et al., "Principles for applying optogenetic tools derived from direct comparative analysis of microbial opsins", Nat Methods, 2011, 9(2):159-72.
Mattson, "Apoptosis in Neurodegenerative Disorders", Nature Reviews, 2000, vol. 1: pp. 120-129.
Mayberg et al. "Deep Brain Stimulation for Treatment-Resistant Depression," Focus, 2008, vol. VI, No. 1, pp. 143-154.
Mayford et al., "Control of memory formation through regulated expression of CaMKII transgene", Science, Dec. 1996, 274(5293):1678-1683.
McAllister, "Cellular and Molecular Mechanisms of Dendrite Growth", 2000, Cereb Cortex, vol. 10, No. 10, pp. 963-973.
McKnight "Functional relationships between transcriptional control signals of the thymidine kinase gene of herpes simplex virus", Cell, 1982, vol. 31 pp. 355-365.
Melyan, Z., et al. "Addition of human melanopsin renders mammalian cells Photoresponsive", Nature, 2005, vol. 433: pp. 741-745.
Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.
Meyer, et al. "High density interconnects and flexible hybrid assemblies for active biomedical implants," IEEE Transactions on Advanced Packaging , 2001, vol. 24, No. 3, pp. 366-372.
Milella et al. "Opposite roles of dopamine and orexin in quinpirole-induced excessive drinking: a rat model of psychotic polydipsia" Psychopharmacology, 2010, 211:355-366.
Monje et al., "Irradiation Induces Neural Precursor-Cell Dysfunction", Natural Medicine, 2002, vol. 8, No. 9, pp. 955-962.
Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.
Mortensen et al. "Selection of Transfected Mammalian Cells," Supplement 86, Current Protocols in Molecular Biology, 1997, 9.5.1-09.5.19.
Mourot et al., "Rapid Optical Control of Nociception with an Ion Channel Photoswitch", Nat Methods, 2012, 9(4):396-402.
Mueller, et al.; "Clinical Gene Therapy Using Recombinant Adeno-Associated Virus Vectors"; Gene Therapy; vol. 15, pp. 858-863 (2008).
Mullins et al., "Expression of the DBA/2J Ren-2 gene in the adrenal gland of transgenic mice", EMBO, 1989, vol. 8, pp. 4065-4072.
Mullins et al., "Fulminant hypertension in transgenic rats harbouring the mouse Ren-2 gene", Nature, 1990, vol. 344, pp. 541-544.
Nacher, et al. "NMDA receptor antagonist treatment increases the production of new neurons in the aged rat hippocampus", Neurobiology of Aging, 2003,vol. 24, No. 2: pp. 273-284.
Nagel et al."Functional Expression of Bacteriorhodopsin in Oocytes Allows Direct Measurement of Voltage Dependence of Light Induced H+ Pumping," FEBS Letters, 1995, vol. 377, pp. 263-266.
Nagel, et al. "Channelrhodopsin-I: a light-gated proton channel in green algae", Science, 2002, vol. 296: pp. 2395-2398.
Nagel, et al. "Channelrhodopsin-2, a directly light-gated cation-selective membrane channel", PNAS, 2003, vol. 100, No. 24: pp. 13940-13945.
Nakagami, et al. "Optical Recording of Trisynaptic Pathway in Rat Hippocampal Slices with a Voltage-Sensitive Dye" Neuroscience, 1997, vol. 81, No. 1, pp. 1-8.
Naqvi, et al. "Damage to the insula disrupts addiction to cigarette smoking," Science; 2007, vol. 315 pp. 531-534.
Natochin, et al. "Probing rhodopsin-transducin interaction using Drosophila Rh1-bovine rhodopsin chimeras," Vision Res., 2006, vol. 46, No. 27: pp. 4575-4581.
Nieh et al., "Optogenetic dissection of neural circuits underlying emotional valence and motivated behaviors", Brain Research, E-pub 2012, 1511:73-92.
Nirenberg, et al. "The Light Response of Retinal Ganglion Cells is Truncated by a Displaced Amacrine Circuit", Neuron, 1997, vol. 18: pp. 637-650.
No Authors Listed; "Two bright new faces in gene therapy," Nature Biotechnology, 1996, vol. 14: p. 556.
Nonet, "Visualization of synaptic specializations in live C. elegans with synaptic vesicle protein-GFP fusions", J. Neurosci. Methods, 1999, 89:33-40.
Nunes-Duby, et al. "Similarities and differences among 105 members of the Int family of site-specific recombinases" , Nucleic Acids Research, 1998, vol. 26, No. 2: pp. 391-406.
O'Gorman et al. "Recombinase-mediated gene activation and site-specific integration in mammalian cells", Science, 1991, 251(4999): pp. 1351-1355.
Olivares (2001) "Phage R4 integrase mediates site-specific integration in human cells", Gene, 2001, vol. 278, pp. 167-176.
Ory, et al. "A stable human-derived packaging cell line for production of high titer retrovirus/vesicular stomatitis virus G pseudotypes," PNAS, 1996, vol. 93: pp. 11400-11406.
Packer, et al.; "Targeting Neurons and Photons for Optogenetics"; Nature Neuroscience; vol. 16, No. 7, pp. 805-815 (Jul. 2013).
Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.

(56) References Cited

OTHER PUBLICATIONS

Palmer et al., "The Adult Rat Hippocampus Contains Primordial Neural Stem Cells", Molecular and Cellular Neuroscience, 1997, vol. 8, pp. 389-404.
Pan et al. "Functional Expression of a Directly Light-Gated Membrane Channel in Mammalian Retinal Neurons: A Potential Strategy for Restoring Light Sensitivity to the Retina After Photoreceptor Degeneration"; Investigative Opthalmology & Visual Science, 2005, 46 E-Abstract 4631. Abstract only.
Panda, et al. "Illumination of the Melanopsin Signaling Pathway", Science, 2005, vol. 307: pp. 600-604.
Pandya, et al.; "Where in the Brain is Depression?"; Curr. Psychiatry Rep.; vol. 14, pp. 634-642 (2012).
Pape, et al., "Plastic Synaptic Networks of the Amygdala for the Acquisition, Expression, and Extinction of Conditioned Fear", 2010, Physiol Rev, vol. 90, pp. 419-463.
Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.
Pear "Transient Transfection Methods for Preparation of High-Titer Retroviral Supernatants" Supplement 68, Current Protocols in Molecular Biology, 1996, 9.1 1 .I-9.1 1 .I8.
Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.
Peterlin, et al. "Optical probing of neuronal circuits with calcium indicators," PNAS, 2000, vol. 97, No. 7: pp. 3619-3624.
Petersen et al. "Spatiotemporal Dynamics of Sensory Responses in Layer 2/3 of Rat Barrel Cortex Measured in Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.
Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.
Pettit, et al. "Local Excitatory Circuits in the Intermediate Gray Layer of the Superior Colliculus", J Neurophysiol., 1999, vol. 81, No. 3: pp. 1424-1427.
Pinkham et al., "Neural bases for impaired social cognition in schizophrenia and autism spectrum disorders", Schizophrenia Research, 2008, vol. 99, pp. 164-175.
Potter, "Transfection by Electroporation." Supplement 62, Current Protocols in Molecular Biology, 1996, 9.3.1-9.3.6.
Pouille, et al. "Routing of spike series by dynamic circuits in the hippocampus", Nature, 2004, vol. 429: pp. 717-723.
Qiu et al. "Induction of photosensitivity by heterologous expression of melanopsin", Nature, 2005, vol. 433: pp. 745-749.
Ramalho, et al.; "Mouse genetic corneal disease resulting from transgenic insertional mutagenesis"; Br. J. Ophthalmol.; vol. 88, No. 3, pp. 428-432 (Mar. 2004).
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.
Randic, et al. "Long-term Potentiation and Long-term Depression of Primary Afferent Neurotransmission in the Rat Spinal Cord", 1993, Journal of Neuroscience, vol. 13, No. 12, pp. 5228-5241.
Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct. 2003).
Rathnasingham et al., "Characterization of implantable microfabricated fluid delivery devices," IEEE Transactions on Biomedical Engineering, 2004, vol. 51, No. 1: pp. 138-145.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic System", Brain, 2005, vol. 128 (Pt 6), pp. 1314-1322.
Ristevski; "Making Better Transgenic Models: Conditional, Temporal, and Spatial Approaches"; Molecular Biotechnology; vol. 29, No. 2, pp. 153-163 (Feb. 2005).
Ritter, et al., "Monitoring Light-induced Structural Changes of Channelrhodopsin-2 by UV-Visible and Fourier Transform Infared Spectroscopy", 2008, The Journal of Biological Chemistry, vol. 283, No. 50, pp. 35033-35041.
Rivera et al., "BDNF-Induced TrkB Activation Down-Regulates the K+-Cl- cotransporter KCC2 and Impairs Neuronal Cl-Extrusion", The Journal of Cell Biology, 2002, vol. 159: pp. 747-752.
Rosenkranz, et al. "The prefrontal cortex regulates lateral amygdala neuronal plasticity and responses to previously conditioned stimuli", J. Neurosci., 2003, vol. 23, No. 35: pp. 11054-11064.
Rousche, et al., "Flexible polyimide-based intracortical electrode arrays with bioactive capability," IEEE Transactions on Biomedical Engineering, 2001, vol. 48, No. 3, pp. 361-371.
Rubinson et at. "A lentivirus-based system to functionally silence genes in primary mammalian cells, stem cells and transgenic mice by RNA interference," Nature Genetics, 2003, vol. 33, p. 401-406.
Rudiger et at. "Specific arginine and threonine residues control anion binding and transport in the light-driven chloride pump halorhodopsin," The EMBO Journal, 1997, vol. 16, No. 13, pp. 3813-3821.
Sajdyk, et al., "Excitatory Amino Acid Receptors in the Basolateral Amygdala Regulate Anxiety Responses in the Social Interaction Test", Brain Research, 1997, vol. 764, pp. 262-264.
Salzman, et al. "Cortical microstimulation influences perceptual judgements of motion direction", Nature, 1990, vol. 346, pp. 174-177.
Samuelson; "Post-traumatic stress disorder and declarative memory functioning: a review"; Dialogues in Clinical Neuroscience; vol. 13, No. 3, pp. 346-351 (2011).
Santana et al., "Can Zebrafish Be Used as Animal Model to Study Alzheimer's Disease?" Am. J. Neurodegener. Dis. (2012), 1(1):32-48.
Sato et al. "Role of Anion-binding Sites in cytoplasmic and extracellular channels of *Natronomonas pharaonis* halorhodopsin," Biochemistry, 2005. vol. 44, pp. 4775-4784.
Sauer "Site-specific recombination: developments and applications," Current Opinion in Biotechnology, 1994, vol. 5, No. 5: pp. 521-527.
Schiff, et al. "Behavioral improvements with thalamic stimulation after severe traumatic brain injury," Nature, 2007, vol. 448, pp. 600-604.
Schlaepfer et al. "Deep Brain stimulation to Reward Circuitry Alleviates Anhedonia in Refractory Major Depresion," Neuropsychopharmacology, 2008, vol. 33, pp. 368-377.
Schroll et al., "Light-induced activation of distinct modulatory neurons triggers appetitive or aversive learning in drosophila larvae", Current Biology, Sep. 2006, 16(17):1741-1747.
Sclimenti, et al. "Directed evolution of a recombinase for improved genomic integration at a native human sequence," Nucleic Acids Research, 2001, vol. 29, No. 24: pp. 5044-5051.
Sheikh et al., "Neurodegenerative Diseases: Multifactorial Conformational Diseases and Their Therapeutic Interventions", Journal of Neurodegenerative Diseases (2013), Article ID 563481:1-8.
Shepherd, et al. "Circuit Analysis of Experience-Dependent Plasticity in the Developing Rat Barrel Cortex", Neuron, 2003, vol. 38: pp. 277-289.
Shibasaki et al., "Effects of body temperature on neural activity in the hippocampus: Regulation of resting membrane potentials by transient receptor potential vanilloid 4," The Journal of Neuroscience, 2007, 27(7):1566-1575.
Sigmund; "Viewpoint: Are Studies in Genetically Altered Mice Out of Control?"; Arterioscler Thromb Vasc Biol.; vol. 20, No. 6, pp. 1425-1429 (Jun. 2000).
Silver, et al. "Amino terminus of the yeast GAL4 gene product is sufficient for nuclear localization" PNAS, 1984, vol. 81, No. 19: pp. 5951-5955.

(56) References Cited

OTHER PUBLICATIONS

Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.
Sineshchekov et al.; "Intramolecular Proton Transfer in Channelrhodopsins"; Biophysical Journal; vol. 104, No. 4, pp. 807-807 (Feb. 2013).
Sineshchekov et al., "Two Rhodopsins Mediate Phototaxis to Low and High Intensity Light in Chlamydomas Reinhardtil", PNAS, 2002, vol. 99, No. 13, pp. 8689-8694.
Singer et al. "Elevated Intrasynaptic Dopamine Release in Tourette's Syndrome Measured by PET," American Journal of Psychiatry, 2002, vol. 159: pp. 1329-1336.
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).
Slamovits et al., "A bacterial proteorhodopsin proton pump in marie eukaryotes", Nature Comm, 2011, 2:183.
Slimko et al., "Selective Electrical Silencing of Mammalian Neurons in Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Sohal et al., "Parvalbumin neurons and gamma rhythms enhance cortical circuit performance", Nature, 2009, vol. 459, No. 7247, pp. 698-702.
Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Soofiyani, et al.; "Gene Therapy, Early Promises, Subsequent Problems, and Recent Breakthroughs"; Advanced Pharmaceutical Bulletin; vol. 3, No. 2, pp. 249-255 (2013).
Stark, et al. "Catalysis by site-specific recombinases," Trends Genet., 1992, vol. 8, No. 12: pp. 432-439.
Stockklausner et al. "A sequence motif responsible for ER export and surface expression of Kir2.0 inward rectifier K+ channels," FEBS Letters, 2001, vol. 493, pp. 129-133.
Stoll, et al. "Phage TP901-I site-specific integrase functions in human cells," Journal of Bacteriology, 2002, vol. 184, No. 13: pp. 3657-3663.
Stonehouse, et al.; "Caffeine Regulates Neuronal Expression of the Dopamine 2 Receptor Gene"; Molecular Pharmacology; vol. 64, No. 6, pp. 1463-1473 (2003).
Suzuki et al., "Stable Transgene Expression from HSV Amplicon Vectors in the Brain: Potential Involvement of Immunoregulatory Signals", Molecular Therapy (2008), 16(10):1727-1736.
Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.
Swiss-Prot_Q2QCJ4, Opsin 1, Oct. 31, 2006, URL: http://www.ncbi.nlm.nig.gov/protein/Q2QCJ4.
Takahashi, et al."Diversion of the Sign of Phototaxis in a *Chlamydomonas reinhardtii* Mutant Incorporated with Retinal and Its Analogs," FEBS Letters, 1992, vol. 314, No. 3, pp. 275-279.
Takahashi, et al., "Induction of Pluripotent Stem Cells from Mouse Embryonic and Adult Fibroblast Cultures by Defined Factors", 2006, Cell, vol. 126, pp. 663-676.
Tam, B. et al., "Identification of an Outer Segment Targeting Signal in the COOH Terminus of Rhodopsin Using Transgenic *Xenopus laevis*", The Journal of Cell Biology, 2000, vol. 151, No. 7, pp. 1369-1380.
Tamai, "Progress in Pathogenesis and Therapeutic Research in Retinitis Pigmentosa and Age Related Macular Degeneration", NIPPON GANKA GAKKAI ZASSHI, Dec. 2004, 108(12):750-769.
Tatarkiewicz, et al. "Reversal of Hyperglycemia in Mice After Subcutaneous Transplantation of Macroencapsulated Islets", Transplantation, 1999, vol. 67, No. 5: pp. 665-671.
Taurog et al., "HLA-B27 in inbred and non-inbred transgenic mice", J. Immunol., 1988, vol. 141, pp. 4020-4023.
Thomas et al., "Progress and Problems with the Use of Viral Vectors for Gene", Nat. Rev. Genet. (2003), 4(5):346-358.
Tønnesen, et al., "Optogenetic Control of Epileptiform Activity", PNAS, 2009, vol. 106, No. 29, pp. 12162-12167.
Tottene et al., "Familial Hemiplegic Migraine Mutations Increase $Ca^{2+}$Influx Through Single Human $Ca_v$ 2.1 Current Density in Neurons", PNAS USA, 2002, vol. 99, No. 20: pp. 13284-13289.
Towne et al., "Efficient transduction of non-human primate motor neurons after intramuscular delivery of recombinant AAV serotype 6", Gene Ther., 2010, 17(1):141-6.
Towne et al., "Optogenetic control of targeted peripheral axons in freely moving animals", PLoS One, 2013, 8(8):e72691.
Towne et al., "Recombinant adeno-associated virus serotype 6 (rAAV2/6)-mediated gene transfer to nociceptive neurons through different routes of delivery", Mol Pain, 2009, 5:52.
Tsai, et al., "Phasic Firing in Dopaminergic Neurons in Sufficient for Behavioral Conditioning", Science, 2009, vol. 324, pp. 1080-1084.
Tsau et al. "Distributed Aspects of the Response to Siphon Touch in *Aplysia*: Spread of Stimulus Information and Cross-Correlation Analysis," The Journal of Neuroscience, 1994, vol. 14, No. 7, pp. 4167-4184.
Tye et. al., "Amygdala circuitry mediating reversible and bidirectional control of anxiety", Nature, 2011, vol. 471(7338): pp. 358-362.
Tye et. al., Supplementary Materials: "Amygdala circuitry mediating reversible and bidirectional control of anxiety,", Nature, 2011, vol. 471(7338): pp. 358-362.
Tye, et al. "Optogenetic investigation of neural circuits underlyding brain disease in animal models," Nature Reviews Neuroscience (Mar. 2012), 13(4):251-266.
Ulmanen, et al. "Transcription and translation of foreign genes in *Bacillus subtilis* by the aid of a secretion vector," Journal of Bacteriology, 1985, vol. 162, No. 1: pp. 176-182.
Van Der Linden, "Functional brain imaging and pharmacotherapy in social phobia: single photon emission computed tomography before and after Treatment with the selective serotonin reuptake inhibitor citalopram," Prog Neuro-psychopharmacol Biol Psychiatry, 2000, vol. 24, No. 3: pp. 419-438.
Vanin, et al. "Development of high-titer retroviral producer cell lines by using Cre-mediated recombination," Journal of Virology, 1997, vol. 71, No. 10: pp. 7820-7826.
Varo et al.,"Light-Driven Chloride Ion Transport by Halorhodopsin from Natronobacterium pharaonis. 2. Chloride Release and Uptake, Protein Conformation Change, and Thermodynamics", Biochemistry (1995), 34(44):14500-14507.
Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.
Wagner, "Noninvasive Human Brain Stimulation", Annual Rev. Biomed. Eng. 2007. 9:I9.I-19.39.
Wall, "Transgenic livestock: Progress and prospects for the future", Theriogenology, 1996, vol. 45, pp. 57-68.
Wang, et al. "Direct-current Nanogenerator Driven by Ultrasonic Waves," Science, 2007, vol. 316, pp. 102-105.
Wang, et al., "High-speed mapping of synaptic connectivity using photostimulation in Channelrhodopsin-2 transgenic mice", PNAS, 2007, vol. 104, No. 19, pp. 8143-8148.
Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.

(56) References Cited

OTHER PUBLICATIONS

Wang, et al., "Mrgprd-Expressing Polymodal Nociceptive Neurons Innervate Most Known Classes of Substantia Gelatinosa Neurons", J Neurosci, 2009, 29(42):13202-13209.
Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).
Ward, et al. "Construction and characterisation of a series of multi-copy promoter-probe plasmid vectors for *Streptomyces* using the aminoglycoside phosphotransferase gene from Tn5 as indicator", 1986, Mol. Gen. Genet., vol. 203: pp. 468-478.
Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.
Weick et al. "Interactions with PDZ Proteins Are Required for L-Type Calcium Channels to Activate cAMP Response Element-Binding Protein-Dependent Gene Expression," The Journal of Neuroscience, 2003, vol. 23, No. 8, pp. 3446-3456.
Wells et al. "Application of Infrared light for in vivo neural stimulation," Journal of Biomedical Optics, 2005, vol. 10(6), pp. 064003-1-064003-12.
Williams et al., "From optogenetic technologies to neuromodulation therapies", Sci Transl Med., 2013, 5(177):177.
Witten et. al., "Cholinergic Interneurons Control Local Circuit Activity and Cocaine Conditioning", Science, 2010, vol. 330, No. 6011: pp. 1677-1681.
Witten et. al., Supporting Online Material for: "Cholinergic Interneurons Control Local Circuit Activity and Cocaine Conditioning", Science, 2010, vol. 330:17 pages.
Written opinion of PCT Application No. PCT/US2011/059383 (dated May 9, 2012).
Xiong et al., "Interregional connectivity to primary motor cortex revealed using MRI resting state images", Hum Brain Mapp, 1999, 8(2-3):151-156.
Yamazoe, et al. "Efficient generation of dopaminergic neurons from mouse embryonic stem cells enclosed in hollow fibers", Biomaterials, 2006, vol. 27, pp. 4871-4880.
Yan et al., "Cloning and Characterization of a Human β,βCarotene-15, 15'-Dioxygenase that is Highly Expressed in the Retinal Pigment Epithelium", Genomics, 2001, vol. 72: pp. 193-202.
Yizhar et al., "Optogenetics in neural systems", Neuron Primer, vol. 71, No. 1, pp. 9-34 (Jul. 14, 2011).
Yizhar et. al., "Neocortical excitation/inhibition balance in information processing and social dysfunction", Nature, 2011, vol. 477, pp. 171-178; and Supplemental Materials; 41 pages.
Yoon, et al., "A micromachined silicon depth probe for multichannel neural recording," IEEE Transactions Biomedical Engineering, 2000, vol. 47, No. 8, pp. 1082-1087.
Yoshimura, et al. "Excitatory cortical neurons form fine-scale functional networks", Nature, 2005, vol. 433: pp. 868-873.
Zacharias et al. "Recent advances in technology for measuring and manipulating cell signals," Current Opinion in Neurobiology, 2000, vol. 10: pp. 416-421.
Zemelman, et al. "Selective Photostimulation of Genetically ChARGed Neurons", Neuron, 2002, vol. 33: pp. 15-22.
Zemelman, et al. "Photochemical gating of heterologous ion channels: Remote control over genetically designated populations of neurons", PNAS, 2003, vol. 100, No. 3: pp. 1352-1357.
Zhang "Multimodal fast optical interrogation of neural circuitry," Nature, 2007, vol. 446, pp. 633-641.
Zhang, et al. "Channelrhodopsin-2 and optical control of excitable cells," Nature Methods,2006, vol. 3, No. 10, pp. 785-792.
Zhang, et al. "Red-Shifted Optogenetic Excitation: a Tool for Fast Neural Control Derived from *Volvox carteri*", Nature Neurosciences, 2008,vol. 11, No. 6, pp. 631-633.
Zhang, et al., "The Microbial Opsin Family of Optogenetic Tools", Cell, 2011, vol. 147, No. 7, pp. 1146-1457.
Zhang, et al.; "Optogenetic interrogation of neural circuits: Technology for probing mammalian brain structures"; Nature Protocols; vol. 5, No. 3, pp. 439-456 (Feb. 18, 2010).
Zhao, et al., "Improved Expression of Halorhodopsin for Light-Induced Silencing of Neuronal Activity", Brain Cell Biology, 2008, vol. 36 (1-4), pp. 141-154.
Zrenner, E., "Will Retinal Implants Restore Vision?" Science, 2002, vol. 295, No. 5557, pp. 1022-1025.
Zufferey, et al. "Self-Inactivating Lentivirus Vector for Safe and Efficient in Vivo Gene Delivery", Journal of Virology, 1998, vol. 72, No. 12, pp. 9873-9880.
Airan, et al.; "Integration of light-controlled neuronal firing and fast circuit imaging"; Current Opinion in Neurobiology; vol. 17, pp. 587-592 (2007).
Cannon, et al.; "Endophenotypes in the Genetic Analyses of Mental Disorders"; Annu. Rev. Clin. Psychol.; vol. 2, pp. 267-290 (2006).
Chamanzar, et al.; "Deep Tissue Targeted Near-infrared Optogenetic Stimulation using Fully Implantable Upconverting Light Bulbs"; 2015 37th Annual International Conference of the IEEE Engineering in Medicine and Biology Society (EMBC), IEEE; doi: 10.1109/EMBC.2015.7318488, pp. 821-824 (Aug. 25, 2015).
Chinta, et al.; "Dopaminergic neurons"; The International Journal of Biochemistry & Cell Biology; vol. 37, pp. 942-946 (2005).
Deonarain; "Ligand-targeted receptor-mediated vectors for gene delivery"; Exp. Opin. Ther. Patents; vol. 8, No. 1, pp. 53-69 (1998).
Edelstein, et al.; "Gene therapy clinical trials worldwide 1989-2004—an overview"; The Journal of Gene Medicine; vol. 6, pp. 597-602 (2004).
Grady, et al.; "Age-Related Reductions in Human Recognition Memory Due to Impaired Encoding"; Science; vol. 269, No. 5221, pp. 218-221 (Jul. 14, 1995).
Hososhima, et al.; "Near-infrared (NIR) up-conversion optogenetics"; Optical Techniques in Neurosurgery, Neurophotonics, and Optogenetics II; vol. 9305, doi: 10.1117/12.2078875, 4 pages (2015).
Johnson-Saliba, et al.; "Gene Therapy: Optimising DNA Delivery to the Nucleus"; Current Drug Targets; vol. 2, pp. 371-399 (2001).
Palu, et al.; "In pursuit of new developments for gene therapy of human diseases"; Journal of Biotechnology; vol. 68, pp. 1-13 (1999).
Petersen, et al.; "Functionally Independent Columns of Rat Somatosensory Barrel Cortex Revealed with Voltage-Sensitive Dye Imaging"; J. of Neuroscience; vol. 21, No. 21, pp. 8435-8446 (Nov. 1, 2011).
Pfeifer, et al.; "Gene Therapy: Promises and Problems"; Annu. Rev. Genomics Hum. Genet.; vol. 2, pp. 177-211 (2001).
Powell, et al.; "Schizophrenia-Relevant Behavioral Testing in Rodent Models: A Uniquely Human Disorder?"; Biol. Psychiatry; vol. 59, pp. 1198-1207 (2006).
Shoji, et al.; "Current Status of Delivery Systems to Improve Target Efficacy of Oligonucleotides"; Current Pharmaceutical Design; vol. 10, pp. 785-796 (2004).
Verma, et al.; "Gene therapy—promises, problems and prospects"; Nature; vol. 389, pp. 239-242 (Sep. 1997).
Wang, et al.; "Simultaneous phase and size control of upconversion nanocrystals through lanthanide doping"; Nature; vol. 463, No. 7284, pp. 1061-1065 (Feb. 25, 2010).
Yajima, et al., "Effects of bromazepam on responses of mucosal blood flow of the gastrointestinal tract and the gastric motility to stimulation of the amygdala and hypothalamus in conscious cats"; Folia Pharmacol. Japon; vol. 83, No. 3, pp. 237-248 (Mar. 1984). [English abstract translation].
Yamada, Shigeto; "Neurobiological Aspects of Anxiety Disorders"; The Japanese Journal of Psychiatry; vol. 8, No. 6, pp. 525-535 (Nov. 25, 2003). [English translation of introduction and summary].
Co-pending U.S. Appl. No. 14/822,552, filed Aug. 10, 2015.
Co-pending U.S. Appl. No. 14/886,763, filed Oct. 19, 2015.
Co-pending U.S. Appl. No. 14/911,405, filed Feb. 26, 2016.
Co-pending U.S. Appl. No. 15/008,214, filed Jan. 27, 2016.
Co-pending U.S. Appl. No. 15/059,159, filed Mar. 2, 2016.
Azizgolshani, et al.; "Reconstituted plant viral capsids can release genes to mammalian cells"; Virology; vol. 441, No. 1, pp. 12-17 (2013).

(56) References Cited

OTHER PUBLICATIONS

Racaniello; "How many viruses on Earth?"; Virology Blog; 6 pages; http://www.virology.ws/2013/09/06/how-many-viruses-on-earth/ (Sep. 6, 2013).
Lin, et al.; "Study of the Circuitry of Nucleus Accumbens and its Effect on Addiction by Optogenetic Methods: 964"; Neurosurgery; vol. 67, No. 2, pp. 557 (Aug. 2010).
Tsuchida; "Nervous Control of Micturition"; The Japanese Journal of Urology; vol. 80, No. 9, pp. 1257-1277 (1989).
Abbott, et al.; "Photostimulation of Retrotrapezoid Nucleus Phox2b-Expressing Neurons in Vivo Produces Long-Lasting Activation of Breathing in Rats"; The Journal of Neuroscience; vol. 29, No. 18, pp. 5806-5819 (May 6, 2009).
Alilain, et al.; "Light-Induced Rescue of Breathing after Spinal Cord Injury"; The Journal of Neuroscience; vol. 28, No. 46, pp. 11862-11870 (Nov. 12, 2008).
Cardin, et al.; "Targeted optogenetic stimulation and recording of neurons in vivo using cell-type-specific expression of Channelrhodopsin-2"; Nature Protocols; vol. 5, No. 2, pp. 247-254 (2010).
Caro, et al.; "Engineering of an Artificial Light-Modulated Potassium Channel"; PLoS One; vol. 7, Issue 8, e43766 (Aug. 2012).
Coleman, et al.; "Assessing Anxiety in Nonhuman Primates"; Ilar Journal; vol. 55, No. 2, pp. 333-346 (2014).
Hagglund, et al.; "Activation of groups of excitatory neurons in the mammalian spinal cord or hindbrain evokes locomotion"; Nature Neuroscience; vol. 13, No. 2, 8 pages (Feb. 2010).
Kleinlogel, et al.; "A gene-fusion strategy for stoichiometric and co-localized expression of light-gated membrane proteins"; Nature Methods; vol. 8, No. 12, pp. 1083-1091 (Dec. 2011).
Kravitz, et al.; "Regulation of parkinsonian motor behaviours by optogenetic control of basal ganglia circuitry"; Nature; vol. 466, No. 622, 8 pages (Jul. 29, 2010).
Luo, et al.; "Synthetic DNA delivery systems"; Nature Biotechnology; vol. 18, pp. 33-37 (Jan. 2000).
Maestripieri, et al.; "A modest proposal: displacement activities as an indicator of emotions in primates"; Anim. Behav.; vol. 44, pp. 967-979 (1992).
Nelson, et al.; "Non-Human Primates: Model Animals for Developmental Psychopathology"; Neuropsychopharmacology; vol. 34, No. 1, pp. 90-105 (Jan. 2009).
Tomita, et al.; "Visual Properties of Transgenic Rats Harboring the Channelrhodopsin-2 Gene Regulated by the Thy-1.2 Promoter"; PLoS One; vol. 4, No. 11, 13 pages (Nov. 2009).
Uniprot Accession No. P02945, integrated into the database on Jul. 21, 1986.
Definition of integral. Merriam-Webster Dictionary, retrieved on Mar. 20 2017; Retrieved from the Internet: <http://www.merriam-webster.com/dictionary/integral>.
Gritton, et al.; "Optogenetically-evoked cortical cholinergic transients in mice expressing channelrhodopsin-2 (ChR2) in cholinergic neurons"; Society for Neuroscience Abstract Viewer and Itinery Planner & 40th Annual Meeting of the Society-for-Neuroscience; vol. 40, 2 pages (2010).
Sofuoglu, et al.; "Cholinergic Functioning in Stimulant Addiction: Implications for Medications Development"; CNS Drugs; vol. 23, No. 11, pp. 939-952 (Nov. 1, 2009).
Witten, et al.; "Cholinergic interneurons of the nucleus accumbens control local circuit activity and reward behavior"; Society for Neuroscience Abstract Viewer and Itinerary Planner & 40th Annual Meeting of the Society-for-Neuroscience; vol. 40, 2 pages (2010).

EF-1α::NpHR-EYFP

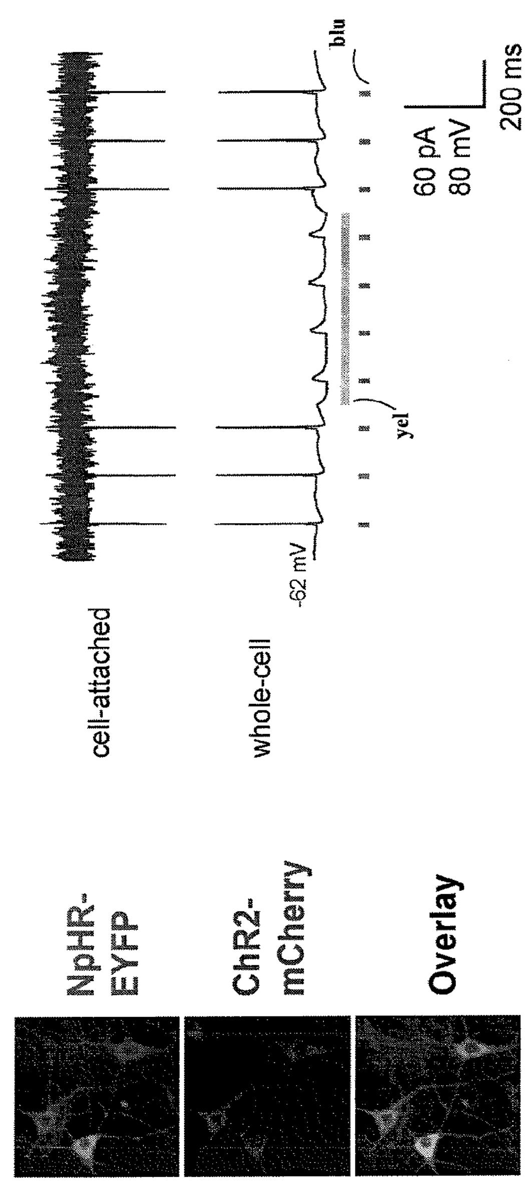
FIG. 1I
NpHR-EYFP
ChR2-mCherry
Overlay
FIG. 1J
cell-attached
whole-cell
-62 mV
yel
blu
60 pA
80 mV
200 ms
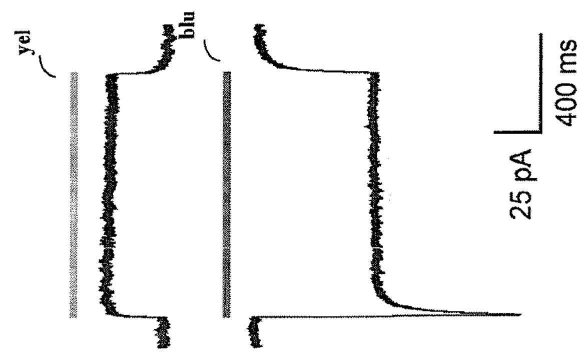
FIG. 1K
yel
blu
25 pA
400 ms Percentage of Inhibited Spikes (%, $n = 7$)

100 75 50 25 0

7.2 10.9 21.7

Light Intensity (mW/mm$^2$)

Light Onset to First Escaped Spike (ms, $n = 7$)

1200 900 600 300 0

7.2 10.9 21.7

Light Intensity (mW/mm$^2$)

502
Light Source
504
506
508
510
512

614
612
610
602
Inhibitory Current Light Source (Wavelength A)
604
Excitation Current Light Source (Wavelength B)

SEQUENCE LISTING

```
<160> NUMBER OF SEQ ID NOS: 24

<210> SEQ ID NO 1
<211> LENGTH: 1599
<212> TYPE: DNA
<213> ORGANISM: Artificial Sequence
<220> FEATURE:
<223> OTHER INFORMATION: humanized codon optimized sequence from
      Natronomonas pharaonis

<400> SEQUENCE: 1
```

```
atgacagaga ccctgcctcc cgtgaccgag agtgccgtgg cccttcaagc cgaggttacc     60

caaagggagt tgttcgagtt cgtgctgaac gaccctttgc ttgcaagcag tctctatatc    120

aacatcgcac ttgcaggact gagtatactg ctgttcgttt ttatgacccg aggactcgat    180

gatccacggg caaaacttat tgctgtgtca accatccttg tgcctgtcgt cagcattgcc    240

tcctacactg gattggcgag cggcctgaca atttccgttc ttgaaatgcc agcgggccat    300

tttgcagaag gcagctcagt gatgctggga ggagaagagg tagatggtgt agtcaccatg    360

tggggacggt atctcacctg ggcactttcc acgcccatga ttctcctcgc tctgggtctc    420

ctggccggaa gcaatgctac aaagctcttc acagctatca ctttcgatat cgctatgtgc    480

gtgactggcc ttgccgcggc cctgactacc tcctcccacc tcatgagatg gttctggtac    540

gctatcagtt gtgcatgctt tctggtggtc ttgtatatcc tgctggtgga gtgggcacag    600

gacgccaaag ccgcgggaac cgctgacatg ttcaataccc tgaagctgtt gacagtagtg    660

atgtggctgg ggtatccaat tgtgtgggct cttggagtcg agggtatcgc ggtgttgccc    720

gttggggtga cgagctgggg atattctttc ctggatatcg tggcaaagta cattttcgca    780

ttcttgctcc tgaactatct gacgtcaaac gaatctgtcg tgtccggcag cattttggat    840

gttccatctg cttctgggac cccggctgat gatgcggccg ccgtgagcaa gggcgaggag    900

ctgttcaccg ggtggtgcc catcctggtc gagctggacg gcgacgtaaa cggccacaag     960

ttcagcgtgt ccggcgaggg cgagggcgat gccacctacg gcaagctgac cctgaagttc   1020

atctgcacca ccggcaagct gcccgtgccc tggcccaccc tcgtgaccac cttcggctac   1080

ggcctgcagt gcttcgcccg ctaccccgac cacatgaagc agcacgactt cttcaagtcc   1140

gccatgcccg aaggctacgt ccaggagcgc accatcttct tcaaggacga cggcaactac   1200

aagacccgcg ccgaggtgaa gttcgagggc gacaccctgg tgaaccgcat cgagctgaag   1260

ggcatcgact tcaaggagga cggcaacatc ctggggcaca agctggagta caactacaac   1320

agccacaacg tctatatcat ggccgacaag cagaagaacg gcatcaaggt gaacttcaag   1380

atccgccaca acatcgagga cggcagcgtg cagctcgccg accactacca gcagaacacc   1440

cccatcggcg acggccccgt gctgctgccc gacaaccact acctgagcta ccagtccgcc   1500

ctgagcaaag accccaacga gaagcgcgat cacatggtcc tgctggagtt cgtgaccgcc   1560

gccgggatca ctctcggcat ggacgagctg tacaagtaa                          1599
```

<210> SEQ ID NO 2
<211> LENGTH: 1599
<212> TYPE: DNA
<213> ORGANISM: Artificial Sequence
<220> FEATURE:
<223> OTHER INFORMATION: Original codons from from Natronomonas pharaonis with EYEFP

<400> SEQUENCE: 2

```
atgactgaga cattgccacc ggtaacggaa tcggctgttg cgctacaggc ggaggtgacc     60

cagagggagc tgttcgagtt cgttctcaac gacccccctcc tcgccagttc gctgtatatt   120

aatatcgcac tggcagggct gtcgatactg cttttcgtgt tcatgacgcg cggactcgac    180

gacccacggg cgaaactcat cgccgtttcg acgattttgg tgccggtggt ctctatcgcg    240

agctacaccg gccttgcatc ggggctcacc atcagcgtcc tcgagatgcc agccggccac    300

ttcgccgagg ggtcctcggt gatgctcggc ggcgaagagg tagacggcgt cgtgacgatg    360

tggggccgct atctgacgtg ggccctttcg acaccgatga tactgctggc gcttgggctg    420
```

```
cttgctggct ctaacgccac gaagctcttt accgccatca ccttcgacat cgcgatgtgt    480

gtcaccggcc tcgcagccgc gctgacgacc tcttcgcacc tgatgcggtg gttctggtac    540

gccatcagtt gtgcgtgttt cctcgtcgtc ctctacatcc tgctcgtcga gtgggcacag    600

gacgccaagg ctgccggtac tgcggatatg ttcaatacgc tgaagctgct gaccgttgtc    660

atgtggctcg gctaccccat cgtgtgggca ctcggcgttg agggcatcgc cgttcttccg    720

gtcggagtca cgtcgtgggg atacagcttc ctcgacatcg tcgcgaagta catcttcgcg    780

ttcctgctgc tcaactacct cacgtcgaac gagagcgtcg tctccggctc gatactcgac    840

gtgccgtccg cgtcgggcac tcccgctgac gacgcggccg ccgtgagcaa gggcgaggag    900

ctgttcaccg gggtggtgcc catcctggtc gagctggacg gcgacgtaaa cggccacaag    960

ttcagcgtgt ccggcgaggg cgagggcgat gccacctacg gcaagctgac cctgaagttc   1020

atctgcacca ccggcaagct gcccgtgccc tggcccaccc tcgtgaccac cttcggctac   1080

ggcctgcagt gcttcgcccg ctaccccgac cacatgaagc agcacgactt cttcaagtcc   1140

gccatgcccg aaggctacgt ccaggagcgc accatcttct tcaaggacga cggcaactac   1200

aagacccgcg ccgaggtgaa gttcgagggc gacaccctgg tgaaccgcat cgagctgaag   1260

ggcatcgact tcaaggagga cggcaacatc ctggggcaca agctggagta caactacaac   1320

agccacaacg tctatatcat ggccgacaag cagaagaacg gcatcaaggt gaacttcaag   1380

atccgccaca acatcgagga cggcagcgtg cagctcgccg accactacca gcagaacacc   1440

cccatcggcg acggccccgt gctgctgccc gacaaccact acctgagcta ccagtccgcc   1500

ctgagcaaag accccaacga gaagcgcgat cacatggtcc tgctggagtt cgtgaccgcc   1560

gccgggatca ctctcggcat ggacgagctg tacaagtaa                          1599


<210> SEQ ID NO 3
<211> LENGTH: 1641
<212> TYPE: DNA
<213> ORGANISM: Artificial Sequence
<220> FEATURE:
<223> OTHER INFORMATION: humanized codon optimized sequence from
      Natronomonas pharaonis with signal peptide (23aa) from nicotinic
      acetylcholine receptor added to the N-terminus

<400> SEQUENCE: 3

atgaggggta cgcccctgct cctcgtcgtc tctctgttct ctctgcttca ggacacagag     60

accctgcctc ccgtgaccga gagtgccgtg gcccttcaag ccgaggttac ccaaagggag    120

ttgttcgagt tcgtgctgaa cgaccctttg cttgcaagca gtctctatat caacatcgca    180

cttgcaggac tgagtatact gctgttcgtt tttatgaccc gaggactcga tgatccacgg    240

gcaaaactta ttgctgtgtc aaccatcctt gtgcctgtcg tcagcattgc ctcctacact    300

ggattggcga gcggcctgac aatttccgtt cttgaaatgc cagcgggcca ttttgcagaa    360

ggcagctcag tgatgctggg aggagaagag gtagatggtg tagtcaccat gtggggacgg    420

tatctcacct gggcactttc cacgcccatg attctcctcg ctctgggtct cctggccgga    480

agcaatgcta caaagctctt cacagctatc actttcgata tcgctatgtg cgtgactggc    540

cttgccgcgg ccctgactac ctcctcccac ctcatgagat ggttctggta cgctatcagt    600

tgtgcatgct ttctggtggt cttgtatatc ctgctggtgg agtgggcaca ggacgccaaa    660

gccgcgggaa ccgctgacat gttcaatacc ctgaagctgt tgacagtagt gatgtggctg    720

ggtatccaa ttgtgtgggc tcttggagtc gagggtatcg cggtgttgcc cgttggggtg    780
```

-continued acgagctggg gatattcttt cctggatatc gtggcaaagt acattttcgc attcttgctc 840
ctgaactatc tgacgtcaaa cgaatctgtc gtgtccggca gcattttgga tgttccatct 900
gcttctggga ccccggctga tgatgtgagc aagggcgagg agctgttcac cggggtggtg 960
cccatcctgg tcgagctgga cggcgacgta aacggccaca agttcagcgt gtccggcgag 1020
ggcgagggcg atgccaccta cggcaagctg accctgaagt tcatctgcac caccggcaag 1080
ctgcccgtgc cctggcccac cctcgtgacc accttcggct acggcctgca gtgcttcgcc 1140
cgctaccccg accacatgaa gcagcacgac ttcttcaagt ccgccatgcc cgaaggctac 1200
gtccaggagc gcaccatctt cttcaaggac gacggcaact acaagacccg cgccgaggtg 1260
aagttcgagg gcgacaccct ggtgaaccgc atcgagctga agggcatcga cttcaaggag 1320
gacggcaaca tcctggggca caagctggag tacaactaca acagccacaa cgtctatatc 1380
atggccgaca agcagaagaa cggcatcaag gtgaacttca agatccgcca caacatcgag 1440
gacggcagcg tgcagctcgc cgaccactac cagcagaaca cccccatcgg cgacggcccc 1500
gtgctgctgc ccgacaacca ctacctgagc taccagtccg ccctgagcaa agaccccaac 1560
gagaagcgcg atcacatggt cctgctggag ttcgtgaccg ccgccgggat cactctcggc 1620
atggacgagc tgtacaagta a 1641

<210> SEQ ID NO 4
<211> LENGTH: 1605
<212> TYPE: DNA
<213> ORGANISM: Artificial Sequence
<220> FEATURE:
<223> OTHER INFORMATION: humanized codon optimized sequence from Natronomonas pharaonis with the PDZ binding motif ETQZ added to the C-terminus

<400> SEQUENCE: 4
atgacagaga ccctgcctcc cgtgaccgag agtgccgtgg cccttcaagc cgaggttacc 60
caaagggagt tgttcgagtt cgtgctgaac gaccctttgc ttgcaagcag tctctatatc 120
aacatcgcac ttgcaggact gagtatactg ctgttcgttt ttatgacccg aggactcgat 180
gatccacggg caaaacttat tgctgtgtca accatccttg tgcctgtcgt cagcattgcc 240
tcctacactg gattggcgag cggcctgaca atttccgttc ttgaaatgcc agcgggccat 300
tttgcagaag gcagctcagt gatgctggga ggagaagagg tagatggtgt agtcaccatg 360
tggggacggt atctcacctg ggcactttcc acgcccatga ttctcctcgc tctgggtctc 420
ctggccggaa gcaatgctac aaagctcttc acagctatca ctttcgatat cgctatgtgc 480
gtgactggcc ttgccgcggc cctgactacc tcctcccacc tcatgagatg gttctggtac 540
gctatcagtt gtgcatgctt tctggtggtc ttgtatatcc tgctggtgga gtgggcacag 600
gacgccaaag ccgcgggaac cgctgacatg ttcaataccc tgaagctgtt gacagtagtg 660
atgtggctgg ggtatccaat tgtgtgggct cttggagtcg agggtatcgc ggtgttgccc 720
gttggggtga cgagctgggg atattctttc ctggatatcg tggcaaagta cattttcgca 780
ttcttgctcc tgaactatct gacgtcaaac gaatctgtcg tgtccggcag cattttggat 840
gttccatctg cttctgggac cccggctgat gatatggtga gcaagggcga ggagctgttc 900
accggggtgg tgcccatcct ggtcgagctg gacggcgacg taaacggcca caagttcagc 960
gtgtccggcg agggcgaggg cgatgccacc tacggcaagc tgaccctgaa gttcatctgc 1020
accaccggca agctgcccgt gccctggccc accctcgtga ccaccttcgg ctacggcctg 1080
cagtgcttcg cccgctaccc cgaccacatg aagcagcacg acttcttcaa gtccgccatg 1140

```
cccgaaggct acgtccagga gcgcaccatc ttcttcaagg acgacggcaa ctacaagacc   1200

cgcgccgagg tgaagttcga gggcgacacc ctggtgaacc gcatcgagct gaagggcatc   1260

gacttcaagg aggacggcaa catcctgggg cacaagctgg agtacaacta caacagccac   1320

aacgtctata tcatggccga caagcagaag aacggcatca aggtgaactt caagatccgc   1380

cacaacatcg aggacggcag cgtgcagctc gccgaccact accagcagaa cacccccatc   1440

ggcgacggcc ccgtgctgct gcccgacaac cactacctga gctaccagtc cgccctgagc   1500

aaagacccca acgagaagcg cgatcacatg gtcctgctgg agttcgtgac cgccgccggg   1560

atcactctcg gcatggacga gctgtacaag gagacccagg tgtaa                    1605
```

<210> SEQ ID NO 5
<211> LENGTH: 1611
<212> TYPE: DNA
<213> ORGANISM: Artificial Sequence
<220> FEATURE:
<223> OTHER INFORMATION: humanized codon optimized sequence from Natronomonas pharaonis with the PTPP sequence added to the C-terminus to promote interaction with actin-binding protein filamin

<400> SEQUENCE: 5

```
atgacagaga ccctgcctcc cgtgaccgag agtgccgtgg cccttcaagc cgaggttacc     60

caaagggagt tgttcgagtt cgtgctgaac gaccctttgc ttgcaagcag tctctatatc    120

aacatcgcac ttgcaggact gagtatactg ctgttcgttt ttatgacccg aggactcgat    180

gatccacggg caaaacttat tgctgtgtca accatccttg tgcctgtcgt cagcattgcc    240

tcctacactg gattggcgag cggcctgaca atttccgttc ttgaaatgcc agcgggccat    300

tttgcagaag gcagctcagt gatgctggga ggagaagagg tagatggtgt agtcaccatg    360

tggggacggt atctcacctg ggcactttcc acgcccatga ttctcctcgc tctgggtctc    420

ctggccggaa gcaatgctac aaagctcttc acagctatca ctttcgatat cgctatgtgc    480

gtgactggcc ttgccgcggc cctgactacc tcctcccacc tcatgagatg gttctggtac    540

gctatcagtt gtgcatgctt tctggtggtc ttgtatatcc tgctggtgga gtgggcacag    600

gacgccaaag ccgcgggaac cgctgacatg ttcaataccc tgaagctgtt gacagtagtg    660

atgtggctgg ggtatccaat tgtgtgggct cttggagtcg agggtatcgc ggtgttgccc    720

gttggggtga cgagctgggg atattctttc ctggatatcg tggcaaagta cattttcgca    780

ttcttgctcc tgaactatct gacgtcaaac gaatctgtcg tgtccggcag cattttggat    840

gttccatctg cttctgggac cccggctgat gatgcggccg ccgtgagcaa gggcgaggag    900

ctgttcaccg gggtggtgcc catcctggtc gagctggacg gcgacgtaaa cggccacaag    960

ttcagcgtgt ccggcgaggg cgagggcgat gccacctacg gcaagctgac cctgaagttc   1020

atctgcacca ccggcaagct gcccgtgccc tggcccaccc tcgtgaccac cttcggctac   1080

ggcctgcagt gcttcgcccg ctaccccgac cacatgaagc agcacgactt cttcaagtcc   1140

gccatgcccg aaggctacgt ccaggagcgc accatcttct tcaaggacga cggcaactac   1200

aagacccgcg ccgaggtgaa gttcgagggc gacaccctgg tgaaccgcat cgagctgaag   1260

ggcatcgact tcaaggagga cggcaacatc ctggggcaca agctggagta caactacaac   1320

agccacaacg tctatatcat ggccgacaag cagaagaacg gcatcaaggt gaacttcaag   1380

atccgccaca acatcgagga cggcagcgtg cagctcgccg accactacca gcagaacacc   1440

cccatcggcg acggccccgt gctgctgccc gacaaccact acctgagcta ccagtccgcc   1500
```

```
ctgagcaaag accccaacga gaagcgcgat cacatggtcc tgctggagtt cgtgaccgcc   1560

gccgggatca ctctcggcat ggacgagctg tacaagccga ccccgccgta a            1611


<210> SEQ ID NO 6
<211> LENGTH: 1605
<212> TYPE: DNA
<213> ORGANISM: Artificial Sequence
<220> FEATURE:
<223> OTHER INFORMATION: humanized codon optimized sequence from
      Natronomonas pharaonis with the ER export signal added to the
      C-terminus

<400> SEQUENCE: 6

atgacagaga ccctgcctcc cgtgaccgag agtgccgtgg cccttcaagc cgaggttacc     60

caaagggagt tgttcgagtt cgtgctgaac gaccctttgc ttgcaagcag tctctatatc    120

aacatcgcac ttgcaggact gagtatactg ctgttcgttt ttatgacccg aggactcgat    180

gatccacggg caaaacttat tgctgtgtca accatccttg tgcctgtcgt cagcattgcc    240

tcctacactg gattggcgag cggcctgaca atttccgttc ttgaaatgcc agcgggccat    300

tttgcagaag gcagctcagt gatgctggga ggagaagagg tagatggtgt agtcaccatg    360

tggggacggt atctcacctg ggcactttcc acgcccatga ttctcctcgc tctgggtctc    420

ctggccggaa gcaatgctac aaagctcttc acagctatca ctttcgatat cgctatgtgc    480

gtgactggcc ttgccgcggc cctgactacc tcctcccacc tcatgagatg gttctggtac    540

gctatcagtt gtgcatgctt tctggtggtc ttgtatatcc tgctggtgga gtgggcacag    600

gacgccaaag ccgcgggaac cgctgacatg ttcaataccc tgaagctgtt gacagtagtg    660

atgtggctgg ggtatccaat tgtgtgggct cttggagtcg agggtatcgc ggtgttgccc    720

gttggggtga cgagctgggg atattctttc ctggatatcg tggcaaagta cattttcgca    780

ttcttgctcc tgaactatct gacgtcaaac gaatctgtcg tgtccggcag cattttggat    840

gttccatctg cttctgggac ccccggctgat gatgtgagca agggcgagga gctgttcacc    900

ggggtggtgc ccatcctggt cgagctggac ggcgacgtaa acggccacaa gttcagcgtg    960

tccggcgagg gcgagggcga tgccacctac ggcaagctga ccctgaagtt catctgcacc   1020

accggcaagc tgcccgtgcc ctggcccacc ctcgtgacca ccttcggcta cggcctgcag   1080

tgcttcgccc gctaccccga ccacatgaag cagcacgact tcttcaagtc cgccatgccc   1140

gaaggctacg tccaggagcg caccatcttc ttcaaggacg acggcaacta caagacccgc   1200

gccgaggtga agttcgaggg cgacaccctg gtgaaccgca tcgagctgaa gggcatcgac   1260

ttcaaggagg acggcaacat cctggggcac aagctggagt acaactacaa cagccacaac   1320

gtctatatca tggccgacaa gcagaagaac ggcatcaagg tgaacttcaa gatccgccac   1380

aacatcgagg acggcagcgt gcagctcgcc gaccactacc agcagaacac ccccatcggc   1440

gacggccccg tgctgctgcc cgacaaccac tacctgagct accagtccgc cctgagcaaa   1500

gaccccaacg agaagcgcga tcacatggtc ctgctggagt tcgtgaccgc cgccgggatc   1560

actctcggca tggacgagct gtacaaggtg ctgggcagcc tgtaa                   1605


<210> SEQ ID NO 7
<211> LENGTH: 1644
<212> TYPE: DNA
<213> ORGANISM: Artificial Sequence
<220> FEATURE:
<223> OTHER INFORMATION: humanized codon optimized sequence from
      Natronomonas pharaonis with a signal peptide (first 15aa) from
```

-continued

ChR2 (derived from Chlamydomonas reinhardtii) is added to the N-terminus

<400> SEQUENCE: 7

```
atggattatg gaggcgccct gagtgccgtt gggcgcgagc tgctatttac agagaccctg      60
cctcccgtga ccgagagtgc cgtggccctt caagccgagg ttacccaaag ggagttgttc     120
gagttcgtgc tgaacgaccc tttgcttgca agcagtctct atatcaacat cgcacttgca     180
ggactgagta tactgctgtt cgtttttatg acccgaggac tcgatgatcc acgggcaaaa     240
cttattgctg tgtcaaccat ccttgtgcct gtcgtcagca ttgcctccta cactggattg     300
gcgagcggcc tgacaatttc cgttcttgaa atgccagcgg gccattttgc agaaggcagc     360
tcagtgatgc tgggaggaga agaggtagat ggtgtagtca ccatgtgggg acggtatctc     420
acctgggcac tttccacgcc catgattctc ctcgctctgg gtctcctggc cggaagcaat     480
gctacaaagc tcttcacagc tatcactttc gatatcgcta tgtgcgtgac tggccttgcc     540
gcggccctga ctacctcctc ccacctcatg agatggttct ggtacgctat cagttgtgca     600
tgctttctgg tggtcttgta tatcctgctg gtggagtggg cacaggacgc caaagccgcg     660
ggaaccgctg acatgttcaa taccctgaag ctgttgacag tagtgatgtg gctggggtat     720
ccaattgtgt gggctcttgg agtcgagggt atcgcggtgt tgcccgttgg ggtgacgagc     780
tggggatatt ctttcctgga tatcgtggca aagtacattt tcgcattctt gctcctgaac     840
tatctgacgt caaacgaatc tgtcgtgtcc ggcagcattt tggatgttcc atctgcttct     900
gggaccccgg ctgatgatgc ggccgccgtg agcaagggcg aggagctgtt caccggggtg     960
gtgcccatcc tggtcgagct ggacggcgac gtaaacggcc acaagttcag cgtgtccggc    1020
gagggcgagg gcgatgccac ctacggcaag ctgaccctga agttcatctg caccaccggc    1080
aagctgcccg tgccctggcc caccctcgtg accaccttcg gctacggcct gcagtgcttc    1140
gcccgctacc ccgaccacat gaagcagcac gacttcttca agtccgccat gcccgaaggc    1200
tacgtccagg agcgcaccat cttcttcaag gacgacggca actacaagac ccgcgccgag    1260
gtgaagttcg agggcgacac cctggtgaac cgcatcgagc tgaagggcat cgacttcaag    1320
gaggacggca acatcctggg gcacaagctg gagtacaact acaacagcca caacgtctat    1380
atcatggccg acaagcagaa gaacggcatc aaggtgaact tcaagatccg ccacaacatc    1440
gaggacggca gcgtgcagct cgccgaccac taccagcaga acacccccat cggcgacggc    1500
cccgtgctgc tgcccgacaa ccactacctg agctaccagt ccgccctgag caaagacccc    1560
aacgagaagc gcgatcacat ggtcctgctg gagttcgtga ccgccgccgg gatcactctc    1620
ggcatggacg agctgtacaa gtaa                                           1644
```

<210> SEQ ID NO 8
<211> LENGTH: 1665
<212> TYPE: DNA
<213> ORGANISM: Artificial Sequence
<220> FEATURE:
<223> OTHER INFORMATION: humanized codon optimized sequence from Natronomonas pharaonis with a signal peptide (23aa) from nicotinic acetylcholine receptor is added to the N-terminus

<400> SEQUENCE: 8

```
atgggtcttc gtgctcttat gctttggctt cttgctgctg ctggtcttgt tcgtgaatct      60
cttcaaggta cagagaccct gcctcccgtg accgagagtg ccgtggccct tcaagccgag     120
gttacccaaa gggagttgtt cgagttcgtg ctgaacgacc ctttgcttgc aagcagtctc     180
```

-continued

```
tatatcaaca tcgcacttgc aggactgagt atactgctgt tcgtttttat gacccgagga    240

ctcgatgatc cacgggcaaa acttattgct gtgtcaacca tccttgtgcc tgtcgtcagc    300

attgcctcct acactggatt ggcgagcggc ctgacaattt ccgttcttga aatgccagcg    360

ggccattttg cagaaggcag ctcagtgatg ctgggaggag aagaggtaga tggtgtagtc    420

accatgtggg gacggtatct cacctgggca ctttccacgc ccatgattct cctcgctctg    480

ggtctcctgg ccggaagcaa tgctacaaag ctcttcacag ctatcacttt cgatatcgct    540

atgtgcgtga ctggccttgc cgcggccctg actacctcct cccacctcat gagatggttc    600

tggtacgcta tcagttgtgc atgctttctg gtggtcttgt atatcctgct ggtggagtgg    660

gcacaggacg ccaaagccgc gggaaccgct gacatgttca ataccctgaa gctgttgaca    720

gtagtgatgt ggctggggta tccaattgtg tgggctcttg gagtcgaggg tatcgcggtg    780

ttgcccgttg gggtgacgag ctggggatat tctttcctgg atatcgtggc aaagtacatt    840

ttcgcattct tgctcctgaa ctatctgacg tcaaacgaat ctgtcgtgtc cggcagcatt    900

ttggatgttc catctgcttc tgggaccccg gctgatgatg cggccgccgt gagcaagggc    960

gaggagctgt tcaccggggt ggtgcccatc ctggtcgagc tggacggcga cgtaaacggc   1020

cacaagttca gcgtgtccgg cgagggcgag ggcgatgcca cctacggcaa gctgaccctg   1080

aagttcatct gcaccaccgg caagctgccc gtgccctggc ccaccctcgt gaccaccttc   1140

ggctacggcc tgcagtgctt cgcccgctac cccgaccaca tgaagcagca cgacttcttc   1200

aagtccgcca tgcccgaagg ctacgtccag gagcgcacca tcttcttcaa ggacgacggc   1260

aactacaaga cccgcgccga ggtgaagttc gagggcgaca ccctggtgaa ccgcatcgag   1320

ctgaagggca tcgacttcaa ggaggacggc aacatcctgg ggcacaagct ggagtacaac   1380

tacaacagcc acaacgtcta tatcatggcc gacaagcaga agaacggcat caaggtgaac   1440

ttcaagatcc gccacaacat cgaggacggc agcgtgcagc tcgccgacca ctaccagcag   1500

aacaccccca tcggcgacgg ccccgtgctg ctgcccgaca accactacct gagctaccag   1560

tccgccctga gcaaagaccc caacgagaag cgcgatcaca tggtcctgct ggagttcgtg   1620

accgccgccg ggatcactct cggcatggac gagctgtaca agtaa                   1665
```

<210> SEQ ID NO 9
<211> LENGTH: 1605
<212> TYPE: DNA
<213> ORGANISM: Artificial Sequence
<220> FEATURE:
<223> OTHER INFORMATION: humanized codon optimized sequence from Natronomonas pharaonis with the PDZ binding motif VSNL added to the C-terminus

<400> SEQUENCE: 9

```
atgacagaga ccctgcctcc cgtgaccgag agtgccgtgg cccttcaagc cgaggttacc     60

caaagggagt tgttcgagtt cgtgctgaac gaccctttgc ttgcaagcag tctctatatc    120

aacatcgcac ttgcaggact gagtatactg ctgttcgttt ttatgacccg aggactcgat    180

gatccacggg caaaacttat tgctgtgtca accatccttg tgcctgtcgt cagcattgcc    240

tcctacactg gattggcgag cggcctgaca atttccgttc ttgaaatgcc agcgggccat    300

tttgcagaag gcagctcagt gatgctggga ggagaagagg tagatggtgt agtcaccatg    360

tggggacggt atctcacctg ggcactttcc acgcccatga ttctcctcgc tctgggtctc    420

ctggccggaa gcaatgctac aaagctcttc acagctatca ctttcgatat cgctatgtgc    480

gtgactggcc ttgccgcggc cctgactacc tcctcccacc tcatgagatg gttctggtac    540
```

```
gctatcagtt gtgcatgctt tctggtggtc ttgtatatcc tgctggtgga gtgggcacag    600

gacgccaaag ccgcgggaac cgctgacatg ttcaataccc tgaagctgtt gacagtagtg    660

atgtggctgg ggtatccaat tgtgtgggct cttggagtcg agggtatcgc ggtgttgccc    720

gttggggtga cgagctgggg atattctttc ctggatatcg tggcaaagta cattttcgca    780

ttcttgctcc tgaactatct gacgtcaaac gaatctgtcg tgtccggcag cattttggat    840

gttccatctg cttctgggac ccccggctgat gatatggtga gcaagggcga ggagctgttc    900

accggggtgg tgcccatcct ggtcgagctg gacggcgacg taaacggcca caagttcagc    960

gtgtccggcg agggcgaggg cgatgccacc tacggcaagc tgaccctgaa gttcatctgc   1020

accaccggca agctgcccgt gccctggccc accctcgtga ccaccttcgg ctacggcctg   1080

cagtgcttcg cccgctaccc cgaccacatg aagcagcacg acttcttcaa gtccgccatg   1140

cccgaaggct acgtccagga gcgcaccatc ttcttcaagg acgacggcaa ctacaagacc   1200

cgcgccgagg tgaagttcga gggcgacacc ctggtgaacc gcatcgagct gaagggcatc   1260

gacttcaagg aggacggcaa catcctgggg cacaagctgg agtacaacta caacagccac   1320

aacgtctata tcatggccga caagcagaag aacggcatca aggtgaactt caagatccgc   1380

cacaacatcg aggacggcag cgtgcagctc gccgaccact accagcagaa cacccccatc   1440

ggcgacggcc ccgtgctgct gcccgacaac cactacctga gctaccagtc cgccctgagc   1500

aaagacccca acgagaagcg cgatcacatg gtcctgctgg agttcgtgac cgccgccggg   1560

atcactctcg gcatggacga gctgtacaag gtgagcaacc tgtaa                   1605
```

<210> SEQ ID NO 10
<211> LENGTH: 1599
<212> TYPE: DNA
<213> ORGANISM: Artificial Sequence
<220> FEATURE:
<223> OTHER INFORMATION: humanized codon optimized sequence from Natronomonas pharaonis with a hybrid construct of the ER export signal added to the C-terminus and the signal peptide (23aa) from nicotinic acetylcholine receptor added to the N-terminus

<400> SEQUENCE: 10

```
atgacagaga ccctgcctcc cgtgaccgag agtgccgtgg cccttcaagc cgaggttacc     60

caaagggagt tgttcgagtt cgtgctgaac gaccctttgc ttgcaagcag tctctatatc    120

aacatcgcac ttgcaggact gagtatactg ctgttcgttt ttatgacccg aggactcgat    180

gatccacggg caaaacttat tgctgtgtca accatccttg tgcctgtcgt cagcattgcc    240

tcctacactg gattggcgag cggcctgaca atttccgttc ttgaaatgcc agcgggccat    300

tttgcagaag gcagctcagt gatgctggga ggagaagagg tagatggtgt agtcaccatg    360

tggggacggt atctcacctg ggcactttcc acgcccatga ttctcctcgc tctgggtctc    420

ctggccggaa gcaatgctac aaagctcttc acagctatca ctttcgatat cgctatgtgc    480

gtgactggcc ttgccgcggc cctgactacc tcctcccacc tcatgagatg gttctggtac    540

gctatcagtt gtgcatgctt tctggtggtc ttgtatatcc tgctggtgga gtgggcacag    600

gacgccaaag ccgcgggaac cgctgacatg ttcaataccc tgaagctgtt gacagtagtg    660

atgtggctgg ggtatccaat tgtgtgggct cttggagtcg agggtatcgc ggtgttgccc    720

gttggggtga cgagctgggg atattctttc ctggatatcg tggcaaagta cattttcgca    780

ttcttgctcc tgaactatct gacgtcaaac gaatctgtcg tgtccggcag cattttggat    840

gttccatctg cttctgggac ccccggctgat gatgcggccg ccgtgagcaa gggcgaggag    900
```

```
ctgttcaccg gggtggtgcc catcctggtc gagctggacg gcgacgtaaa cggccacaag    960

ttcagcgtgt ccggcgaggg cgagggcgat gccacctacg gcaagctgac cctgaagttc   1020

atctgcacca ccggcaagct gcccgtgccc tggcccaccc tcgtgaccac cttcggctac   1080

ggcctgcagt gcttcgcccg ctaccccgac cacatgaagc agcacgactt cttcaagtcc   1140

gccatgcccg aaggctacgt ccaggagcgc accatcttct tcaaggacga cggcaactac   1200

aagacccgcg ccgaggtgaa gttcgagggc gacaccctgg tgaaccgcat cgagctgaag   1260

ggcatcgact tcaaggagga cggcaacatc ctggggcaca agctggagta caactacaac   1320

agccacaacg tctatatcat ggccgacaag cagaagaacg gcatcaaggt gaacttcaag   1380

atccgccaca acatcgagga cggcagcgtg cagctcgccg accactacca gcagaacacc   1440

cccatcggcg acggccccgt gctgctgccc gacaaccact acctgagcta ccagtccgcc   1500

ctgagcaaag accccaacga gaagcgcgat cacatggtcc tgctggagtt cgtgaccgcc   1560

gccgggatca ctctcggcat ggacgagctg tacaagtaa                          1599


<210> SEQ ID NO 11
<211> LENGTH: 14
<212> TYPE: PRT
<213> ORGANISM: Artificial Sequence
<220> FEATURE:
<223> OTHER INFORMATION: Signal peptide from ChR2

<400> SEQUENCE: 11

Asp Tyr Gly Gly Ala Leu Ser Ala Val Gly Arg Glu Leu Leu
1               5                   10


<210> SEQ ID NO 12
<211> LENGTH: 23
<212> TYPE: PRT
<213> ORGANISM: Artificial Sequence
<220> FEATURE:
<223> OTHER INFORMATION: signal peptide from nicotinic acetylcholine
      receptor

<400> SEQUENCE: 12

Met Gly Leu Arg Ala Leu Met Leu Trp Leu Leu Ala Ala Ala Gly Leu
1               5                   10                  15

Val Arg Glu Ser Leu Gln Gly
            20


<210> SEQ ID NO 13
<211> LENGTH: 18
<212> TYPE: PRT
<213> ORGANISM: Artificial Sequence
<220> FEATURE:
<223> OTHER INFORMATION: signal peptide from nicotinic acetylcholine
      receptor

<400> SEQUENCE: 13

Met Arg Gly Thr Pro Leu Leu Leu Val Val Ser Leu Phe Ser Leu Leu
1               5                   10                  15

Gln Asp


<210> SEQ ID NO 14
<211> LENGTH: 4
<212> TYPE: PRT
<213> ORGANISM: Artificial Sequence
<220> FEATURE:
<223> OTHER INFORMATION: PDZ binding motif ETQZ
```

<400> SEQUENCE: 14

Glu Thr Gln Glx
1

<210> SEQ ID NO 15
<211> LENGTH: 4
<212> TYPE: PRT
<213> ORGANISM: Artificial Sequence
<220> FEATURE:
<223> OTHER INFORMATION: PTPP sequence

<400> SEQUENCE: 15

Pro Thr Pro Pro
1

<210> SEQ ID NO 16
<211> LENGTH: 5
<212> TYPE: PRT
<213> ORGANISM: Artificial Sequence
<220> FEATURE:
<223> OTHER INFORMATION: ER export signal VLGSL

<400> SEQUENCE: 16

Val Leu Gly Ser Leu
1 5

<210> SEQ ID NO 17
<211> LENGTH: 5
<212> TYPE: PRT
<213> ORGANISM: Artificial Sequence
<220> FEATURE:
<223> OTHER INFORMATION: ER export signal VXXSL
<220> FEATURE:
<221> NAME/KEY: misc_feature
<222> LOCATION: (2)..(3)
<223> OTHER INFORMATION: Xaa can be any naturally occurring amino acid

<400> SEQUENCE: 17

Val Xaa Xaa Ser Leu
1 5

<210> SEQ ID NO 18
<211> LENGTH: 6
<212> TYPE: PRT
<213> ORGANISM: Artificial Sequence
<220> FEATURE:
<223> OTHER INFORMATION: ER export signal FXYENE
<220> FEATURE:
<221> NAME/KEY: misc_feature
<222> LOCATION: (2)..(2)
<223> OTHER INFORMATION: Xaa can be any naturally occurring amino acid

<400> SEQUENCE: 18

Phe Xaa Tyr Glu Asn Glu
1 5

<210> SEQ ID NO 19
<211> LENGTH: 4
<212> TYPE: PRT
<213> ORGANISM: Artificial Sequence
<220> FEATURE:
<223> OTHER INFORMATION: PDZ binding motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)

<223> OTHER INFORMATION: Xaa can be any naturally occurring amino acid

<400> SEQUENCE: 19

Xaa Ser Xaa Val
1

<210> SEQ ID NO 20
<211> LENGTH: 4
<212> TYPE: PRT
<213> ORGANISM: Artificial Sequence
<220> FEATURE:
<223> OTHER INFORMATION: PDZ binding motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 20

Xaa Thr Xaa Val
1

<210> SEQ ID NO 21
<211> LENGTH: 4
<212> TYPE: PRT
<213> ORGANISM: Artificial Sequence
<220> FEATURE:
<223> OTHER INFORMATION: PDZ binding motif

<400> SEQUENCE: 21

Glu Thr Gln Val
1

<210> SEQ ID NO 22
<211> LENGTH: 4
<212> TYPE: PRT
<213> ORGANISM: Artificial Sequence
<220> FEATURE:
<223> OTHER INFORMATION: PDZ binding motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 22

Xaa Ser Xaa Leu
1

<210> SEQ ID NO 23
<211> LENGTH: 4
<212> TYPE: PRT
<213> ORGANISM: Artificial Sequence
<220> FEATURE:
<223> OTHER INFORMATION: PDZ binding motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 23

-continued

```
Xaa Thr Xaa Leu
1


<210> SEQ ID NO 24
<211> LENGTH: 4
<212> TYPE: PRT
<213> ORGANISM: Artificial Sequence
<220> FEATURE:
<223> OTHER INFORMATION: PDZ binding motif

<400> SEQUENCE: 24

Val Ser Asn Leu
1
```

METHOD FOR OPTICALLY CONTROLLING A NEURON WITH A MAMMALIAN CODON OPTIMIZED NUCLEOTIDE SEQUENCE THAT ENCODES A VARIANT OPSIN POLYPEPTIDE DERIVED FROM NATROMONAS PHARAONIS (NPHR)

RELATED PATENT DOCUMENTS

This application is a continuation of U.S. patent application Ser. No. 13/855,413, now U.S. Pat. No. 9,284,353, which is a continuation of U.S. patent application Ser. No. 13/208,419, filed Aug. 12, 2011, which is a continuation of U.S. patent application Ser. No. 12/041,628, filed Mar. 3, 2008, and claims benefit under 35 U.S. §119(e) of U.S. Provisional Application Ser. No. 60/904,303 filed on Mar. 1, 2007, which applications are incorporated by reference herein in their entirety.

FEDERALLY-SPONSORED RESEARCH OR DEVELOPMENT

This invention was made with Government support under contract OD000616 awarded by the National Institutes of Health. The Government has certain rights in this invention.

INCORPORATION-BY-REFERENCE OF MATERIAL SUBMITTED ELECTRONICALLY

Incorporated by reference in its entirety is a computer-readable nucleotide/amino acid sequence listing and identified as follows: One 27,705 Byte ASCII (Text) file named "stfd-165PA_ST25" created on Nov. 19, 2010.

FIELD OF THE INVENTION

The present invention relates generally to systems and approaches for stimulating target cells, and more particularly to using optics to stimulate the target cells.

BACKGROUND

The stimulation of various cells of the body has been used to produce a number of beneficial effects. One method of stimulation involves the use of electrodes to introduce an externally generated signal into cells. One problem faced by electrode-based brain stimulation techniques is the distributed nature of neurons responsible for a given mental process. Conversely, different types of neurons reside close to one another such that only certain cells in a given region of the brain are activated while performing a specific task. Alternatively stated, not only do heterogeneous nerve tracts move in parallel through tight spatial confines, but the cell bodies themselves may exist in mixed, sparsely embedded configurations. This distributed manner of processing seems to defy the best attempts to understand canonical order within the central nervous system (CNS), and makes neuromodulation a difficult therapeutic endeavor. This architecture of the brain poses a problem for electrode-based stimulation because electrodes are relatively indiscriminate with regards to the underlying physiology of the neurons that they stimulate. Instead, physical proximity of the electrode poles to the neuron is often the single largest determining factor as to which neurons will be stimulated. Accordingly, it is generally not feasible to absolutely restrict stimulation to a single class of neuron lasing electrodes.

Another issue with the use of electrodes for stimulation is that because electrode placement dictates which neurons will be stimulated, mechanical stability is frequently inadequate, and results in lead migration of the electrodes from the targeted area. Moreover, after a period of time within the body, electrode leads frequently become encapsulated with glial cells, raising the effective electrical resistance of the electrodes, and hence the electrical power delivery required to reach targeted cells. Compensatory increases in voltage, frequency or pulse width, however, may spread the electrical current and increase the unintended stimulation of additional cells.

Another method of stimulus uses photosensitive bio-molecular structures to stimulate target cells in response to light. For instance, light activated proteins can be used to control the flow of ions through cell membranes. By facilitating or inhibiting the flow of positive or negative ions through cell membranes, the cell can be briefly depolarized, depolarized and maintained in that state, or hyperpolarized. Neurons are an example of a type of cell that uses the electrical currents created by depolarization to generate communication signals (i.e., nerve impulses). Other electrically excitable cells include skeletal muscle, cardiac muscle, and endocrine cells. Neurons use rapid depolarization to transmit signals throughout the body and for various purposes, such as motor control (e.g., muscle contractions), sensory responses (e.g., touch, hearing, and other senses) and computational functions (e.g., brain functions). Thus, the control of the depolarization of cells can be beneficial for a number of different purposes, including (but not limited to) psychological therapy, muscle control and sensory functions.

SUMMARY

The claimed invention is directed to photosensitive bio-molecular structures and related methods. The present invention is exemplified in a number of implementations and applications, some of which are summarized below.

According to one example embodiment of the present invention, an implantable arrangement is implemented having a light-generation device for generating light. The arrangement also has a biological portion that modifies target cells for stimulation in response to light generated by the light-generation means in vivo.

According to another example embodiment of the present invention, target cells are stimulated using an implantable arrangement. The arrangement includes an electrical light-generation means for generating light and a biological portion. The biological portion has a photosensitive bio-molecular arrangement that responds to the generated light by stimulating target cells in vivo. Stimulation may be manifest as either up-regulation, or down-regulation of activity at the target.

According to another example embodiment of the present invention, an implantable device delivers gene transfer vector, such as a virus, which induces expression of photosensitive bio-molecular membrane proteins. The device has a light generator, responsive to (for example, charged by or triggered by) an external signal, to generate light and a biological arrangement that includes the photosensitive bio-molecular protein that responds to the generated light by interacting with target cells in vivo. In this manner, the electronic portions of the device may be used to optically stimulate target cells. Stimulation may be manifested as either upregulation (e.g., increased neuronal firing activity), or downregulation (e.g., neuronal hyperpolarization, or alternatively, chronic depolarization) of activity at the target.

According to another example embodiment of the present invention, a method is implemented for stimulating target cells using photosensitive proteins that bind with the target cells. The method includes a step of implanting the photosensitive proteins and a light generating device near the target cells. The light generating device is activated and the photosensitive protein stimulates the target cells in response to the generated light.

Applications include those associated with any population of electrically-excitable cells, including neurons, skeletal, cardiac, and smooth muscle cells, and insulin-secreting pancreatic beta cells. Major diseases with altered excitation-effector coupling include heart failure, muscular dystrophies, diabetes, pain, cerebral palsy, paralysis, depression, and schizophrenia. Accordingly, the present invention has utility in the treatment of a wide spectrum of medical conditions, from Parkinson's disease and brain injuries to cardiac dysrhythmias, to diabetes, and muscle spasm.

According to other example embodiments of the present invention, methods for generating an inhibitory neuron-current flow involve, in a neuron, engineering a protein that responds to light by producing an inhibitory current to dissuade depolarization of the neuron. In one such method, the protein is halorhodopsin-based and in another method the protein is an inhibitory protein that uses an endogenous cofactor.

According to another example embodiment of the present invention, a method for controlling action potential of a neuron involves the following steps: engineering a first light responsive protein in the neuron; producing, in response to light, an inhibitory current in the neuron that is generated from the first light responsive protein; engineering a second light responsive protein in the neuron; and producing, in response to light, an excitation current in the neuron from the second light responsive protein.

In another method for controlling a voltage level across a cell membrane of a cell, the method comprises: engineering a first light responsive protein in the cell; measuring the voltage level across the cell membrane; and producing, in response to light of a first wavelength and using the first light responsive protein, a current across the cell membrane that is responsive to the measured voltage level.

According to another example embodiment of the present invention, a method for generating an inhibitory-current flow in neurons is implemented. The method includes in a neuron, engineering an inhibitory protein that responds to light by producing an inhibitory current to dissuade depolarization of the neuron, wherein the inhibitory protein does not have the sequence as set forth in GenBank accession number EF474018 and uses an endogenous cofactor to produce the inhibitory current.

According to another example embodiment of the present invention, a method for generating an inhibitory-current flow in neurons is implemented. The method includes in a neuron, engineering a protein that responds to light by producing an inhibitory current to dissuade depolarization of the neuron, wherein the protein uses an endogenous cofactor and results in a toxicity of the engineered neuron that is less than about 75%.

According to another example embodiment of the present invention, a method for controlling action potential of a neuron is implemented. A first light responsive protein is engineered in the neuron. The first light responsive protein does not have the sequence as set forth in GenBank accession number EF474018 and uses an endogenous cofactor to produce the inhibitory current. In response to light, an inhibitory current is produced in the neuron, the current generated from the first light responsive protein. A second light responsive protein is engineered in the neuron. In response to light, an excitation current is produced in the neuron from the second light responsive protein.

According to another example embodiment of the present invention, a method for controlling a voltage level across a cell membrane of a cell is implemented. A first light responsive protein is engineered in the cell. The voltage level across the cell membrane is measured. Light of a first wavelength is generated in response to the measured voltage level. In response to light of a first wavelength and using the first light responsive protein, a first current is produced across the cell membrane that.

According to another example embodiment of the present invention, system controls an action potential of a neuron in vivo. A delivery device introduces a light responsive protein to the neuron, wherein the light responsive protein produces an inhibitory current and is not the sequence as set forth in GenBank accession number EF474018. A light source generates light for stimulating the light responsive protein. A control device controls the generation of light by the light source.

According to another example embodiment of the present invention, a method for treatment of a disorder is implemented. In a group of neurons associated with the disorder, inhibitory proteins are engineered that use an endogenous cofactor to respond to light by producing an inhibitory current to dissuade depolarization of the neurons, wherein the engineered group of neurons has a toxicity of less than about 75%. The neurons are exposed to light, thereby dissuading depolarization of the neurons.

According to an example embodiment of the present invention, a light-responsive opsin is provided for use in therapy. The opsin can be a NpHR-based molecule for use in therapy wherein the molecule is capable of responding to light by producing an inhibitory current to dissuade depolarization of a neuron and wherein the protein/molecule is capable of using an endogenous cofactor to produce the inhibitory current and manifests a toxicity level that is less than 75%, at a high expression level.

According to an example embodiment of the present invention, a light-responsive opsin is used in treating neurological diseases. The opsin can include a nucleic acid molecule comprising a nucleotide sequence encoding a NpHR based protein for use in the treatment of CNS disorders wherein said protein is capable of responding to light by producing an inhibitory current to dissuade depolarization of a neuron using an endogenous cofactor to produce the inhibitory current and manifests a toxicity level that is less than 50%, at a high expression level.

According to another example embodiment, a light-responsive opsin is used in the manufacture of a medicament for the treatment of neurological diseases. For example, an NpHR-based protein in the manufacture of a medicament for the treatment of CNS disorders wherein the said protein is capable of responding to light by producing an inhibitory current to dissuade depolarization of a neuron and is capable of using an endogenous cofactor to produce the inhibitory current and manifests a toxicity level that is less than 75%, at a high expression level.

According to another example embodiment, kit is provided for administering treatment. The kit includes, for example a product containing a first light-responsive opsin and a second-light responsive opsin as a combined preparation for simultaneous, separate or sequential use in the treatment of neurological diseases.

According to another example embodiment, a transgenic animal is produced with a light-responsive opsin expressed in one or more cells.

According to another example embodiment, cells are modified, in a live animal, using light-responsive opsins. The animal is sacrificed and the modified cells are removed for study.

Other aspects and embodiments are directed to systems, methods, kits, compositions of matter and molecules for ion pumps or for controlling inhibitory currents in a cell (e.g., in in vivo and in vitro environments).

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings, in which:

FIGS. 1A, 1B, 1C, 1D, 1E, 1F, 1G, 1H, 1I, 1J, 1K, 1L, 1M, 1N and 1O show experimental results that are consistent with an example embodiment of the present invention;

Figure 1A:
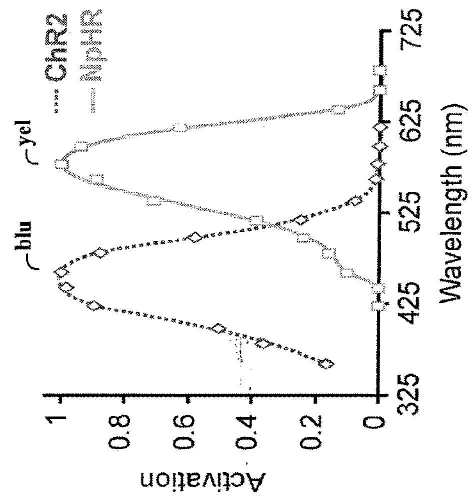

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be useful for facilitating practical application of a variety of photosensitive bio-molecular structures, and the invention has been found to be particularly suited for use in arrangements and methods dealing with cellular membrane voltage control and stimulation. While the present invention is not necessarily limited to such applications, various aspects of the invention may be appreciated through a discussion of various examples using this context.

Consistent with one example embodiment of the present invention, a light-responsive protein/molecule is engineered in a cell. The protein affects a flow of ions across the cell membrane in response to light. This change in ion flow creates a corresponding change in the electrical properties of the cells including, for example, the voltage and current flow across the cell membrane. In one instance, the protein functions in vivo using an endogenous cofactor to modify ion flow across the cell membrane. In another instance, the protein changes the voltage across the cell membrane so as to dissuade action potential firing in the cell. In yet another instance, the protein is capable of changing the electrical properties of the cell within several milliseconds of the light being introduced. For details on delivery of such proteins, reference may be made to U.S. patent application Ser. No. 11/459,636 filed on Jul. 24, 2006 and entitled "Light-Activated Cation Channel and Uses Thereof", which is fully incorporated herein by reference.

Consistent with a more specific example embodiment of the present invention a protein, NpHR, from *Natronomonas pharaonis* is used for temporally-precise optical inhibition of neural activity. NpHR allows for selective inhibition of single action potentials within rapid spike trains and sustained blockade of spiking over many minutes. The action spectrum of NpHR is strongly red-shifted relative to ChannelRhodopsin-2 (ChR2) (derived from *Chlamydomonas reinhardtii*) but operates at similar light power, and NpHR functions in mammals without exogenous cofactors. In one instance, both NpHR and ChR2 can be expressed in the target cells. Likewise, NpHR and ChR2 can be targeted to *C. elegans* muscle and cholinergic motoneurons to control locomotion bidirectionally. In this regard, NpHR and ChR2 form an optogenetic system for multimodal, high-speed, genetically-targeted, all-optical interrogation of living neural circuits.

Certain aspects of the present invention are based on the identification and development of an archaeal light-driven chloride pump, such as halorhodopsin (NpHR), from *Natronomonas pharaonis*, for temporally-precise optical inhibition of neural activity. The pump allows both knockout of single action potentials within rapid spike trains and sustained blockade of spiking over many minutes, and it operates at similar light power compared to ChR2 but with a strongly red-shifted action spectrum. The NpHR pump also functions in mammals without exogenous cofactors.

According to other example embodiments of the present invention, methods for generating an inhibitory neuron-current flow involve, in a neuron, engineering a protein that responds to light by producing an inhibitory current to dissuade depolarization of the neuron. In one such method, the protein is halorhodopsin-based and in another method the protein is an inhibitory protein that uses an endogenous cofactor.

In another example embodiment, a method for controlling action potential of a neuron involves the following steps: engineering a first light responsive protein in the neuron; producing, in response to light, an inhibitory current in the neuron and from the first light responsive protein; engineering a second light responsive protein in the neuron; and producing, in response to light, an excitation current in the neuron from the second light responsive protein.

Another embodiment involves method for controlling a voltage level across a cell membrane of a cell, the method includes: engineering a first light responsive protein in the cell; measuring the voltage level across the cell membrane; and producing, in response to light of a first wavelength and using the first light responsive protein, a current across the cell membrane that is responsive to the measured voltage level.

Another aspect of the present invention is directed to a system for controlling an action potential of a neuron in vivo. The system includes a delivery device, a light source, and a control device. The delivery device introduces a light responsive protein to the neuron, with the light responsive protein producing an inhibitory current. The light source generates light for stimulating the light responsive protein, and the control device controls the generation of light by the light source.

In more detailed embodiments, such a system is further adapted such that the delivery device introduces the light responsive protein by one of transfection, transduction and microinjection, and/or such that the light source introduces light to the neuron via one of an implantable light generator and fiber-optics.

Another aspect of the present invention is directed to a method for treatment of a disorder. The method targets a group of neurons associated with the disorder; and in this group, the method includes engineering an inhibitory protein that uses an endogenous cofactor to respond to light by producing an inhibitory current to dissuade depolarization of the neurons, and exposing the neurons to light, thereby dissuading depolarization of the neurons.

According to yet another aspect of the present invention is directed to identifying and developing an archaeal light-driven chloride pump, such as halorhodopsin (NpHR), from *Natronomonas* pharaonic, for temporally-precise optical inhibition of neural activity. The pump allows both knockout of single action potentials within rapid spike trains and sustained blockade of spiking over many minutes, and it operates at similar light power compared to ChR2 but with a strongly red-shifted action spectrum. The NpHR pump also functions in mammals without exogenous cofactors.

More detailed embodiments expand on such techniques. For instance, another aspect of the present invention co-expresses NpHR and ChR2 in the species (e.g., a mouse and *C. elegans*). Also, NpHR and ChR2 are integrated with calcium imaging in acute mammalian brain slices for bidirectional optical modulation and readout of neural activity. Likewise, NpHR and ChR2 can be targeted to *C. elegans* muscle and cholinergic motoneurons to control locomotion bidirectionally. Together NpHR and ChR2 can be used as a complete and complementary opto-genetic system for multimodal, high-speed, genetically-targeted, all-optical interrogation of living neural circuits.

In addition to NpHR and ChR2, there are a number of channelrhodopsins, halorhodopsins, and microbial opsins that can be engineered to optically regulate ion flux or second messengers within cells. Various embodiments of the invention include codon-optimized, mutated, truncated, fusion proteins, targeted versions, or otherwise modified versions of such ion optical regulators. Thus, ChR2 and NpHR (e.g., GenBank accession number is EF474018 for the 'mammalianized' NpHR sequence and EF474017 for the 'mammalianized' ChR2(1-315) sequence) are used as representative of a number of different embodiments. Discussions specifically identifying ChR2 and NpHR are not meant to limit the invention to such specific examples of optical regulators. For further details regarding the above mentioned sequences reference can be made to "Multimodal fast optical interrogation of neural circuitry" by Feng Zhang, et al, Nature (Apr. 5, 2007) Vol. 446: 633-639, which is fully incorporated herein by reference.

Consistent with an example embodiment of the present invention, a method is implemented for stimulating target cells in vivo using gene transfer vectors (for example, viruses) capable of inducing photosensitive ion channel growth (for example, ChR2 ion channels). The vectors can be implanted in the body.

Consistent with a particular embodiment of the present invention, a protein is introduced to one or more target cells. When introduced into a cell, the protein changes the potential of the cell in response to light having a certain frequency. This may result in a change in resting potential that can be used to control (dissuade) action potential firing. In a specific example, the protein is a halorhodopsin that acts as a membrane pump for transferring charge across the cell membrane in response to light. Membrane pumps are energy transducers which use electromagnetic or chemical bond energy for translocation of specific ions across the membrane. For further information regarding halorhodopsin membrane pumps reference can be made to "Halorhodopsin Is a Light-driven Chloride Pump" by Brigitte Schobert, et al, The Journal of Biological Chemistry Vol. 257, No. 17. Sep. 10, 1982, pp. 10306-10313, which is fully incorporated herein by reference.

The protein dissuades firing of the action potential by moving the potential of the cell away from the action potential trigger level for the cell. In many neurons, this means that the protein increases the negative voltage seen across the cell membrane. In a specific instance, the protein acts as a chloride ion pump that actively transfers negatively charged chloride ions into the cell. In this manner, the protein generates an inhibitory current across the cell membrane. More specifically, the protein responds to light by lowering the voltage across the cell thereby decreasing the probability that an action potential or depolarization will occur.

As used herein, stimulation of a target cell is generally used to describe modification of properties of the cell. For instance, the stimulus of a target cell may result in a change in the properties of the cell membrane that can lead to the depolarization or polarization of the target cell. In a particular instance, the target cell is a neuron and the stimulus affects the transmission of impulses by facilitating or inhibiting the generation of impulses by the neuron.

As discussed above, one embodiment of the present invention involves the use of an optically responsive ion-pump that is expressed in a cell. In a particular instance, the cell is either a neural cell or a stem cell. A specific embodiment involves in vivo animal cells expressing the ion-pump. Certain aspects of the present invention are based on the identification and development of an archaeal light-driven chloride pump, such as halorhodopsin (NpHR), from *Natronomonas* pharaonic, for temporally-precise optical inhibition of neural activity. The pump allows both knockout of single action potentials within rapid spike trains and sustained blockade of spiking over many minutes, and it operates at similar light power compared to ChR2 but with a strongly red-shifted action spectrum. The NpHR pump also functions in mammals without exogenous cofactors.

According to an example embodiment of the present invention, an optically responsive ion-pump and/or channel is expressed in one or more stem cells, progenitor cells, or progeny of stem or progenitor cells. Optical stimulation is used to activate expressed pumps/channels. The activation can be used to control the ion concentrations (e.g., chloride, calcium, sodium, and potassium) in the cells. This can be particularly useful for affecting the survival, proliferation, differentiation, de-differentiation, or lack of differentiation in the cells. Thus, optical stimulus is implemented to provide control over the (maturation) of stem or progenitor cells.

In a particular embodiment, optically-controlled stimulus patterns are applied to the stem or progenitor cells over a period of hours or days. For further details regarding the effects of membrane potentials and ion concentrations on such cells reference can be made to "Excitation-Neurogenesis Coupling in Adult Neural Stem/Progenitor Cells" by Karl Deisseroth, et al, Neuron (May 27, 2004) Neuron, Vol. 42, 535-552 and to U.S. Patent Publication No. 20050267011 (U.S. patent application Ser. No. 11/134,720) entitled "Coupling of Excitation and Neurogenesis in Neural Stem/Progenitor Cells" to Deisseroth et al and filed on May 19, 2005, which are each fully incorporated herein by reference.

In a particular embodiment, a method of driving differentiation in cells is implemented. The cells are caused to express light-activated NpHR-based protein. The cells are exposed to light to activate the NpHR-based protein. The activation drives differentiation of the exposed cell or the progeny of the exposed cell.

In another embodiment, the cells comprise stem cells.

Two exemplary ion pumps originate from two strains of archaea, *Halobacterium salinarum* (HsHR) and *Natronomonas pharaonis* (NpHR). Illumination of HsHR or NpHR-expressing oocytes leads to rapid outward currents. Both HsHR and NpHR have excitation maxima near 580 nm as shown in FIG. 1A. Specifically, FIG. 1A shows the action spectrum of NpHR when measured in *Xenopus* oocytes using a Xenon short arc lamp and narrowbandwidth 20 nm filters, which is red-shifted from the known ChR2 maximum of ~460 nm. This spectral separation allows for ChR2 and an HR to be activated independently or in synchrony to effect bidirectional optical modulation of membrane potential.

Figure 1B:
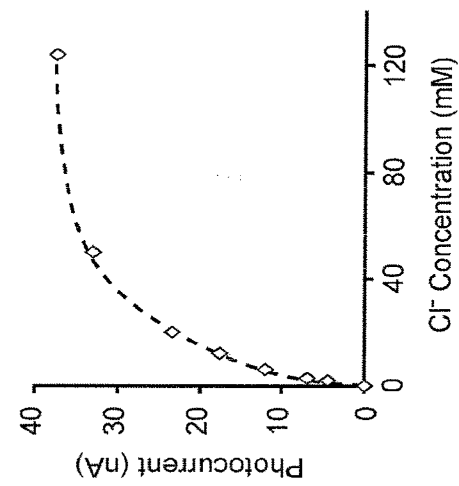

In an experimental test, HsHR was found to have a lower extracellular Cl− affinity than NpHR (Km,NpHR=16 mM in FIG. 1B, Km,HsHR=32 mM) and measured currents displayed rapid rundown at low extracellular [Cl−] that did not fully recover in darkness. The influence of cytoplasmic [Cl−] on HR pump currents was studied using excised giant patches. HR pump currents were not influenced by cytoplasmic [Cl−](from 0 to 124 mM), indicating a very low affinity for Cl− on the cytoplasmic side where Cl− ions are released, as expected since HR-mediated chloride pumping can achieve molar concentrations of cytoplasmic Cl−. The pump current exhibits more or less linear voltage dependence, and Cl− current is robust for both HRs across all physiological voltage regimes.

Figure 1C:
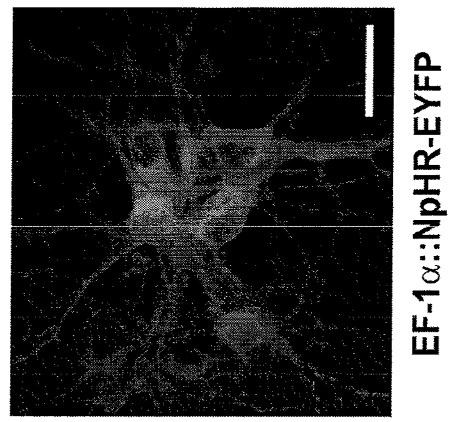
Figure 1H:
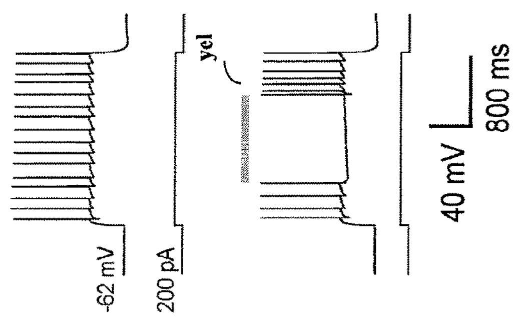
Figure 1G:
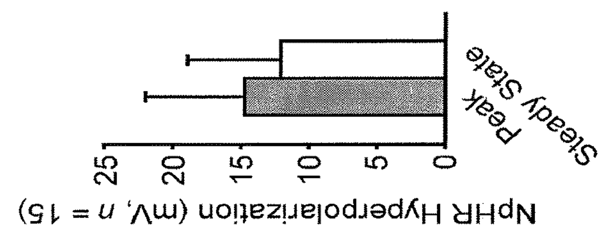
Figure 1F:
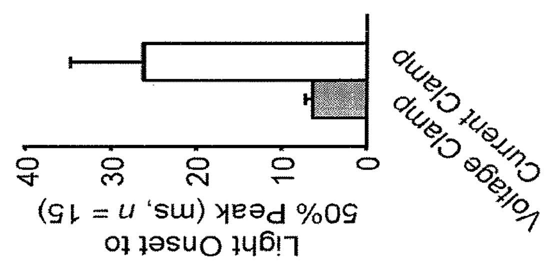
Figure 1E:
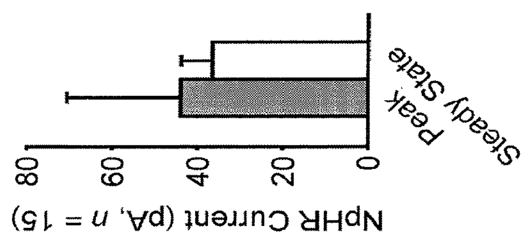
Figure 1D:
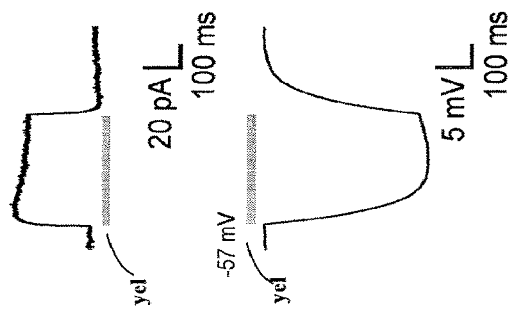
Figure 1O:
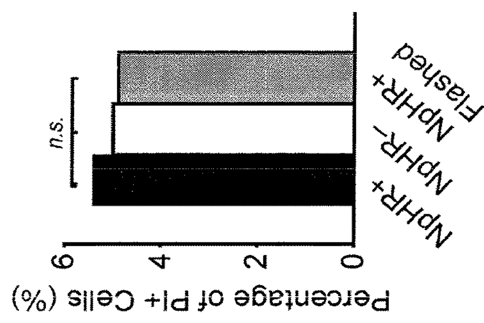

In one instance, a mammalian codon-optimized NpHR gene fused with enhanced yellow fluorescent protein (NpHR-EYFP) was introduced into cultured rat hippocampal CA3/CA1 neurons using lentiviruses carrying the ubiquitous EF-1α promoter (EF1 α::NpHR-EYFP). Cells expressing NpHR-EYFP exhibited robust expression for weeks after infection (FIG. 1C). In voltage clamp, illumination of NpHR-EYFP cells with yellow light (bandwidth 573-613 nm via Semrock filter FF01-593/40-25; 300 W xenon lamp) induced rapid outward currents (FIG. 1D, top) with a peak level of 43.8±25.9 pA and a steady-state level of 36.4±24.4 pA (mean±s.d. reported throughout this paper, n=15; FIG. 1E). The relatively small difference between the peak and steady-state currents is believed to be indicative of rare deprotonation of the NpHR Schiff base during the pump cycle 24. The rise time from light onset to 50% of the peak current is consistent across all cells (6.0±1.0 ms; FIG. 1F) with rise and decay time constants of Ton=6.1±2.1 ms and Toff=6.9±2.2 ms respectively. Light-evoked responses were never seen in cells expressing EYFP alone. In current clamp, NpHR-EYFP neurons exhibited light-evoked hyperpolarization (FIG. 1D; bottom) with an average peak of 14.7±6.9 mV and a steady-state of 12.1±6.6 mV (FIG. 1G). The delay from light onset to 50% of hyperpolarization peak was 26.0±8.6 ms (FIG. 1F) and the rise and decay time constants were Ton=35.6±15.1 ms and Toff=40.5±25.3 ms respectively. To test whether NpHR-mediated hyperpolarization could inhibit neuronal firing, current-clamped neurons were injected with a 200 pA current step for 2 s to evoke robust spike firing; concurrent light delivery abolished the evoked activity (FIG. 1H).

Images of NpHR-EYFP and ChR2-mCherry co-expressed in cultured hippocampal neurons were taken (FIG. 1I). NpHR function was probed using cell-attached recordings with ChR2 photostimulation to drive reliable spike trains. Indeed, whereas trains of blue light pulses (see "blu" in FIG. 1J) were able to evoke action potentials, concomitant yellow light illumination (see "yel" in FIG. 1J) abolished spike firing in both cell-attached and subsequent whole-cell recoding modes (FIG. 1J). After achieving the whole-cell configuration, voltage-clamp recording showed that independent exposure to yellow or blue light led to outward or inward photocurrents respectively (FIG. 1K), further confirming that ChR2 and NpHR can be combined to achieve bidirectional, independently addressable modulation of membrane potential in the same neuron. Further confirming that NpHR inhibitory function does not require a specific pipette chloride concentration under these recording conditions, it was found that NpHR-mediated inhibition is robust across a range of relevant whole-cell pipette chloride concentrations (4-25 mM) and physiologically negative resting potentials, as expected from the fact that NpHR is designed to deliver chloride ions to molar levels in the archaeal intracellular milieu.

Figure 1N:
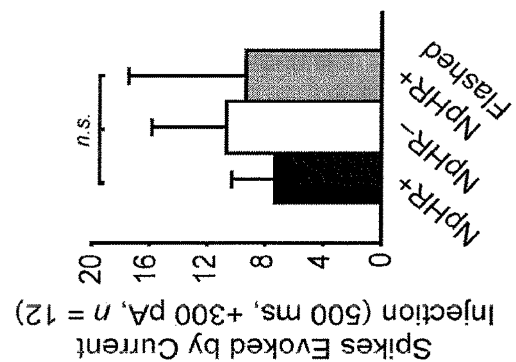
Figure 1M:
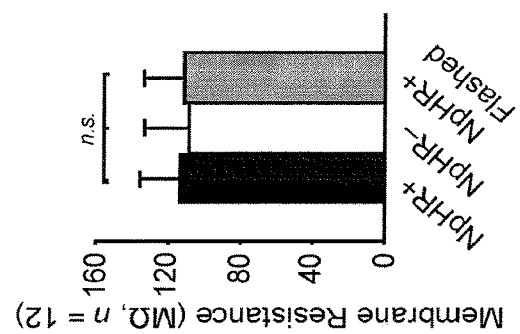
Figure 1L:
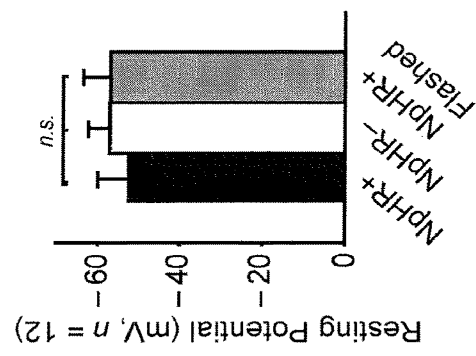

Extensive controls were conducted to test whether heterologous expression of NpHR in neurons would alter the membrane properties or survival of neurons. Lentiviral expression of NpHR for at least 2 weeks did not alter neuronal resting potential (−53.1±6.3 mV for NpHR+ cells, −57.0±4.8 mV for NpHR− cells, and −56.7±5.7 mV for NpHR+ cells exposed to yellow light for 10 min followed by a delay period of 1 day; FIG. 1L, n=12 each) or membrane resistance (114.5±34.1 MΩ for NpHR+ cells, 108.9±20.1 MΩ for NpHR− cells, and 111.4±23 MΩ for the light-exposed NpHR+ cells; FIG. 1M, n=12 each). These electrical measurements indicated that NpHR has little basal electrical activity or passive current-shunting ability and can be acceptable regarding cell health.

The dynamic electrical properties of neurons were tested with and without NpHR. There was no significant difference in the number of spikes evoked by 500 ms current injection of 300 pA (7.5±2.8 for NpHR+ neurons, 10.7±7.9 for NpHR− neurons, and 9.3±5.1 for the light-exposed NpHR+ neurons; FIG. 1N).

To assess cell survivability, both live NpHR+ neurons (with and without light exposure) and NpHR− neurons were stained with the membrane-impermeant DNA-binding dye propidium iodide to assess cell survival. NpHR expression did not affect the percentage of neurons that took up propidium iodide (13/240 for NpHR+ cells, 7/141 for NpHR− cells, and 10/205 for the light-exposed NpHR+ cells; FIG. 1M, P>0.999 by $X^2$ test). These experiments indicated that NpHR expression does not significantly affect the health or basal electrical properties of neurons.

The tunability of NpHR efficacy with different intensities of delivered light was measured using a 200 pA current step that drove reliable action potential trains. It was discovered that maximal light intensity of 21.7 mW/mm2 under a 40×, 0.8 NA water-immersion objective inhibited 98.2±3.7% of the spikes.

Figures 2A, 2B, 2C:
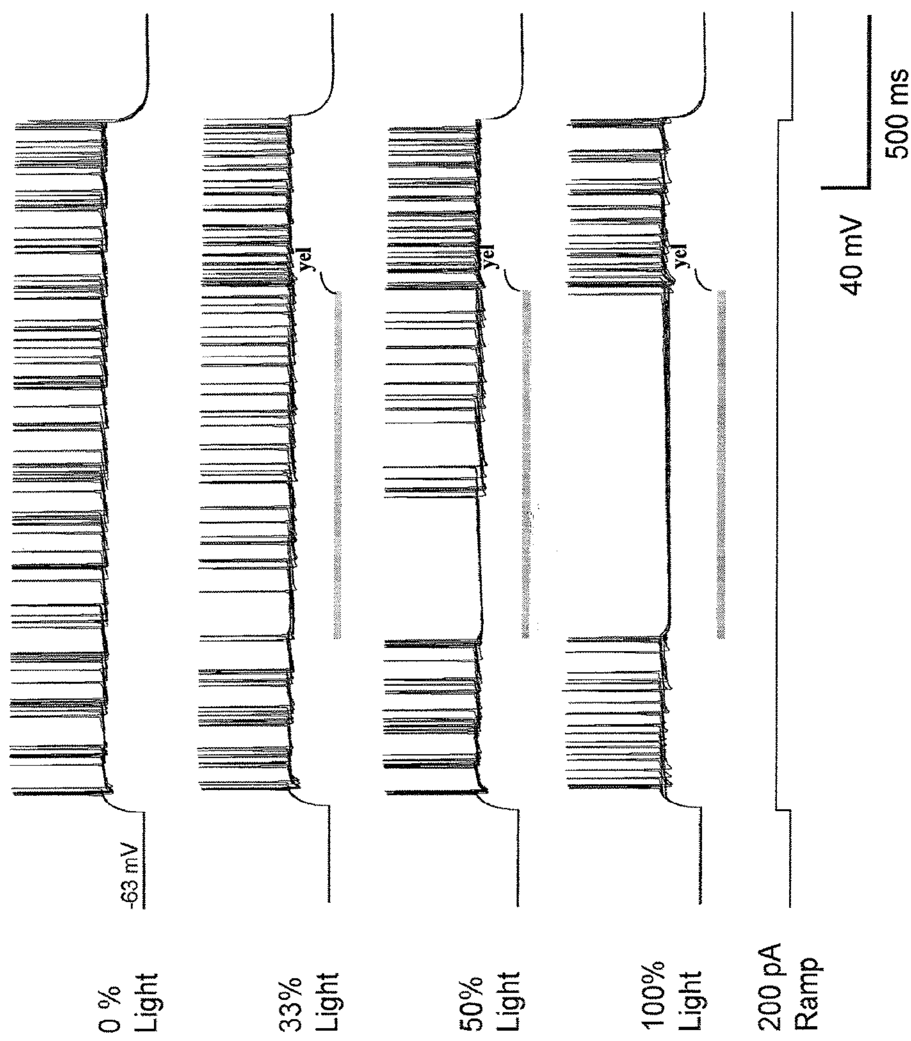
FIGS. 2A, 2B, 2C, 2D, 2E and 2F show experimental results that are consistent with an example embodiment of the present invention.

Using a 200 pA current step to drive reliable action potential trains, a maximal light intensity of 21.7 $mW/mm^2$ under 40×, 0.8 NA water-immersion objective inhibited 98.2±3.7% of spikes (FIGS. 2A and 2B). Using 33% or 50% of the full light intensity inhibited 74.9±22.2% and 87.3±13.5% of spikes, respectively (FIG. 2B). FIG. 2C shows that with steady current injection, lower intensities of light were effective for a shorter period of time; the delays from light onset to the first escaped spike under 33%, 50% and 100% light intensity were 533.65±388.2 ms, 757.5±235.5 ms, and 990.5±19.1 ms, respectively. Therefore inhibition is likely to be more effective early in the light pulse, presumably due to the slight inactivation of NpHR. Except where otherwise noted, the remaining experiments were conducted with 21.7 mW/mm2 yellow light delivered to the neurons.

Figure 2D:
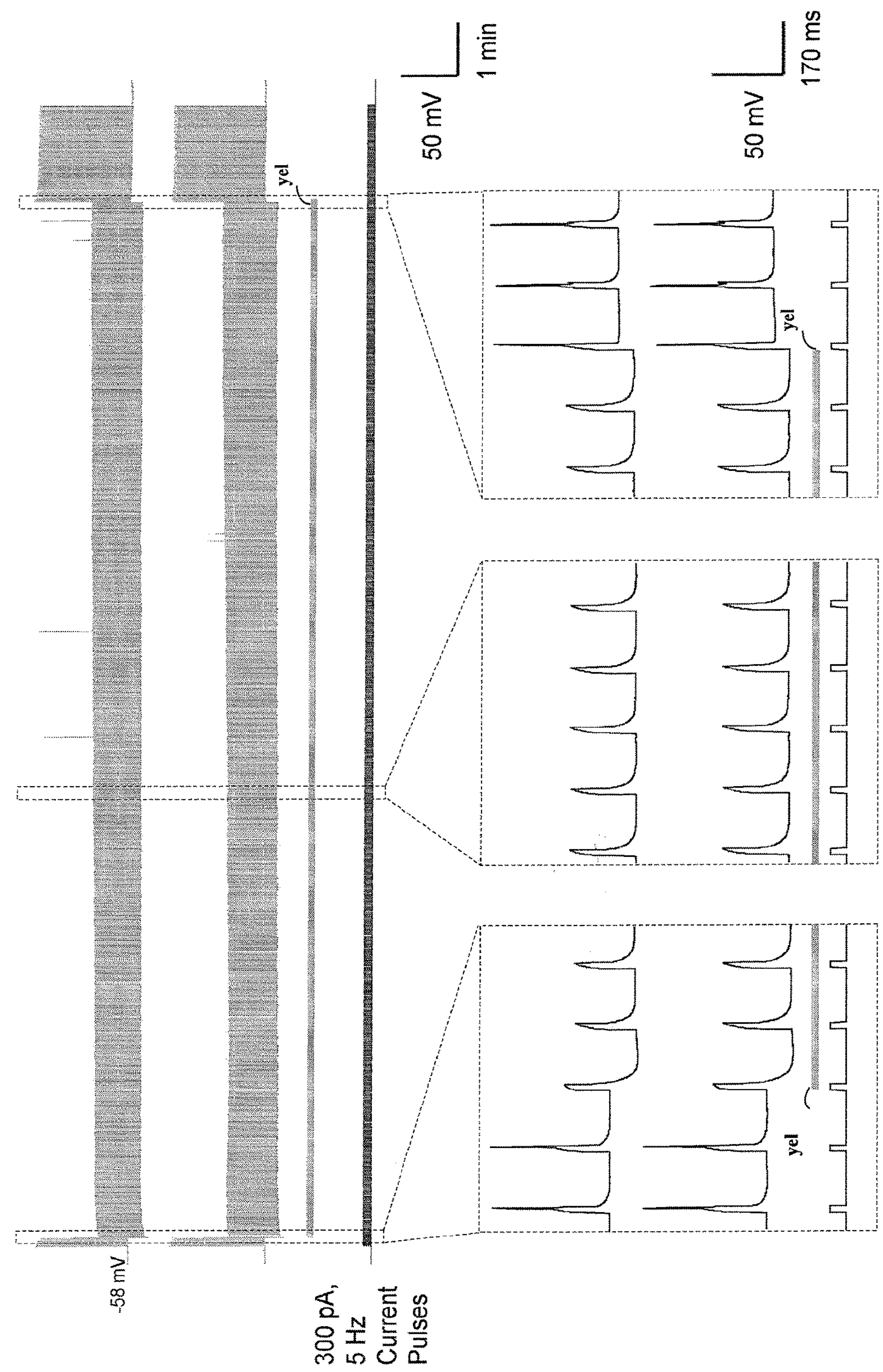
Figure 2F:
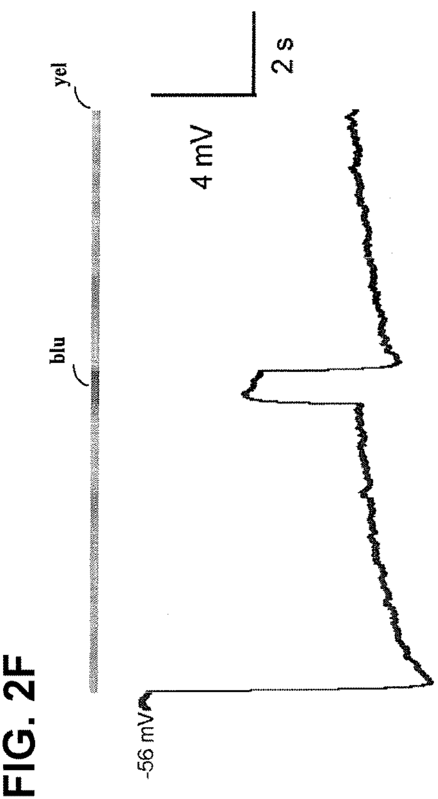
Figure 2E:
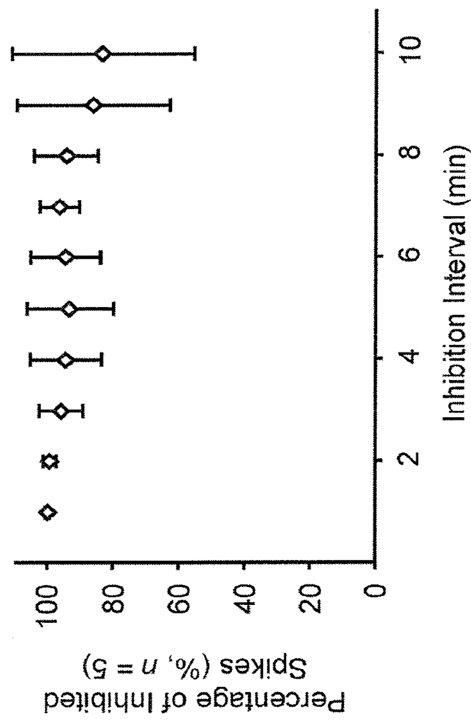

Using trains of brief current pulses to generate spike trains, NpHR was tested for mediation of both long-term inhibition (to emulate lesions on the timescale of seconds to minutes) and short-term inhibition (to modify spike firing on the millisecond timescale). For long-term inhibition NpHR was tested over 10 min by injecting 300 pA current pulses at 5 Hz to drive steady action potential firing. Concurrent yellow light was delivered continuously for 10 minutes. NpHR mediated inhibition of spike trains remained effective over many minutes as shown by FIG. 2D. 99.0±1.9% of spikes were inhibited within the first two minutes while over 90% of spikes were inhibited for up to 8 minutes as shown in FIG. 2E, with n=5. The slight decrease in efficacy is likely due to accumulation of non-functional NpHRs with a deprotonated Schiff base over long periods of light exposure. While natural reprotonation of the Schiff base is slow, any non-functional NpHRs can be readily and quickly restored via brief illumination with blue light as shown by FIG. 2F.

Figure 3A:
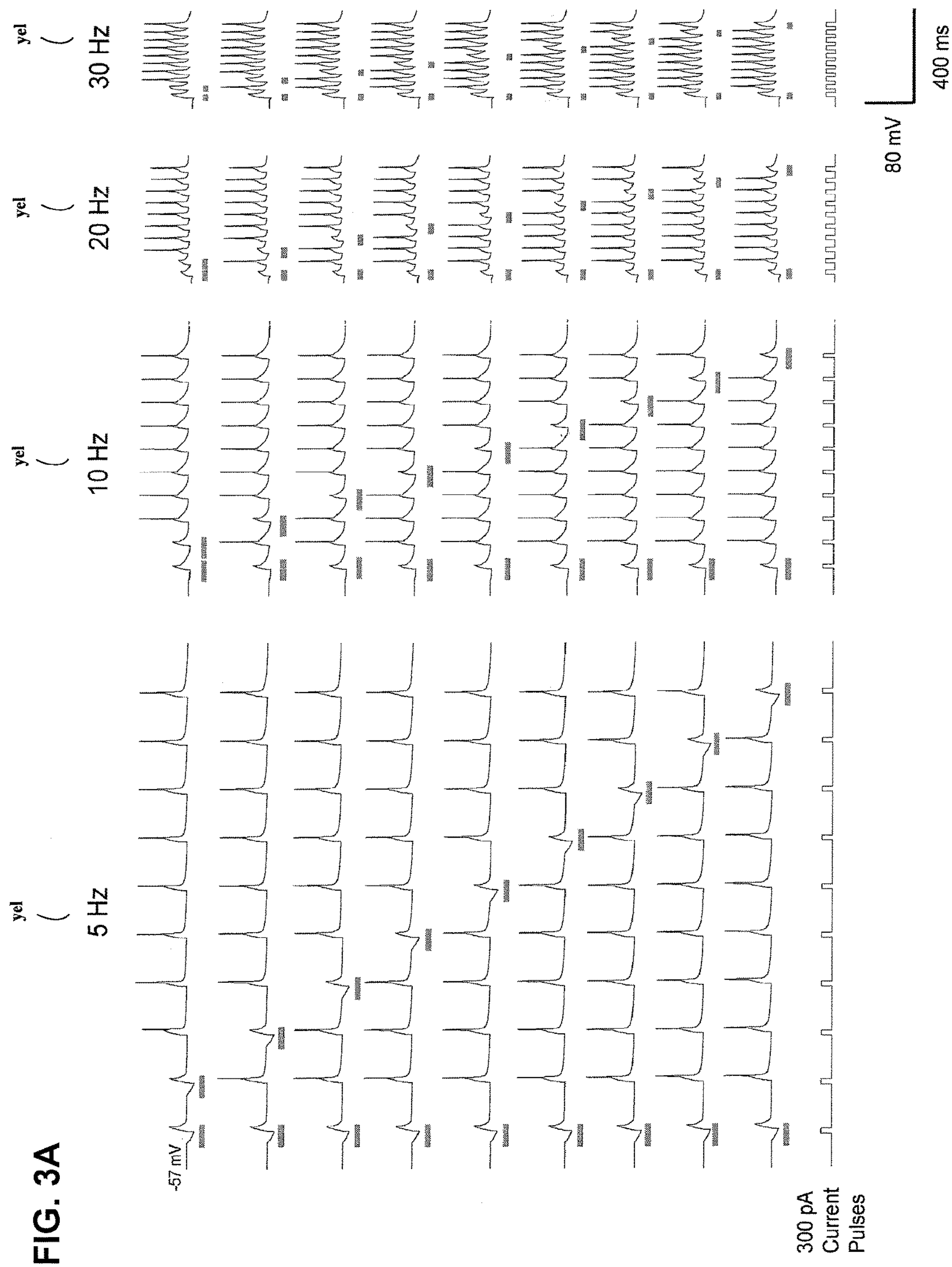
FIGS. 3A, 3B, 3C, 3D, 3E and 3F, show experimental results that are consistent with an example embodiment of the present invention.
Figure 3B:
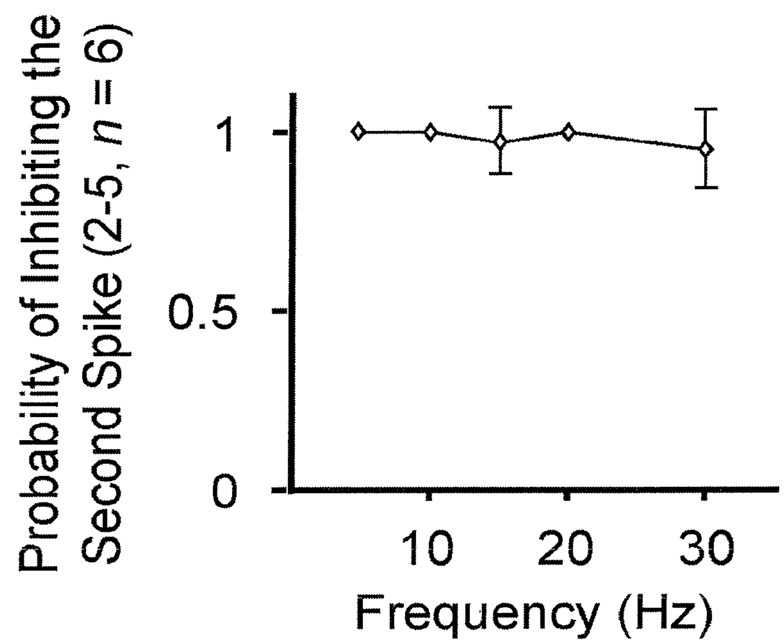
Figure 3C:
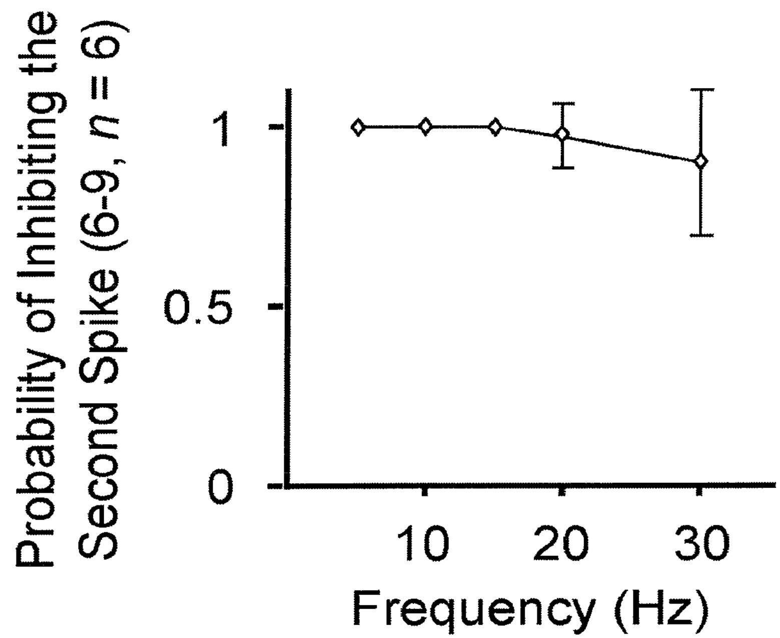
Figure 3D:
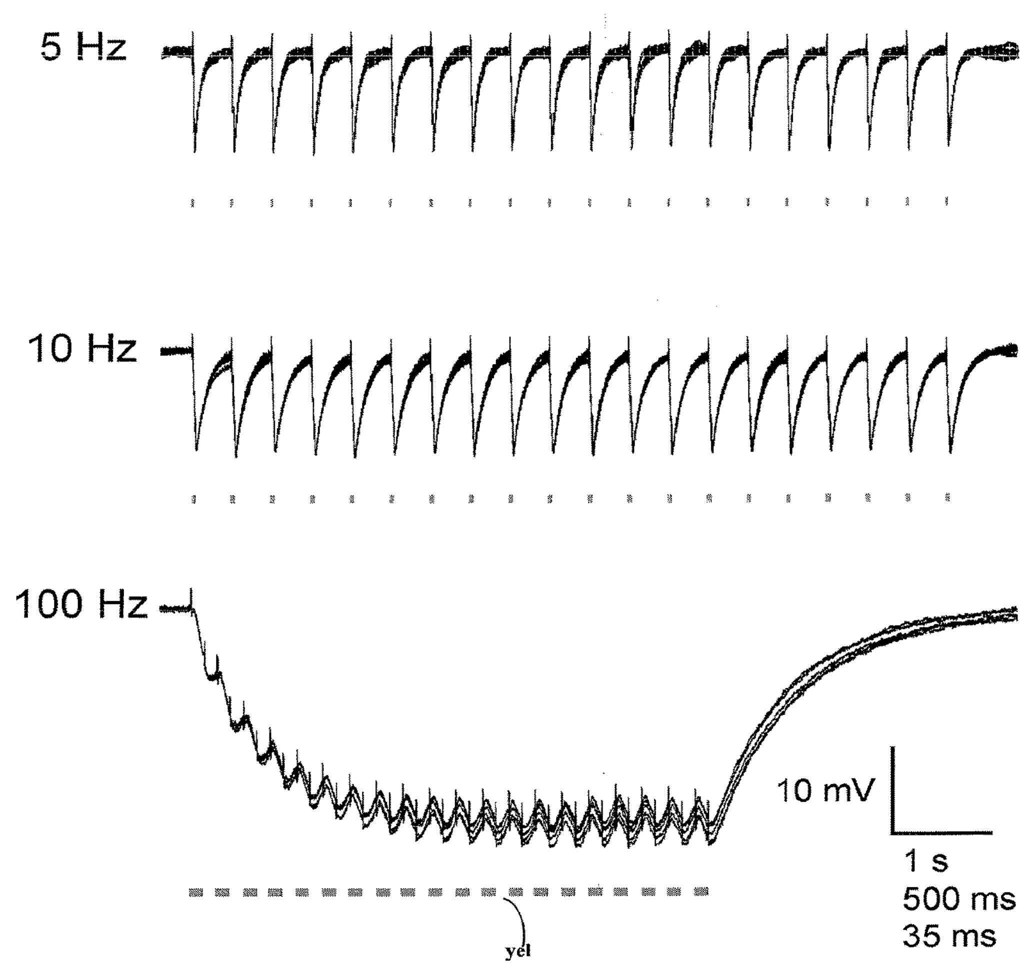

NpHR activation was tested for the ability to allow the "knockout" of single action potentials. The fast photocurrent of ChR2 enables brief pulses of blue light to drive reliable action potential trains. Concurrently applied brief pulses of yellow light were used to test NpHR-mediated inhibition. FIG. 3A shows the results of an attempt to inhibit pairs of spikes in action potential trains of 5, 10, 20, and 30 Hz. Indeed, single spikes could be reliably inhibited from within longer spike trains. Several pairs of spikes within a range of inter-spike temporal delays were inhibited in an effort to define the temporal precision of NpHR. FIGS. 3A, 3B and 3C show that both closely timed and temporally separated spike pairs were able to be reliably inhibited, while sparing spikes between the targeted times (n=6). Over spike rates of 5 to 30 Hz, the closely timed spikes could be selectively inhibited with a probability of 0.95 or greater. Moreover, FIG. 3D shows that by giving trains of millisecond-scale yellow light pulses, it is straightforward to simulate barrages of IPSP-like events with precise, reliable timing and amplitudes, from 5 to 100 Hz.

Figure 3E:
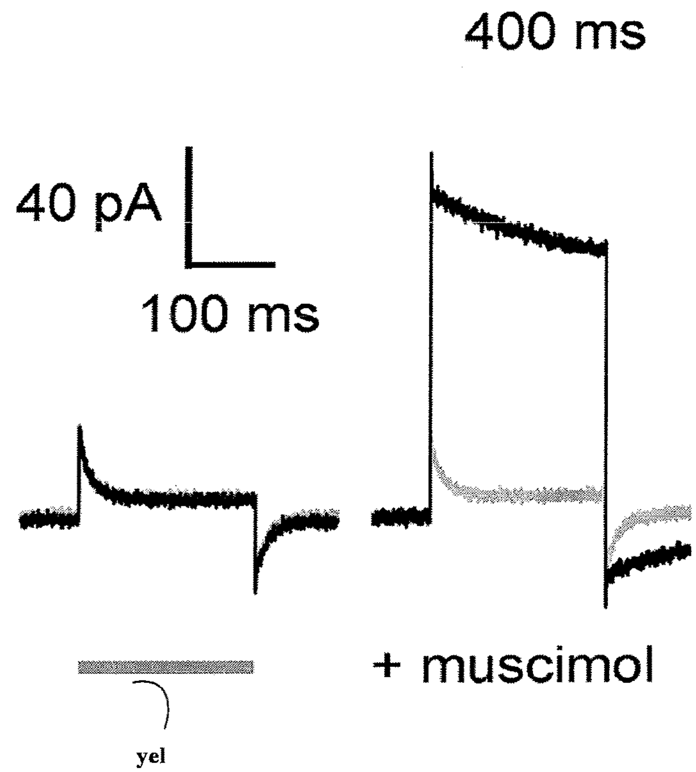
Figure 3F:
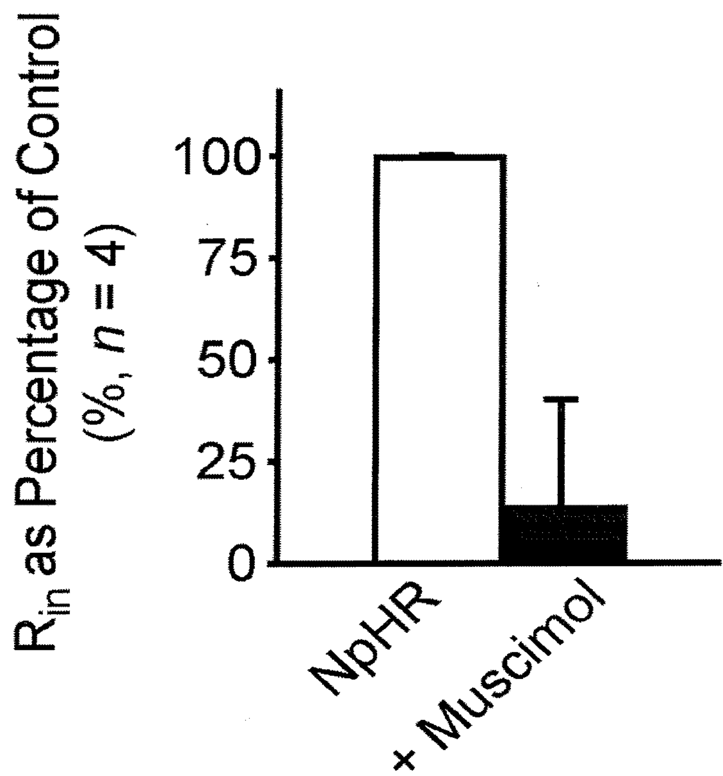

Since NpHR is a Cl− pump and not a channel, the light-driven inhibition acts by shifting the membrane potential and will not contribute (significantly) to shunting or input resistance changes. FIGS. 3E and 3F show that, whereas the $GABA_A$ chloride channel agonist muscimol significantly decreased neuronal input resistance, NpHR activation had no detectable effect on the input resistance.

Since both ChR2 and NpHR can be activated with high temporal precision using millisecondscale blue or yellow light pulses, an experiment was implemented to test the possibility of driving both proteins in intermingled temporally precise patterns. Such ability can be useful to noninvasively activate or inhibit single identified action potentials with light in the same experiment or even in the same cell. Cell attached and whole-cell recordings in hippocampal pyramidal neurons revealed that precisely patterned trains of yellow and blue light pulses can be used to evoke and inhibit neural activity with single spike precision, and that NpHR can be used to override multiple preselected ChR2-driven spikes at identified positions in prolonged spike trains.

Both NpHR and ChR2 can be functionally expressed in the mammalian brain without exogenous delivery of its required cofactor all-trans-retinal (ATR), presumably due to the presence of endogenous retinoids in the mammalian brain. As an experiment, lentiviruses carrying NpHR-EYFP were delivered under the neuronal CaMKIIα promoter into the hippocampus of the adult mouse. Neurons throughout the hippocampus exhibited stable expression of NpHR-EYFP, as indicated by a robust EYFP fluorescence.

NpHR-EYFP cells in acute hippocampal slices exhibited voltage clamp photocurrents similar to those observed in cultured neurons. A current clamp recording of NpHR-EYFP neurons revealed that temporally precise patterns of spike inhibition could be achieved readily as in dissociated culture. No exogenous cofactors were delivered at any point, indicating that NpHR can be functionally applied to mammalian systems in vivo.

In another instance, NpHR/ChR2 was combined in a system by expressing in living mammalian neural circuitry, with fura-2 calcium imaging, in an all-optical experiment. Lentiviruses carrying ChR2-mCherry under the neuron-specific CaMKIIα promoter and NpHR-EYFP under the EF-1 α promoter were injected into the brain of postnatal d4 mouse pups; acute cortical slices were prepared at postnatal d10-14 and labeled with fura-2-AM. In neurons co-expressing ChR2-mCherry and NpHR-EYFP, initial simultaneous illumination with both blue and yellow light did not lead to [Ca2+] transients while subsequent pulsed blue light alone in the same neurons evoked ChR2-triggered [Ca2+] transients. This demonstrates that NpHR and ChR2 can be integrated to achieve multimodal, bidirectional control of neural activity in intact tissue. In the same imaged cells (where ChR2 stimulation led to a 3.1±0.3% increase in ΔF/F), the combination of NpHR and ChR2 activation resulted in a 0.0±0.2% effect on ΔF/F (n=6, P<0.0001). Yellow illumination alone had no detectable effect on [Ca2+]. Since not all targeted cells are necessarily affected to the same degree, this optical system could complement electrophysiology to probe successful modulation of the targeted cell population. Thus, according to one embodiment, the combination of ChR2 and NpHR with calcium imaging provides an all-optical system for interrogation of neural circuits.

Another set of experiments were conducted to show control of animal behavior in vivo. An in vivo experiment involved expression of NpHR-ECFP fusion protein in the body wall muscles of the nematode *Caenorhabditis elegans* using the muscle-specific myosin promoter (Pmyo-3). ECFP fluorescence could be readily observed throughout muscle cells and membranous muscle arm extensions. As worms (unlike mammals) appear not to have sufficient levels of endogenous retinoids, transgenic animals expressing NpHR in muscle were grown in medium containing ATR. Whole-cell voltage-clamp recordings from dissected muscles indeed demonstrated light-evoked outward currents (265±82 pA, n=9). To test effects on muscle activity, swimming behavior in liquid medium was analyzed. Consistent with the photocurrents observed, photoactivation of NpHR immediately (within ~150 ms) and essentially completely arrested swimming behavior. Transgenic animals, raised in the absence of ATR and wild type animals raised with and without ATR, were used as controls. Robust paralyzing effects of light were observed, but consistently only in transgenic animals raised in the presence of ATR.

When transgenic muscle-expressing animals were illuminated for 1 second, they quickly returned to their natural swimming rate after light stimulus termination. When NpHR was activated in muscle for 10 seconds, animals remained uncoordinated for prolonged periods (up to 40 seconds), before a full recovery became apparent and normal swimming commenced.

Another experiment involved targeting of NpHR to a specific class of genetically defined neurons in vivo. NpHR-ECFP was expressed in cholinergic motoneurons using the vesicular acetylcholine transporter promoter (Punc-17). When illuminated for 1 or 10 seconds, respectively, these animals also strongly reduced or essentially stopped swimming behavior. These animals, in contrast to the muscle targeted individuals, recovered to normal swimming behavior immediately, perhaps indicating more powerful Cl– homeostasis in neurons than in muscles, although in all cases full recovery was observed consistent with the lack of toxicity observed in mammalian neurons. When illuminated on solid agar substrate, transgenic animals expressing NpHR either in muscle, or in cholinergic motoneurons, exhibited rapid inhibition of movement and relaxed their bodies, resulting in overall elongation by up to 9% within ~600 ms of illumination.

ChR2 and NpHR were found to be able to be driven simultaneously in *C. elegans*. With either muscle or targeted cholinergic neuron expression (using the Pmyo-3 or Punc-17 promoters, respectively), NpHR rapidly and reversibly counteracted the shortening behavior observed with ChR2 alone. These experiments demonstrate that acetylcholine release can be efficiently triggered from *C. elegans* motoneurons using ChR2, and that ChR2 and NpHR work well together in nematodes as well as mammals. In some instances, such an NpHR/ChR2 system enables rapid bidirectional control of neurons on the timescale of milliseconds, thus enabling emulation or alteration of the neural code. These fast genetically based neural spike-controlling technologies powerfully augment existing tools for interrogating neural systems. Indeed, integration of the NpHR/ChR2 neural control system with optical activity markers like fura-2, and with GFP-based morphological markers, delivers a versatile triad of technologies for watching, listening to, and controlling living neural circuitry with light.

Both NpHR and ChR2 can be functionally expressed and operate at high speed in the mammalian brain without necessitating cofactor addition. Moreover, NpHR and ChR2 function in behaving *C. elegans* as well after simple dietary ATR supplementation. When combined with optical imaging or behavioral measures in intact tissue or freely moving animals, the NpHR/ChR2 system provides the capability to directly and causally link precisely defined patterns of neural activity with specific circuit behaviors.

The ability to use light to inhibit or activate neurons has practical applications beyond basic science investigations. The NpHR/ChR2 system may be genetically targeted to specific classes of neurons or other excitable cells involved in disease processes to enable highly precise optical therapeutic treatments. For example, in Parkinson's disease where electrode-based deep brain stimulation (DBS) can be therapeutic for symptomatic relief but also gives rise to side effects, delivery of these optogenetic tools targeted by cell type-specific promoters to distinct disease-related neuronal types may ultimately provide a more precise alternative with fewer side-effects. Whether in basic science or clinical applications, the spectral separation between the NpHR and ChR2 activation maxima allows for the first time bidirectional optical control in the same target tissue, and permits both sufficiency and necessity testing in elucidation of the roles of specific cell types in high-speed intact circuit function.

Oocyte microinjection and physiology were experimentally carried out using the following procedures. NpHR cRNA was generated using the T7-cap scribe kit from Ambion (Austin, Tex.). Stage V/VI oocytes were prepared. Each oocyte was injected with 30 to 50 ng cRNA, incubated for 4 to 7 days at 16 to 18° C. with 1 μM ATR in the medium (90 mM NaCl, 2 mM KCl, 1 mM MgCl2, 1.8 mM CaCl2, 5 mM HEPES, pH 7.4/NaOH) to reconstitute functional HR. As a control uninjected oocytes were incubated in the same medium. Oocytes were recorded using two-electrode voltage-clamp (Turbo Tec-05) and illuminated with a continuous He—Ne laser (594 nm, LYHR-0600M, Laser 2000, Wessling, Germany). The maximum light intensity was 3 $mW/mm^2$ and was focused to a diameter close to the dimensions of the oocyte. In giant patch experiments from halorhodopsin-expressing oocytes a continuous He—Ne laser of 633 nm with light intensities up to 400 mW/mm2 was used.

Figure 9:
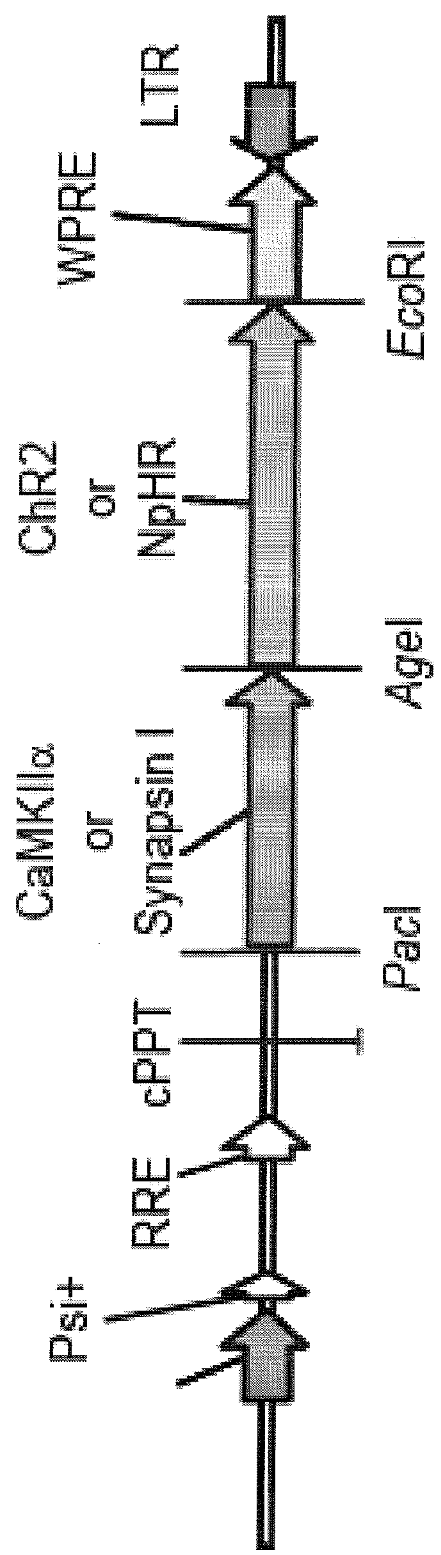
FIG. 9 shows Lentiviral vector construction, according to an example embodiment of the present invention.

Lentiviral vector construction was experimentally carried out using the following procedures. Lentiviral vectors containing Synapsin I::ChR2-mCherry, CaMKIIα::ChR2-mCherry, and CaMKIIα::NpHR-EYFP were based on the FCK(1.3)GW plasmid. For the construction of these lentiviral vectors, the promoter was PCR amplified and cloned into the Pacl and Agel restriction sites (FIG. 9). The transgene ChR2-mCherry or NpHR-EYFP were PCR amplified and cloned into the Agel and EcoRI restriction sites. The pLEHYT vector is constructed in the same way as pLECYT3 by inserting the NpHR-EYFP gene into the Afel and Spel restriction sites of pLEGT.

For both NpHR-EYFP and ChR2-mCherry, the protein fusion was made via a NotI restriction site. The linker between the two proteins is 5'-GCGGCCGCC-3'. The start codon on the fluorescent protein was removed deliberately to avoid translation of the fluorescent protein alone. In addition to the promoter, each lentiviral vector contains the HIV-1 central polypurine tract (cPPT) and the Woodchuck Hepatitis Virus Post-transcriptional Regulatory Element (WPRE) to improve transduction efficiency.

Lentiviral production and transduction were experimentally carried out using the following procedures. High-titer lentiviruses were produced using a second generation lentiviral system, by cotransfection of 293FT cells (Invitrogen) with pCMVΔR8.74 and pMD2.G in addition to the viral vector. The following protocol was used.

Day 0: Split 4 T-225 flasks (Nunc) of 95% confluent 293FT cells into one 4 layer CellFactory (Nunc). Culture using 500 mL of DMEM with 10% FBS. Incubate the plates at 37° C. overnight. The cells should reach 90% confluence in 24 hours.

Day 1: Perform calcium phosphate transfection; make DNA mixture containing 690 μg of the viral vector, 690 μg of pCMVΔR8.74, and 460 μg of pMD2.G. Add 5.7 mL of 2M CaCl2 to the DNA mixture and bring the total volume to 23.75 mL with distilled H2O; then, quickly combine the DNA/CaCl2 solution with 23.75 mL of 2×HBS (50 mM HEPES, 1.5 mM Na2HPO4, 180 mM NaCl, pH 7.05; note that the pH is important); after quickly mixing by inverting 5 times, add the DNA/CaCl2/HBS solution to 500 mL of room-temperature DMEM with 10% FBS to make the transfection media; then, exchange the media in the CellFactory with the transfection media.

Day 2: 15 hours from the time of transfection, remove the transfection media from the CellFactory and wash the cells 3 times with fresh room-temperature DMEM; incubation longer than 15 hours may lead to cell death and reduced viral titer; finally, replace the media with 500 mL of fresh DMEM containing 10% FBS and incubate in a 37° C. incubator for 9 hours.

Day 2.5: 24 hours from the time of transfection, remove the media from the CellFactory and replace with 200 mL of serum-free media (UltraCULTURE, Cambrex) containing 5 mM Sodium Butyrate; return the CellFactory to the incubator.

Day 3: 40 hours from the time of transfection, collect the 200 mL of media from the CellFactory. This is the viral-containing supernatant. Centrifuge at 1000 rpm for 5 minutes to precipitate large cell debris and then filter the viral supernatant using a 0.45 μm low-protein binding filter flask. Then, centrifuge the supernatant using a SW-28 rotor (Beckman Coulter) for 2 hours at 55,000×g to precipitate the virus. Usually 6 centrifuge tubes are required to concentrate all of the viral supernatant. Before spinning, add 2 mL of PBS containing 20% sucrose to the bottom of the centrifuge tube to remove any remaining cell debris during centrifugation. After centrifugation, gently decant the liquid from the centrifuge tubes and re-suspend all 6 viral pellets with 100 μL of 4° C. PBS. Then, aliquot the viral solution and store at −80° C. for future use. If desired, 10 mL of unconcentrated viral supernatant can be stored before centrifugation for in vitro use in cultured neurons. For culture applications, neurons can be transduced simply by adding 50 μL of unconcentrated viral supernatant per 24-well plate well. Protein expression can be observed 4 to 5 days later. For in vivo applications, concentrated virus can be directly injected into the mammalian brain.

For whole-cell and cell-attached recording in cultured hippocampal neurons or acute brain slices, three intracellular solutions containing 4 mM chloride were prepared (135 mM K-Gluconate, 10 mM HEPES, 4 mM KCl, 4 mM MgATP, 0.3 mM Na3GTP, titrated to pH 7.2), 10 mM chloride (129 mM K-Gluconate, 10 mM HEPES, 10 mM KCl, 4 mM MgATP, 0.3 mM Na3GTP, titrated to pH 7.2), or 25 mM chloride (114 mM K-Gluconate, 10 mM HEPES, 25 mM KCl, 4 mM MgATP, 0.3 mM Na3GTP, titrated to pH 7.2).

For cultured hippocampal neurons, Tyrode's solution was employed as the extracellular solution (125 mM NaCl, 2 mM KCl, 3 mM CaCl2, 1 mM MgCl2, 30 mM glucose, and 25 mM HEPE, titrated to pH 7.3).

For preparation of acute brain slices, mice were sacrificed 2 weeks after viral injection. 250 μm acute brain slices were prepared in ice-cold cutting solution (64 mM NaCl, 25 mM NaHCO3, 10 mM glucose, 120 mM sucrose, 2.5 mM KCl, 1.25 mM NaH2PO4, 0.5 mM CaCl2, 7 mM MgCl2, and equilibrated with 95% O2/5% CO2) using a vibratome (VT1000S, Leica). Slices were incubated in oxygenated ACSF (124 mM NaCl, 3 mM KCl, 26 mM NaHCO3, 1.25 mM NaH2PO4, 2.4 mM CaCl2, 1.3 mM MgCl2, 10 mM glucose, and equilibrated with 95%+O2/5% CO2) at 32° C. for 30 min to recover.

For calcium imaging, lentiviruses were injected into the cortex of C57BL/6 mice at postnatal day 4 or 5 and acute brain slices were prepared 7 to 8 days later for adult mice.

Transgenic *C. elegans* Lines and Transgenes were experimentally developed using the following procedures. The NpHR gene was placed under the muscle-specific myo-3 promoter (untagged NpHR in transgene zxEx29[pmyo-3::NpHR; lin-15+] and NpHR-ECFP in transgene zxEx30 [pmyo-3::NpHR-ECFP; rol-6d]) or under the cholinergic motoneuron specific unc-17 promoter (NpHRECFP in transgene zxEx33[punc-17::NpHR-ECFP; lin-15+]). The NpHR-ECFP fusion (zxEx30 and zxEx34, see below) was employed to assess expression pattern. NpHR-ECFP (zxEx30) animals showed light induced effects that were comparable to the untagged version (zxEx29).

For co-activation of ChR2/NpHR in muscles or cholinergic motoneurons, transgenes zxEx32[pmyo-3::NpHR; pmyo-3::ChR2(H134R)-EYFP; lin-15+] and zxEx34[punc-17::NpHRECFP; punc-17::ChR2(gf)-YFP; rol-6d] were used. Table 1 lists examples of transgenes and worm lines used in various experimental tests.

TABLE 1

| Transgene | Genotype | Strain |
|---|---|---|
| zxEx29 [p myo-3::NpHR; lin-15$^+$] | lin-15 (n765ts$^-$) | ZX396 |
| zxEx30 [p myo-3::NpHR-ECFP; rol-6d] | N2 | ZX397 |
| zxEx32 [p myo-3::NpHR; p myo-3::ChR2(H134R)-EYFP; lin-15$^+$] | lin-15 (n765ts$^-$) | ZX399 |
| zxEx33 [p unc-17::NpHR-ECFP; lin-15$^+$] | lin-15 (n765ts$^-$) | ZX416 |
| zxEx34 [p unc-17::NpHR-ECFP; p unc-17:: ChR2(H134R)-EYFP; rol-6d] | N2 | ZX417 |

Experimental tests for bidirectional optical neural control and in vivo implementation were implemented. NpHR in muscle were grown in medium containing ATR. Whole-cell voltage-clamp recordings from dissected muscles indeed demonstrated light-evoked outward currents (265±82 pA, n=9). To test effects on muscle activity, swimming behavior in liquid medium was analyzed. Consistent with the photocurrents observed, photoactivation of NpHR immediately (within ~150 ms) and essentially completely arrested swimming behavior. As controls, transgenic animals that were raised in the absence of ATR, and wild type animals that were raised with and without ATR were used. Robust paralyzing effects of light were observed, but consistently only in transgenic animals raised in the presence of ATR. When muscle-expressing animals were illuminated for 1 s, they quickly returned to their natural swimming rate after light stimulus termination. When NpHR was activated in muscle for 10 s, animals remained uncoordinated for prolonged periods (up to 40 seconds), before a full recovery became apparent and normal swimming commenced.

Next, NpHR was targeted to a specific class of genetically defined neurons in vivo. NpHR-ECFP was expressed in cholinergic motoneurons using the vesicular acetylcholine transporter promoter (Punc-17). When illuminated for 1 or 10 s, respectively, these animals also strongly reduced or essentially stopped swimming behavior. These animals, in contrast to the muscle-targeted individuals, recovered to normal swimming behavior immediately, perhaps indicating more powerful $Cl^-$ homeostasis in neurons than in muscles, although in all cases full recovery was observed consistent with the lack of toxicity observed in mammalian neurons.

When illuminated on solid agar substrate, transgenic animals expressing NpHR either in muscle, or in cholinergic motoneurons, exhibited rapid inhibition of movement and relaxed their bodies, resulting in overall elongation by up to 9% within ~600 ms of illumination. It was found that ChR2 and NpHR could be driven simultaneously in *C. elegans* as well. With either muscle or targeted cholinergic neuron expression (using the Pmyo-3 or Punc-17 promoters, respectively), NpHR rapidly and reversibly counteracted the shortening behavior observed with ChR2 alone. These experiments demonstrate that acetylcholine release can be efficiently triggered from *C. elegans* motoneurons using ChR2, and that ChR2 and NpHR work well together in nematodes as well as mammals.

Slides were developed showing cell-attached (FIG. 4A left) and whole-cell (FIG. 4A right) recording of cultured hippocampal neurons co-expressing ChR2-mCherry and NpHR-EYFP. Action potentials were evoked via trains of blue light pulses (5 Hz trains, 15 ms pulse width, lowest set of bars). NpHR-mediated inhibition was co-administered by brief yellow light pulses (50 ms pulse width, upper sets of bars).

Figure 4B:
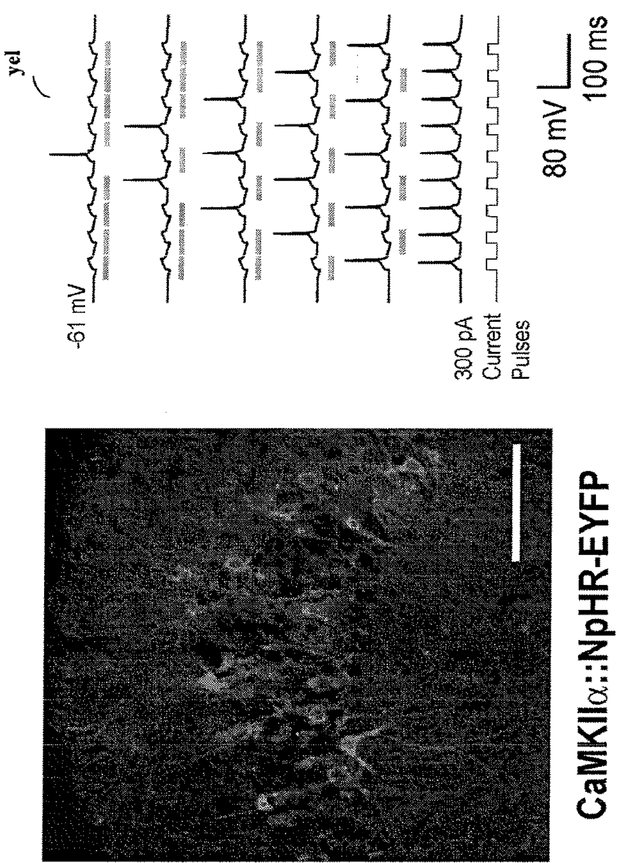
FIGS. 4A, 4B, 4C, 4D, 4E, 4F, 4G and 4H, show experimental results that are consistent with an example embodiment of the present invention.
Figure 4A:
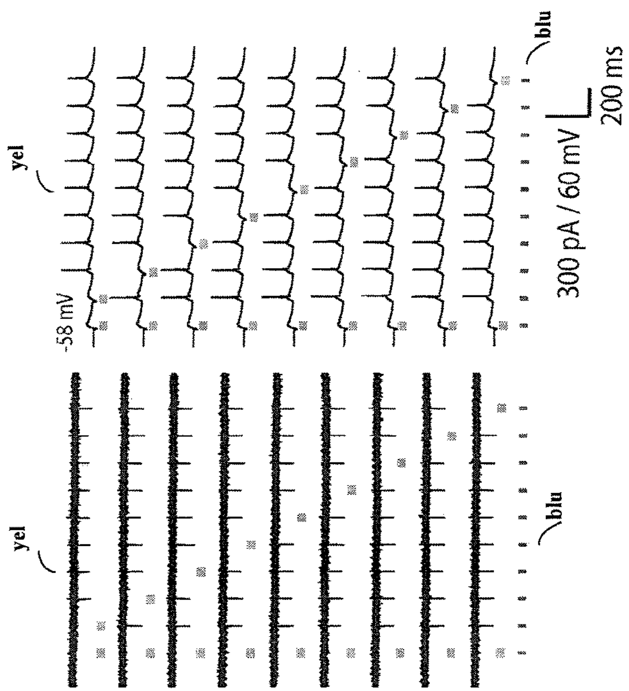

A confocal image was taken from acute mouse brain slice showing membrane-localized NpHR-EYFP expression in the hippocampal CA3 subfield (FIG. 4B left). Current clamp recording showed NpHR-mediated inhibition of specific spikes during a train of action potentials evoked by pulsed current injection (300 pA, 20 Hz, FIG. 4B right).

Epifluorescence images of cortical neurons triple-labeled with NpHR-EYFP, ChR2-mCherry, and Fura-2 showed expression in the neurons. (FIG. 4C)

Figure 4D:
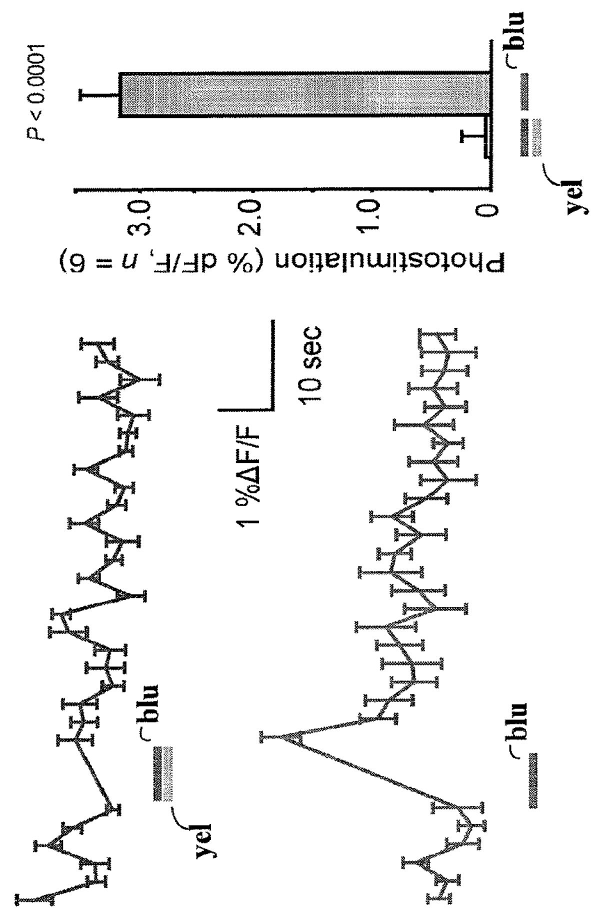
Figure 4C:
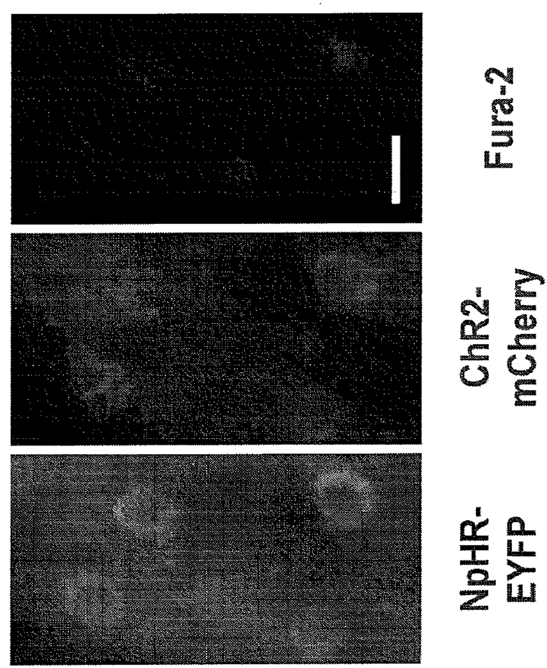

Simultaneous illumination of cells co-expressing NpHR-EYFP and ChR2-mCherry with steady yellow (continuous illumination, 6 s) and pulsed blue light (50 pulses at 15 ms per flash, 10 Hz) prevented [Ca2+] transients (FIG. 4D). Subsequent photostimulation of the same cells with blue light pulses (50 pulses at 15 ms per flash, 10 Hz) evoked reliable [Ca2+] transients. A bar graph was generated that shows the photostimulation-induced fluorescence changes (FIG. 4D, n=6 ChR2-activated triple-labeled cells).

Figure 4F:
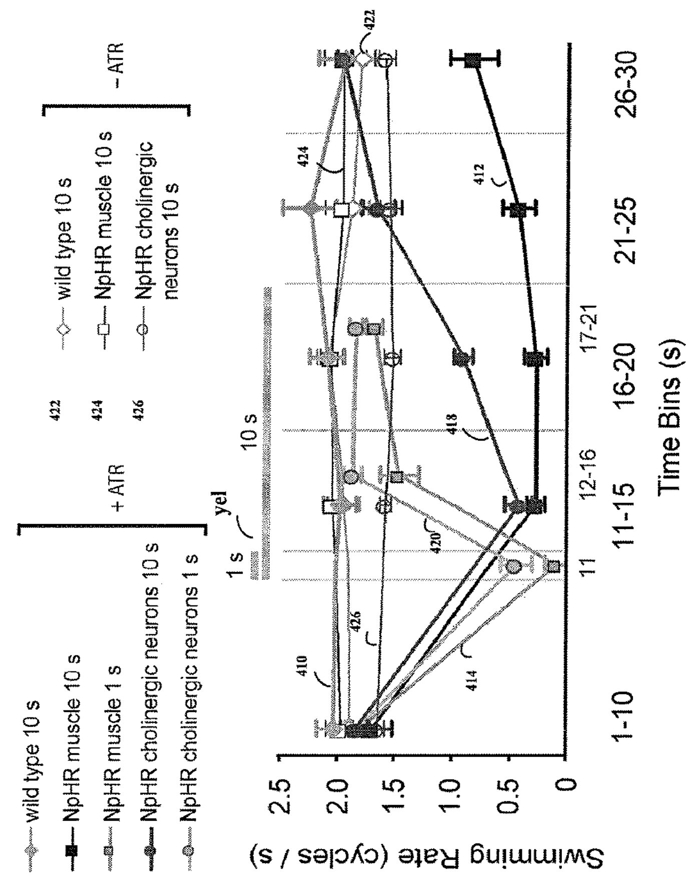
Figure 4E:
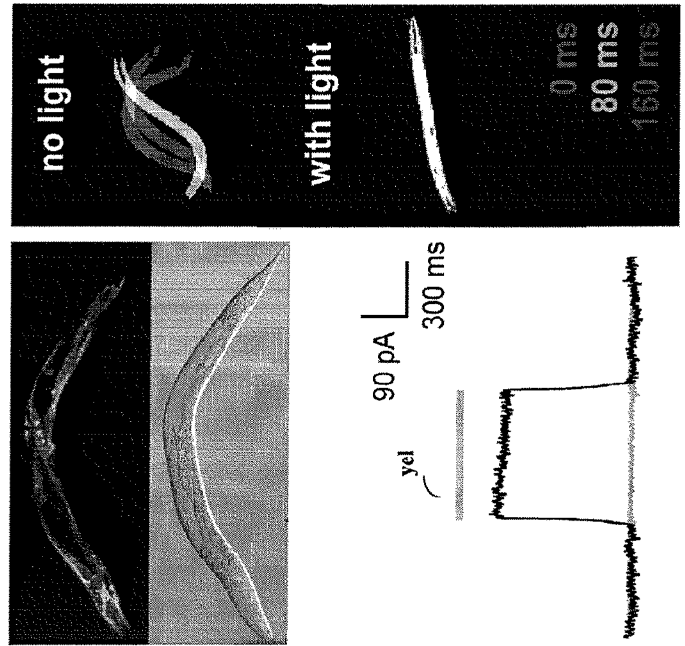

Epifluorescence images showed Pmyo-3-mediated (transgene zxEx30) NpHR-ECFP expression in the body wall muscles of *C. elegans* (FIG. 4E). A muscle voltage clamp trace showed photocurrent in transgenic *C. elegans* expressing NpHR-ECFP (transgene zxEx30) and raised in the presence of ATR. A lack of response in transgenic animal raised in the absence of ATR was noted. Animal postures from three consecutive movie frames (frame rate 12.5 Hz), either with or without NpHR photoactivation, were superimposed to show lack of movement in NpHR photoactivated animals.

The effect of 10 s illumination on swimming rate (n=10 for each set) in wild type controls, animals expressing NpHR in muscles (transgene zxEx29, FIG. 4F blue), or cholinergic motoneurons (transgene zxEx33, FIG. 4F red) was monitored. The number of swimming cycles per second was counted in bins of 5 s intervals. A briefer 1 s illumination protocol was also used, revealing rapid inhibition during illumination and faster recovery by comparison with the 10 s illumination.

Figure 4G:
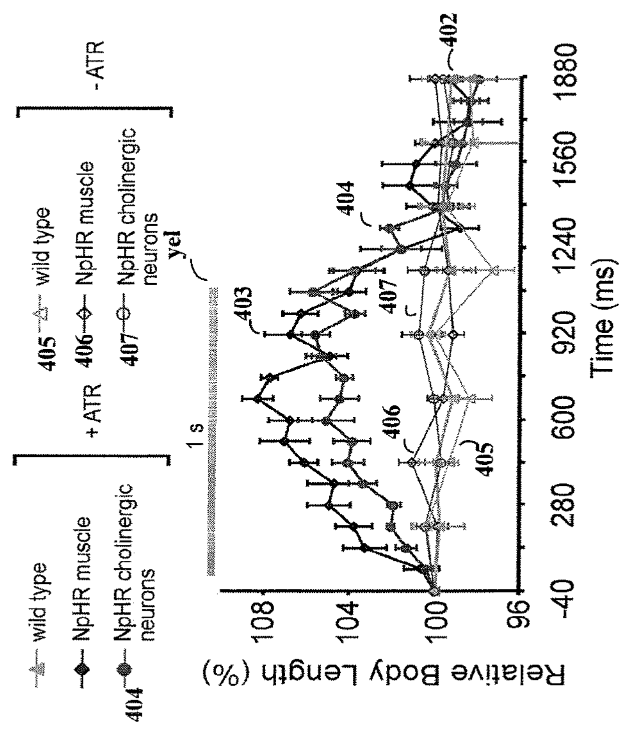
Figure 4H:
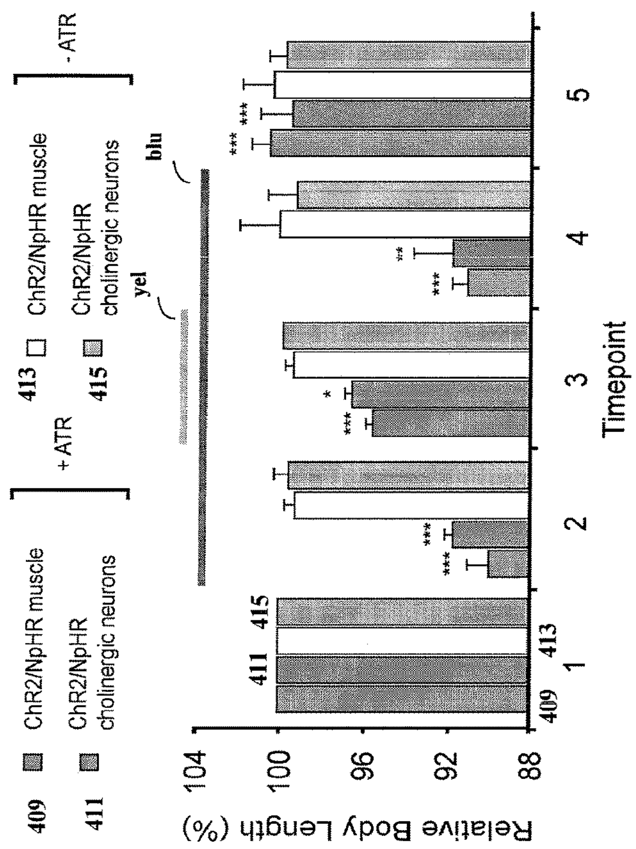

The effect of 1 s illumination on body length (n=5-6 for each set) was monitored (FIG. 4G). Movies were taken from transgenic worms expressing NpHR in muscles (transgene zxEx29) or cholinergic motoneurons (transgene zxEx33). Combined ChR2/NpHR expression in muscle cells (transgene zxEx32) or cholinergic motoneurons (transgene zxEx34) of behaving worms. A plot was generated that shows the body length during the first frame before illumination, the 13 frames during the illumination and the next 11 frames after illumination ended (FIGS. 4F, 4G and 4H) including controls and combined ChR2/NpHR expression in muscle cells (transgene zxEc32) or cholinergic motoneurons (transgene zxEx34) of behaving worms.

NpHR activation significantly reversed the muscle contraction caused by ChR2 activation (n=6 per condition; *, $p<0.05$; , $p<0.01$; *, $p<0.001$; between consecutive time points; t-test), but not in animals raised in the absence of ATR.

According to a first experimental method, swimming of a transgenic *C. elegans* expressing NpHR (transgene zxEx29) in muscles is instantaneously, and repeatedly, inhibited by photoactivation of HR.

According to a second experimental method, swimming of a transgenic *C. elegans* expressing NpHR in cholinergic motoneurons (transgene zxEx33) is instantaneously inhibited by photoactivation of NpHR.

According to a third experimental method, transgenic *C. elegans* expressing NpHR-ECFP in muscles (transgene zxEx30). Movement is rapidly inhibited (3×) by photoactivation of HR, and the body relaxes and dilates.

According to a fourth experimental method, one transgenic *C. elegans* expressing NpHR in muscles (transgene zxEx29), and one non-transgenic control animal. Movement of the transgenic animal is rapidly inhibited by photoactivation of HR.

According to a fifth experimental method, transgenic *C. elegans* expressing NpHR in cholinergic motoneurons (transgene zxEx33). Movement is rapidly inhibited by photoactivation of HR, and the body relaxes and dilates.

According to a sixth experimental method, co-expression and -activation of ChR2(H134R)-EYFP and NpHR in cholinergic motoneurons of transgenic *C. elegans* (transgene zxEx34). The animal is illuminated with blue light for ChR2 activation, causing contractions, then, while ChR2 is still photoactivated, NpHR is photoactivated by yellow light, causing significant body relaxation. When NpHR activation ends, the animal contracts again (ChR2 still activated), and finally, when ChR2 activation ends, the animal relaxes to the initial body length.

According to a seventh experimental method, co-expression and rapidly alternating activation of ChR2(H134R) EYFP and NpHR in muscles of transgenic *C. elegans* (transgene zxEx32). The animal is illuminated with alternating blue light (for ChR2 activation), causing contractions, and yellow light causing significant body relaxation.

Figure 5:
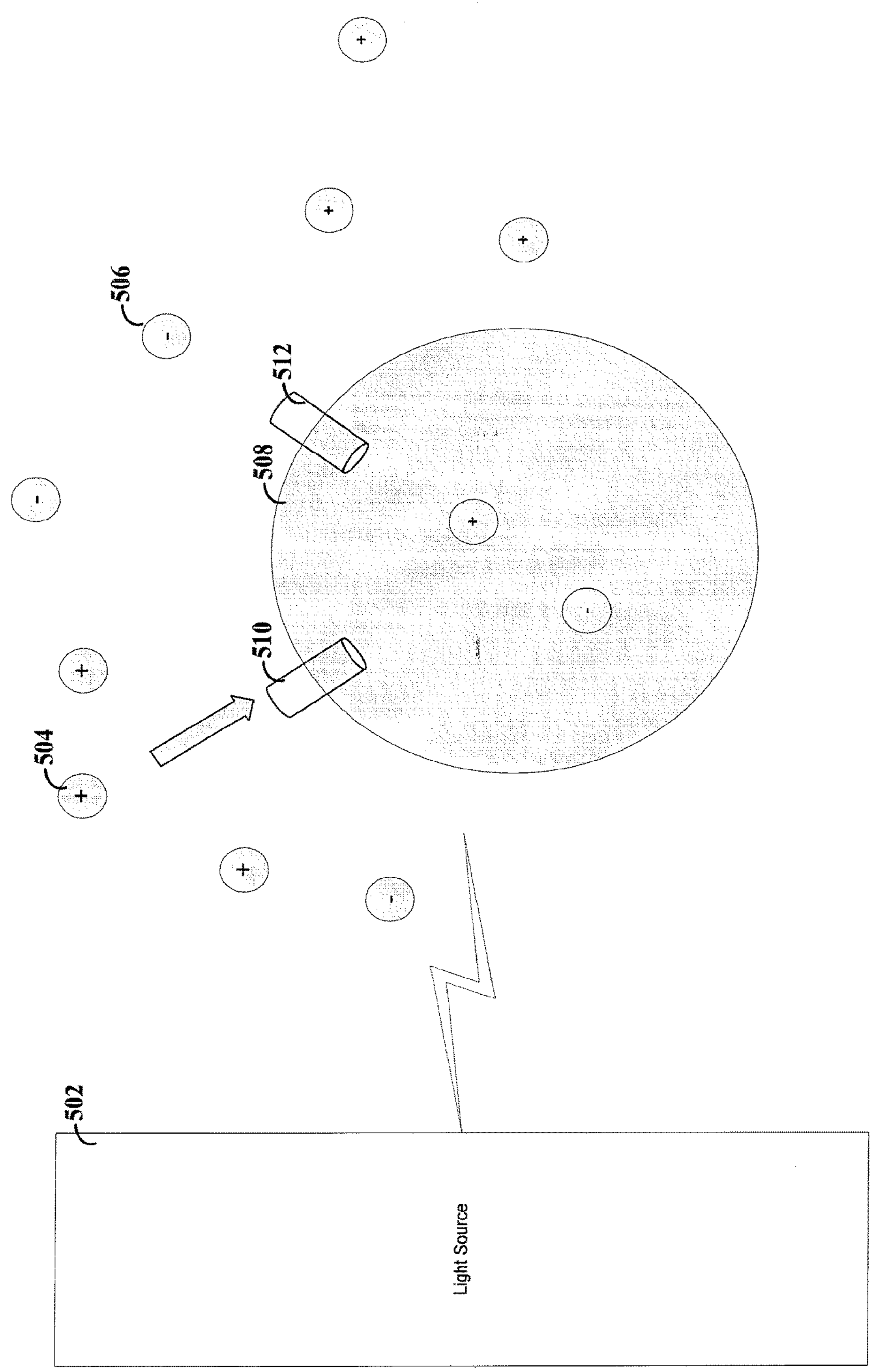
FIG. 5 shows a light source and modified cell, according to an example embodiment of the present invention.

FIG. 5 depicts an arrangement with multiple light sources, according to an example embodiment of the present invention. FIG. 5 shows light sources 502 and 504 that illuminate proteins 510 and 514. The proteins 510 and 514 are engineered within cell 512 to control current across the cell membrane in response to light from light sources 502 and 504, respectively. In one instance, the first protein 510 functions to dissuade action potential firing, while the second protein 514 functions to encourage action potential firing. Each of proteins 510 and 514 are responsive to light. In a particular instance, the first protein is responsive to light from light source 502 having a wavelength A and the second protein is responsive to light from light source 504 having a wavelength B. Thus, the light sources can be used to control each protein independently. This can be useful for both encouraging and dissuading action potentials in the cell. In another instance, having both types of proteins allows for both positive and negative control of the cell membrane voltage. Thus, the different light sources and proteins could be used to control the voltage or current level (e.g., clamping) of the cell membrane.

One method of determining responsiveness involves quantifying the responsiveness in terms of the intensity of light required to produce a given response. In some instances, the first or second protein can still be responsive to the alternate wavelength of light although the responsiveness of the protein may be less than that of the primary wavelength. Accordingly, a protein of a first type may have some responsiveness to the wavelength corresponding to the other type of protein while still maintaining sufficient independence of operation. In one such instance, control of the cell can be implemented by shifting either the wavelength of light or the intensity of the light. For instance, the wavelength can be shifted between A and B to induce a corresponding increase or decrease the membrane voltage potential.

Embodiments of the invention can be implemented with just the protein based ion pump(s). In a specific example, pump 510 is designed to operate using an endogenous cofactor, such as ATR, which can be found in people and many animals. This is particularly useful for minimizing intrusiveness of in vivo applications because it can reduce the need for foreign substances (e.g., cofactors). In a particular instance, pump is a halorhodopsin that acts as an anion pump (e.g., $Cl^-$) that is activated in response to light from light source 502 within milliseconds. Such a fast response allows for the system to control (dissuade) individual action potentials in the cell.

According to one embodiment of the present invention, pump 514 can optionally be implemented for purposes other than dissuading action potential firing, such as controlling the voltage level of cell 508. More specifically, a sensor can be used to provide feedback to the light source 502. For instance, this feedback could be a measurement of the voltage or current across the cell membrane. Thus, the light source could be configured to maintain a constant current or voltage (e.g., clamp) across the cell. Moreover, the amount of responsiveness can be controlled by modifying one or more of the intensity and wavelength of the light.

Figure 6:
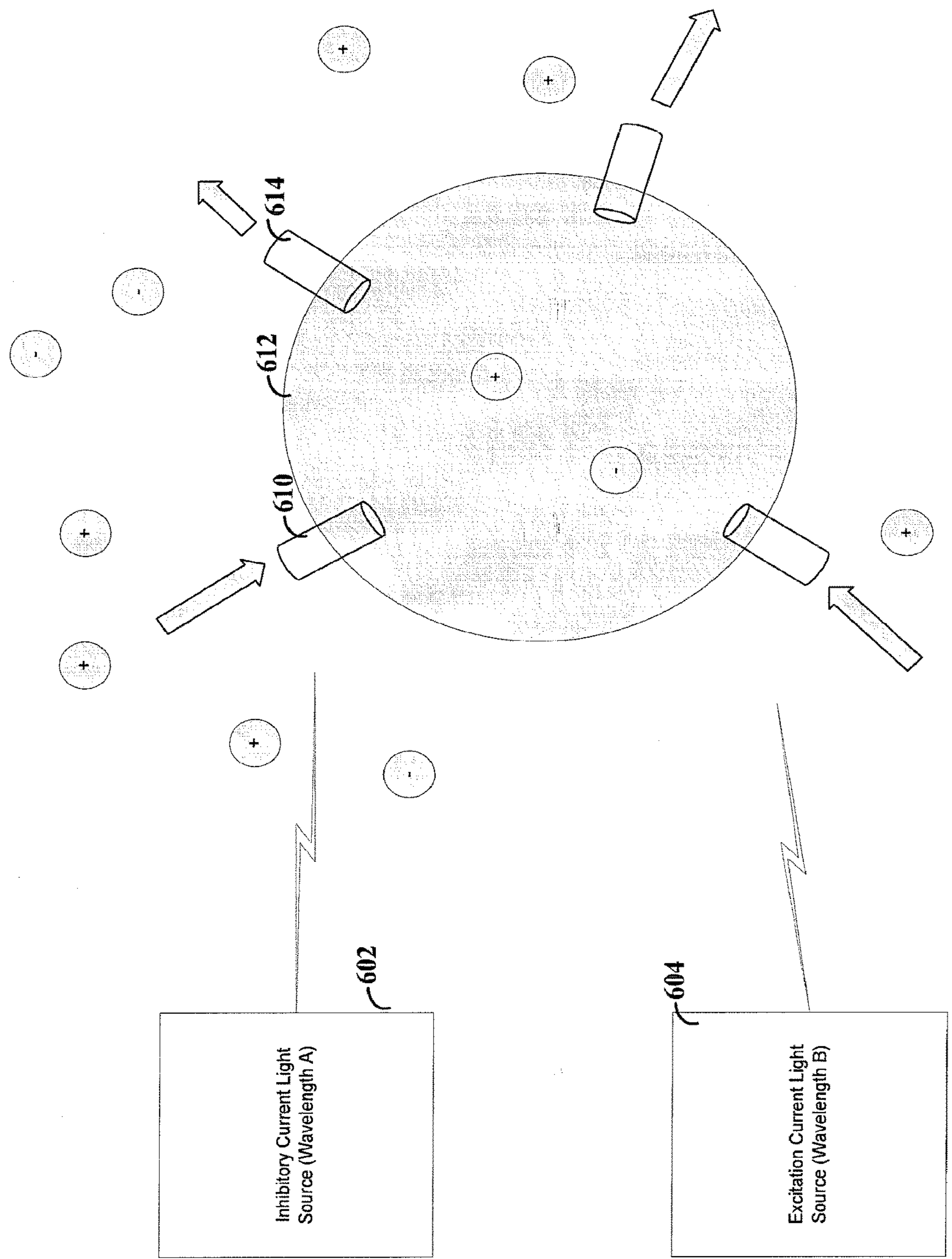
FIG. 6 depicts an arrangement with multiple light sources, according to an example embodiment of the present invention.

FIG. 6 shows a system for controlling electrical properties of one or more cells in vivo, according to an example embodiment of the present invention. Control/Interface unit 602 enables/disables light source 604 to illuminate target cells 608. A delivery mechanism, such as fiber optic cable 606, routes or otherwise directs the light to target cells 608. Fiber optic cable 606 may include a bundle of optical cables, each capable of carrying and directing light independently. Thus, fiber optic cable 606 can be configured to deliver light having one or more wavelengths to multiple locations. Sensor 610 can be implemented, e.g., as an optical device such as an optical scope or as a voltmeter, to provide feedback to control unit 642. In a particular instance, the feedback includes optical imaging of the target cells or of other related cells. In another instance, the feedback could monitor the voltage response of the target cells, including the amount of action potential firing.

Figure 7:
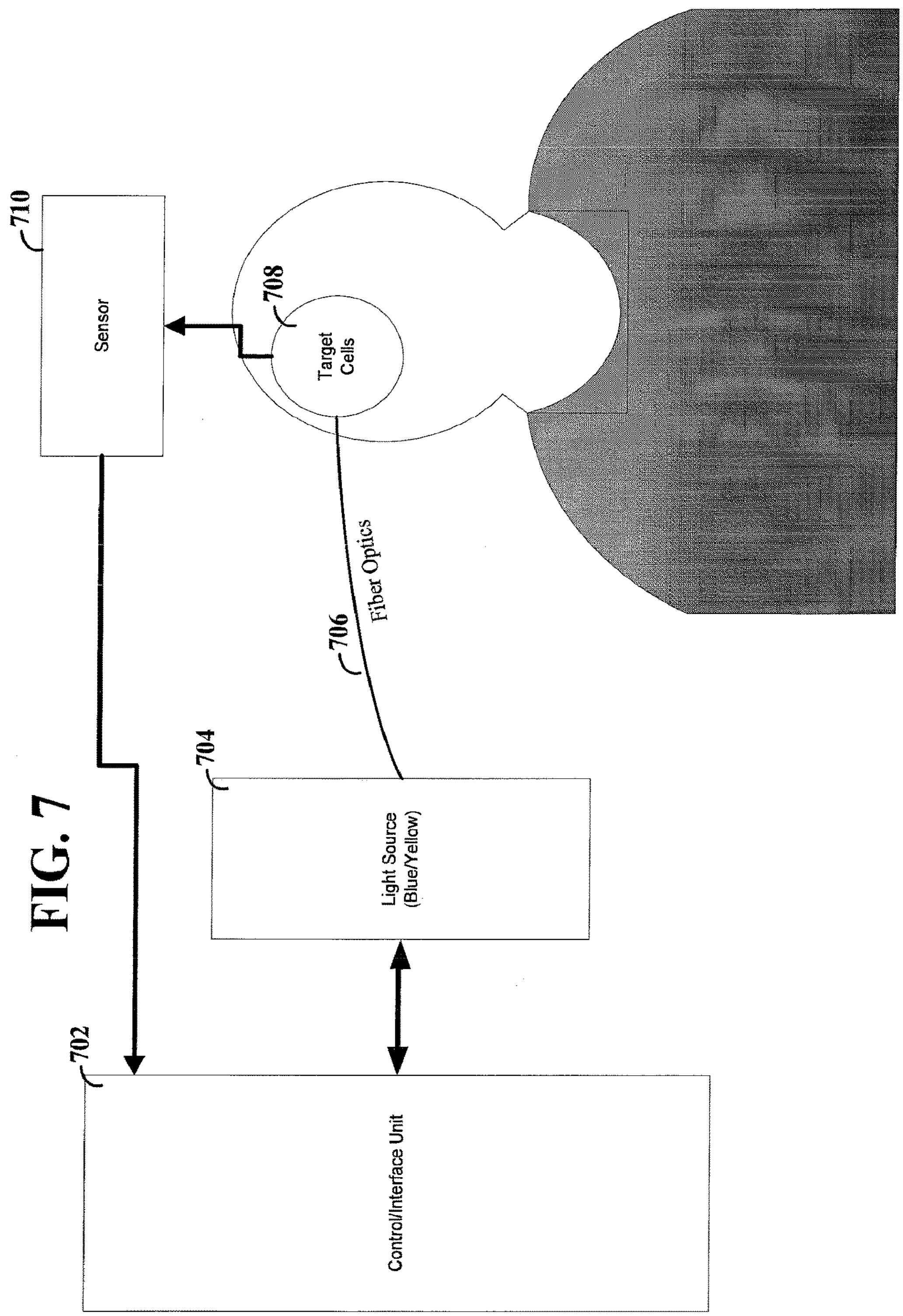
FIG. 7 shows a system for controlling electrical properties of one or more cells in vivo, according to an example embodiment of the present invention.
Figure 8:
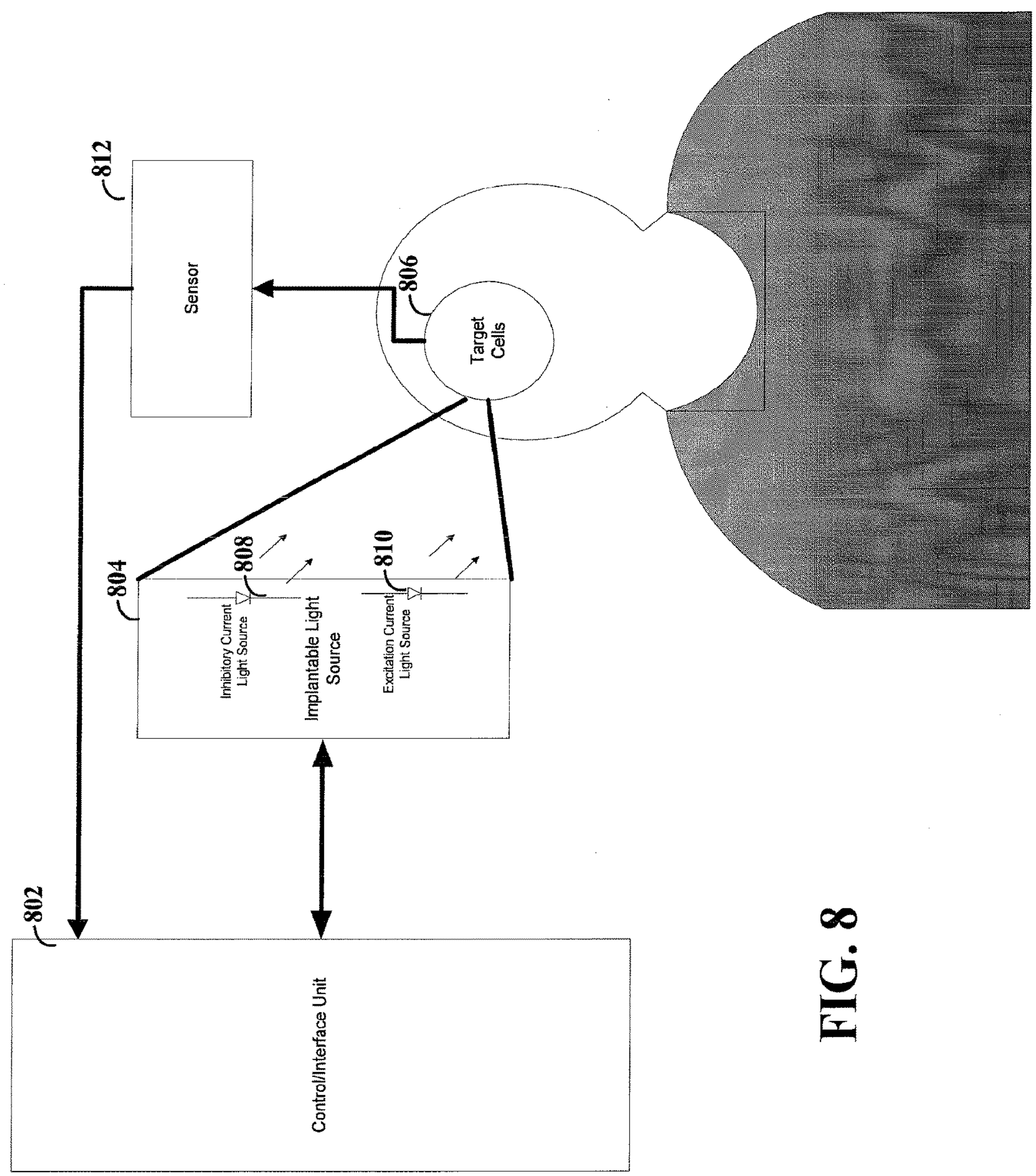
FIG. 8 shows a system for controlling electrical properties of one or more cells in vivo, according to an example embodiment of the present invention.

FIG. 7 shows a system for controlling electrical properties of one or more cells in vivo, according to an example embodiment of the present invention. Control/Interface unit 702 enables/disables implantable light source 704, which in turn illuminates target cells 706. Light source 704 is shown with two light source, inhibitory current light source 708 and excitation current light source 710. Light source 708 produces light at a wavelength and intensity that an inhibitory protein is responsive to, while light source 710 produces light at a wavelength and intensity that an excitation protein is responsive to. One skilled in the art would recognize that various configurations of light source 710 are possible, including a single inhibitory light source or an array of light sources having one or more wavelengths. Control/Interface unit 702 communicates with light source 704 through any suitable communication mechanisms, such as wired communications or wireless communications using radio-frequency signals, magnetic signals and the like. As discussed above in connection with FIG. 6, sensor 712 can optionally be implemented for providing feedback to control unit 702.

Another important aspect of the present invention concerns applications and uses which benefit by reducing toxicity of cells. In certain applications and uses, cells modified to include ion pump molecules can become intolerably toxic. Toxicity can become increasingly problematic as the expression level increases in a cell or the network, for example, when expecting consistent results under repeated tests using the same cell or neural network. A number of embodiments discussed above specifically mention the mammalianized NpHR sequence (GenBank Accession No. EF474018). In connection with the present invention, it has been discovered that this mammalianized NpHR coding sequence has a toxicity that is nearly 100%. It has been discovered that for high expression levels the mammalianized NpHR sequence manifests toxicity at 87% which is considered near enough complete toxicity to be considered as a baseline toxicity reference level which can be substantially reduced using different (NpHR-based but having a different NpHR-based sequence) molecules. Accordingly, various aspects of the present invention are implemented with significantly reduced toxicity.

The toxicity levels were obtained by a stringent process of identifying any cell abnormality, such as blebs on the cell membrane. For the purposes of this disclosure and the data presented herein, a cell with even single abnormality is considered toxic as are any dead cells. A "toxicity level," as used in this disclosure, means the percentage of cells that are considered toxic.

As discussed herein, the expression levels are obtained by increasing the original expression levels discussed above (i.e., about 2×10e7 infectious units (ifu) per milliliter) to one of high expression of at least 3×10e7 ifu per milliliter; very high expression of at least 4×10e7 ifu per milliliter; ultra high expression of at least 5×10e7 ifu per milliliter; or very ultra high expression of at least 1×10e8 ifu per milliliter. In a particular embodiment the expression levels can characterized in terms of their mean photo current being 44 pA or higher.

Various embodiments of the present invention allow for substantially reduced toxicity levels in high expression level (relative to the mammalianized NpHR sequence).

According to one embodiment, an opsin sequence is implemented that exhibits a toxicity of about 72%. A specific example is SPChR2-NpHR (SEQ ID NO 7), where a signal peptide (first 15aa) from ChR2 is added to the N-terminus (SEQ ID NO 11): DYGGALSAVGRELL.

According to one embodiment, an opsin sequence is implemented that exhibits a toxicity of about 69%. A specific example is SPnAChR-L-NpHR (SEQ ID NO 8), where signal peptide (23aa) from nicotinic acetylcholine receptor is added to the N-terminus (SEQ ID NO 12): MGLRALML-WLLAAAGLVRESLQG.

According to one embodiment, an opsin sequence is implemented that exhibits a toxicity of about 59%. A specific example is NpHR-VSNL (SEQ ID NO 9), where the PDZ binding motif (SEQ ID NO 24) VSNL is added to the C-terminus.

According to one embodiment, an NpHR coding sequence is implemented with a toxicity of about half of the base-line toxicity. A specific example is an NpHR-based sequence that uses the codons originally present in *Natronomonas pharaonis*. Another example is an NpHR-based sequence where a signal peptide (18aa) from nicotinic acetylcholine receptor is added to the N-terminus (SEQ ID NO 13): MRGTPLLLVVSLFSLLQD.

According to another embodiment, an NpHR coding sequence is implemented with a toxicity of between about 34% and 40%. A specific example is an NpHR-based sequence that is formed by adding the PDZ binding motif (SEQ ID NO 14) ETQZ to the C-terminus (NpHR-ETQV).

According to another embodiment, an NpHR coding sequence is implemented with a toxicity of between about 20% and 26%. A specific example is an NpHR-based sequence that is formed by adding the (SEQ ID NO 15) PTPP sequence to the C-terminus to promote interaction with actin-binding protein filamin (NpHR-actin).

According to another embodiment, an NpHR coding sequence is implemented with a peak current of between about 49 pA and 77 pA. A specific example is an NpHR-based sequence that is formed by adding the PDZ binding motif (SEQ ID NO 14) ETQZ to the C-terminus (NpHR-ETQV).

According to another embodiment, an NpHR coding sequence is implemented with a peak current of between about 11 pA and 70 pA. A specific example is an NpHR-based sequence that is formed by adding the (SEQ ID NO 15) PTPP sequence to the C-terminus to promote interaction with actin-binding protein filamin (NpHR-actin). Another example is an NpHR-based sequence that is formed by adding the ER export signal to the C-terminus: VLGSL or, more generally, (SEQ ID NO 17) VXXSL (NpHR-ERexport).

Experimental data results showing toxicity and peak current for various NpHR sequences are shown in Table 2.

TABLE 2

| Construct | Molecular Modification | Toxicity in neurons | Peak photocurrent (mean ± s.d) |
|---|---|---|---|
| Humanized NpHR (SEQ ID NO 1) | none | 87% | 48.0 ± 7.0 pA |
| Non-Humanized NpHR (SEQ ID NO 2) | use the original codons from bacteria | 37% | 29.6 ± 18.5 pA |
| $SP_{nAChR-S}$-NpHR (SEQ ID NO 3) | Added signal peptide (18aa) from nicotinic acetylcholine receptor to the N-terminus: MRGTPLLLVVSLFSLLQD | 37% | 51.5 ± 9.2 pA |
| NpHR-ETQV (SEQ ID NO 4) | Added the PDZ binding motif ETQV to the C-terminus | 34% | 63.7 ± 12.7 pA |
| NpHR-actin (SEQ ID NO 5) | Added the PTPP sequence to the C-terminus to promote interaction with actin-binding protein filamin | 23% | 39.8 ± 20.2 pA |
| NpHR-ERexport (SEQ ID NO 6) | Added the ER export signal to the C-terminus: VLGSL (more general VXXSL) | 7% | 40.3 ± 28.5 pA |

According to another embodiment, an NpHR coding sequence is implemented with a toxicity of between about 4% and 10%. A specific example is an NpHR-based sequence that is formed by adding the ER export signal to the C-terminus: (SEQ ID NO 16) VLGSL or, more generally, (SEQ ID NO 17) VXXSL (NpHR-ERexport).

According to another embodiment, an NpHR coding sequence is implemented with a peak current of between about 11.1 pA and 50 pA. A specific example is an NpHR-based sequence that uses the codons originally present in *Natronomonas pharaonis.*

According to another embodiment, an NpHR coding sequence is implemented with a peak current of between about 40 pA and 61 pA. A specific example is an NpHR-based sequence where a signal peptide (18aa) from nicotinic acetylcholine receptor is added to the N-terminus: (SEQ ID NO 13) MRGTPLLLVVSLFSLLQD.

Toxicity was assessed in cultured hippocampal neurons as follows: neurons 4 days in vitro were infected with lentivirus for each of the constructs and allowed to accumulate protein for two weeks before assessing toxicity. Cells that displayed large round intracellular blobs either in the soma or dendrites were counted as toxic cells. The photocurrents for each of the constructs were assessed by electrophysiology as described herein and also similar to that taught by "Multimodal fast optical interrogation of neural circuitry" by Zhang, et al, Nature (Apr. 5, 2007) Vol. 446: 633-639, which is fully incorporated herein by reference. It should be noted that while the neurons were allowed to express protein for at least one week, this time frame was about half of the time allotted in various underlying experimental tests discussed above. Additional expression time would allow for more expression, which in turn would result in increased toxicity and photo-currents. Accordingly, assuming a near-linear increase in toxicity, the embodiments showing around 37% toxicity would reach about 74%.

Various embodiments are directed toward a construct that includes ER export signals, including, but not limited to: (SEQ ID NO 17) VXXSL; (SEQ ID NO 18) FXYENE (see "A sequence motif responsible for ER export and surface expression of Kir2.0 inward rectifier K(+) channels" Stockklausner et al., FEBS Lett.; 493 (2-3):129-133 March, 2001; and "Role of ER Export Signals in Controlling Surface Potassium Channel Numbers" Ma et al., Science Vol. 291. no. 5502:316-319, 2001); C-terminal valine residue (see "A Specific Endoplasmic Reticulum Export Signal Drives Transport of Stem Cell Factor (Kitl) to the Cell Surface" Paulhe et al., J. Biol. Chem., Vol. 279, Issue 53, 55545-55555, Dec. 31, 2004); VMI (see "Signal-dependent export of GABA transporter 1 from the ER-Golgi intermediate compartment is specified by a C-terminal motif" Farhan et al., J. Cell Sci. 121:753-761, Feb. 19, 2008.) Each of the above-mentioned references is incorporated herein by reference in their entirety.

Various embodiments are directed toward a construct that includes signal peptides for insertion into plasma membrane including, but not limited to, signal peptides from other opsins or from other transmembrane proteins such as the nicotinic acetylcholine receptor (Isenberg et al., 1989, J. Neurochemistry).

For additional information regarding implementation of a signal peptide (first 15aa) from ChR2 added to the N-terminus reference can be made to "Millisecond-timescale, genetically-targeted optical control of neural activity" Boyden, et al., Nature Neuroscience 8(9):1263-1268 (2005), which is fully incorporated herein by reference.

For additional information regarding implementation of a signal peptide (23aa) from nicotinic acetylcholine receptor added to the N-terminus reference can be made to Bocquet et al., "A prokaryotic proton-gated ion channel from the nicotinic acetylcholine receptor family" Nature 445:116-119, January, 2007.

Various embodiments are directed toward a construct that includes PDZ binding motifs including, but not limited to, (SEQ ID NOS 19-20) X(S/T)XV (SEQ ID NO 21) ETQV) or (SEQ ID NOS 22-23) X(S/T)XL (e.g., VSNL).

For additional information regarding implementation of NpHR-VSNL, where the PDZ binding motif VSNL is added to the C-terminus, reference can be made to "Interactions with PDZ proteins are required for L-type calcium channels to activate cAMP response element-binding protein-dependent gene expression" Weick et al., J. Neurosci. 23:3446-3456, 2003, which is fully incorporated herein by reference.

For additional information regarding implementation of NpHR-ETQV-based sequences, reference can be made to "Targeting and Readout Strategies for Fast Optical Neural Control In Vitro and In Vivo" Gradinaru, et al., The Journal of Neuroscience 27(52):14231-14238, Dec. 26, 2007, which is fully incorporated herein by reference.

For additional information regarding implementation of original codon-based sequences, reference can be made to "Light Driven Proton Pump or Chloride Pump by Halorhodopsin" Bamberg, et al., Proc. Natl. Acad. Sci. USA Vol. 90: 639-643, January 1993 Biophysics, which is fully incorporated herein by reference.

For additional information regarding implementation of $SP_{nAchR-S}$-pHR-based sequences, reference can be made to "Rapid Communication Cloning of a Putative Neuronal Nicotinic Acetylcholine Receptor Subunit" Isenberg, et al., J. Neurochem. 52(3):988-991, 1989, which is fully incorporated herein by reference.

For additional information regarding implementation of NpHR-actin-based sequences, reference can be made to "Localization and Enhanced Current Density of the Kv4.2 Potassium Channel by Interaction with the Actin-binding Protein Filamin" Petrecca, et al., The Journal of Neuroscience 20(23):8763-8744, December, 2000, which is fully incorporated herein by reference.

For additional information regarding implementation of ERexport-based sequences, reference can be made to "Surface Expression of Kv1 Voltage-Gated K+ Channels is Governed by a C-terminal Motif" Levitan, et al., TCM 10(7):317-320, 2000, which is fully incorporated herein by reference.

The various sequences need not be implemented in isolation. To the contrary, embodiments of the present invention involve various combinations of the above sequences with one another on the same gene. For example, the desired expression levels, peak currents and toxicity levels are tailored through a combination of two or more different sequences within the target cellular structure(s). Specific embodiments involve the selection and use of specific sequences that bind to different portions of the gene (e.g., the C-terminus and the N-terminus). Such selections results in characteristics (e.g., toxicity, current levels and expression levels) not present in embodiments that use only a single sequence. Thus, various embodiments are directed toward combinations of two or more of the above listed modifications. For example, a hybrid construct of $SP_{nAChR-S}$-NpHR-ERexport (SEQ ID NO 10). Another example involves the addition of ChR2 to the cell.

Thus, various embodiments can be implemented in which two or more constructs are used to express an NpHR-based protein in the cell. Each construct is capable of independently expressing the protein. In one instance, the constructs can be implemented in the same sequence. In another instance, the constructs can be sequentially delivered using two or more different sequences.

Additional constructs can be implemented by co-expressing helper proteins, such as chaperones, that could be useful in aiding NpHR folding and trafficking.

A few example sequence listings are provided in the Appendix, which forms part of this specification. It should be noted that all the sequences contain the EYFP fluorescent protein for visualization purposes. Embodiments of the present invention can be implemented without this EYFP fluorescent protein. For example, each of the sequences can be implemented either on the NpHR alone (with no fluorescent protein) or on the NpHR-X fluorescent protein complex.

Many human applications of the present invention require governmental approval prior to their use. For instance, human use of gene therapy may require such approval. However, similar gene therapies in neurons (nonproliferative cells that are non-susceptible to neoplasms) are proceeding rapidly, with active, FDA-approved clinical trials already underway involving viral gene delivery to human brains. This is likely to facilitate the use of various embodiments of the present invention for a large variety of applications. The following is a non-exhaustive list of a few examples of such applications and embodiments.

Addiction is associated with a variety of brain functions, including reward and expectation. Additionally, the driving cause of addiction may vary between individuals. According to one embodiment, addiction, for example nicotine addiction, may be treated with optogenetic stabilization of small areas on the insula. Optionally, functional brain imaging—for example cued-state PET or fMRI—may be used to locate a hypermetabolic focus in order to determine a precise target spot for the intervention on the insula surface.

Optogenetic excitation of the nucleus accumbens and septum may provide reward and pleasure to a patient without need for resorting to use of substances, and hence may hold a key to addiction treatment. Conversely, optogenetic stabilization of the nucleus accumbens and septum may be used to decrease drug craving in the context of addiction. In an alternative embodiment, optogenetic stabilization of hypermetabolic activity observed at the genu of the anterior cingulate (BA32) can be used to decrease drug craving. Optogenetic stabilization of cells within the arcuate nucleus of the medial hypothalamus which contain peptide products of pro-opiomelanocortin (POMC) and cocaine-and-amphetamine-regulating transcript (CART) can also be used to decrease drug addiction behavior. For further information in this regard, reference may be made to: Naqvi N H, Rudrauf D, Damasio H, Bechara A. "Damage to the insula disrupts addiction to cigarette smoking." Science. 2007 Jan. 26; 315(5811):531-534, which is fully incorporated herein by reference.

Optogenetic stimulation of neuroendocrine neurons of the hypothalamic periventricular nucleus that secrete somatostatin can be used to inhibit secretion of growth hormone from the anterior pituitary, for example in acromegaly. Optogenetic stabilization of neuroendocrine neurons that secrete somatostatin or growth hormone can be used to increase growth and physical development. Among the changes that accompany "normal" aging, is a sharp decline in serum growth hormone levels after the 4$^{th}$ and 5$^{th}$ decades. Consequently, physical deterioration associated with aging may be lessened through optogenetic stabilization of the periventricular nucleus.

Optogenetic stabilization of the ventromedial nucleus of the hypothalamus, particularly the pro-opiomelanocortin (POMC) and cocaine-and-amphetamine-regulating transcript (CART) of the arcuate nucleus, can be used to increase appetite, and thereby treat anorexia nervosa. Alternatively, optogenetic stimulation of the lateral nuclei of the hypothalamus can be used to increase appetite and eating behaviors.

Optogenetic excitation in the cholinergic cells of affected areas including the temporal lobe, the NBM (Nucleus basalis of Meynert) and the posterior cingulate gyrus (BA 31) provides stimulation, and hence neurotrophic drive to deteriorating areas. Because the affected areas are widespread within the brain, an analogous treatment with implanted electrodes may be less feasible than an opto-genetic approach.

Anxiety disorders are typically associated with increased activity in the left temporal and frontal cortex and amygdala, which trends toward normal as anxiety resolves. Accordingly, the affected left temporal and frontal regions and amygdala may be treated with optogenetic stabilization, so as to dampen activity in these regions.

In normal physiology, photosensitive neural cells of the retina, which depolarize in response to the light that they receive, create a visual map of the received light pattern. Optogenetic ion channels can be used to mimic this process in many parts of the body, and the eyes are no exception. In the case of visual impairment or blindness due to damaged retina, a functionally new retina can be grown, which uses natural ambient light rather than flashing light patterns from an implanted device. The artificial retina grown may be placed in the location of the original retina (where it can take advantage of the optic nerve serving as a conduit back to the visual cortex). Alternatively, the artificial retina may be placed in another location, such as the forehead, provided that a conduit for the depolarization signals are transmitted to cortical tissue capable of deciphering the encoded information from the optogenetic sensor matrix. Cortical blindness could also be treated by simulating visual pathways downstream of the visual cortex. The stimulation would be based on visual data produced up stream of the visual cortex or by an artificial light sensor.

Treatment of tachycardia may be accomplished with optogenetic stimulation to parasympathetic nervous system fibers including CN X or Vagus Nerve. This causes a decrease in the SA node rate, thereby decreasing the heart rate and force of contraction. Similarly, optogenetic stabilization of sympathetic nervous system fibers within spinal nerves T1 through T4, serves to slow the heart. For the treatment of pathological bradycardia, optogenetic stabilization of the Vagus nerve, or optogenetic stimulation of sympathetic fibers in T1 through T4 will serve to increase heart rate. Cardiac disrhythmias resulting from aberrant electrical foci that outpace the sinoatrial node may be suppressed by treating the aberrant electrical focus with moderate optogenetic stabilization. This decreases the intrinsic rate of firing within the treated tissue, and permits the sinoatrial node to regain its role in pacing the heart's electrical system. In a similar way, any type of cardiac arrhythmia could be treated. Degeneration of cardiac tissue that occurs in cardiomyopathy or congestive heart failure could also be treated using this invention; the remaining tissue could be excited using various embodiments of the invention.

Optogenetic excitation stimulation of brain regions including the frontal lobe, parietal lobes and hippocampi, may increase processing speed, improve memory, and stimulate growth and interconnection of neurons, including spurring development of neural progenitor cells. As an example, one such application of the present invention is directed to optogenetic excitation stimulation of targeted neurons in the thalamus for the purpose of bringing a patient out of a near-vegetative (barely-conscious) state. Growth of light-gated ion channels or pumps in the membrane of targeted thalamus neurons is effected. These modified neurons are then stimulated, e.g., via optics which may also gain access by the same passageway, by directing a flash of light thereupon so as to modulate the function of the targeted neurons and/or surrounding cells. For further information regarding appropriate modulation techniques (via electrode-based treatment) or further information regarding the associated brain regions for such patients, reference may be made to: Schiff N D, Giacino J T, Kalmar K, Victor J D, Baker K, Gerber M, Fritz B, Eisenberg B, O'Connor J O, Kobylarz E J, Farris S, Machado A, McCagg C, Plum F, Fins J J, Rezai A R. Behavioral improvements with thalamic stimulation after severe traumatic brain injury. Nature. Vol 448. Aug. 2, 2007 pp 600-604.

In an alternative embodiment, optogenetic excitation may be used to treat weakened cardiac muscle in conditions such as congestive heart failure. Electrical assistance to failing heart muscle of CHF is generally not practical, due to the thin-stretched, fragile state of the cardiac wall, and the difficulty in providing an evenly distributed electrical coupling between an electrodes and muscle. For this reason, preferred methods to date for increasing cardiac contractility have involved either pharmacological methods such as Beta agonists, and mechanical approaches such as ventricular assist devices. In this embodiment of the present invention, optogenetic excitation is delivered to weakened heart muscle via light emitting elements on the inner surface of a jacket surround the heart or otherwise against the affected heart wall. Light may be diffused by means well known in the art, to smoothly cover large areas of muscle, prompting contraction with each light pulse.

Optogenetic stabilization in the subgenual portion of the cingulate gyrus (Cg25), yellow light may be applied with an implanted device. The goal would be to treat depression by suppressing target activity in manner analogous to what is taught by Mayberg H S et al., Deep Brain Stimulation for Treatment-Resistant Depression. Neuron, Vol. 45, 651-660, Mar. 3, 2005, 651-660, which is fully incorporated herein by reference. In an alternative embodiment, an optogenetic excitation stimulation method is to increase activity in that region in a manner analogous to what is taught by Schlaepfer et al., Deep Brain stimulation to Reward Circuitry Alleviates Anhedonia in Refractory Major Depression, Neuropsychopharmacology 2007 1-10, which is fully incorporated herein by reference. In yet another embodiment the left dorsolateral prefrontal cortex (LDPFC) is targeted with an optogenetic excitation stimulation method. Pacing the LDLPFC at 5-20 Hz serves to increase the basal metabolic level of this structure which, via connecting circuitry, serves to decrease activity in Cg 25, improving depression in the process. Suppression of the right dorsolateral prefrontal cortex (RDLPFC) is also an effective depression treatment strategy. This may be accomplished by optogenetic stabilization on the RDLPFC, or suppression may also be accomplished by using optogenetic excitation stimulation, and pulsing at a slow rate—1 Hz or less, improving depression in the process. Vagus nerve stimulation (VNS) may be improved using an optogenetic approach. Use of optogenetic excitation may be used in order to stimulate only the vagus afferents to the brain, such as the nodose ganglion and the jugular ganglion. Efferents from the brain would not receive stimulation by this approach, thus eliminating some of the side-effects of VNS including discomfort in the throat, a cough, difficulty swallowing and a hoarse voice. In an alternative embodiment, the hippocampus may be optogenetically excited, leading to increased dendritic and axonal sprouting, and overall growth of the hippocampus. Other brain regions implicated in depression that could be treated using this invention include the amygdala, accumbens, orbitofrontal and orbitomedial cortex, hippocampus, olfactory cortex, and dopaminergic, serotonergic, and noradrenergic projections. Optogenetic approaches could be used to control spread of activity through structures like the hippocampus to control depressive symptoms.

So long as there are viable alpha and beta cell populations in the pancreatic islets of Langerhans, the islets can be targeted for the treatment of diabetes. For example, when serum glucose is high (as determined manually or by closed loop glucose detection system), optogenetic excitation may be used to cause insulin release from the beta cells of the islets of Langerhans in the pancreas, while optogenetic stabilization is used to prevent glucagon release from the alpha cells of the islets of Langerhans in the pancreas. Conversely, when blood sugars are too low (as determined manually or by closed loop glucose detection system), optogenetic stabilization may be used to stop beta cell secretion of insulin, and optogenetic excitation may be used to increase alpha-cell secretion of glucagon.

For treatment of epilepsy, quenching or blocking epileptogenic activity is amenable to optogenetic approaches. Most epilepsy patients have a stereotyped pattern of activity spread resulting from an epileptogenic focus Optogenetic stabilization could be used to suppress the abnormal activity before it spreads or truncated it early in its course. Alternatively, activation of excitatory tissue via optogenetic excitation stimulation could be delivered in a series of deliberately asynchronous patterns to disrupt the emerging seizure activity. Another alternative involves the activation of optogenetic excitation stimulation in GABAergic neurons to provide a similar result. Thalamic relays may be targeted with optogenetic stabilization triggered when an abnormal EEG pattern is detected.

Another embodiment involves the treatment of gastrointestinal disorders. The digestive system has its own, semi-autonomous nervous system containing sensory neurons, motor neurons and interneurons. These neurons control movement of the GI tract, as well as trigger specific cells in the gut to release acid, digestive enzymes, and hormones including gastrin, cholecystokinin and secretin. Syndromes that include inadequate secretion of any of these cellular products may be treated with optogenetic stimulation of the producing cell types, or neurons that prompt their activity. Conversely, optogenetic stabilization may be used to treat syndromes in which excessive endocrine and exocrine products are being created. Disorders of lowered intestinal motility, ranging from constipation (particularly in patients with spinal cord injury) to megacolan may be treated with optogenetic excitation of motor neurons in the intestines. Disorders of intestinal hypermotility, including some forms of irritable bowel syndrome may be treated with optogenetic stabilization of neurons that control motility. Neurogentic gastric outlet obstructions may be treated with optogenetic stabilization of neurons and musculature in the pyloris. An alternative approach to hypomobility syndromes would be to provide optogenetic excitation to stretch-sensitive neurons in the walls of the gut, increasing the signal that the gut is full and in need of emptying.

In this same paradigm, an approach to hypermobility syndromes of the gut would be to provide optogenetic stabilization to stretch receptor neurons in the lower GI, thus providing a “false cue” that the gut was empty, and not in need of emptying. In the case of frank fecal incontinence, gaining improved control of the internal and external sphincters may be preferred to slowing the motility of the entire tract. During periods of time during which a patient needs to hold feces in, optogenetic excitation of the internal anal sphincter will provide for retention. Providing optogenetic stimulation to the external sphincter may be used to provide additional continence. When the patient is required to defecate, the internal anal sphincter, and then external anal sphincter should be relaxed, either by pausing the optogenetic stimulation, or by adding optogenetic stabilization.

Conductive hearing loss may be treated by the use of optical cochlear implants. Once the cochlea has been prepared for optogenetic stimulation, a cochlear implant that flashes light may be used. Sensorineural hearing loss may be treated through optical stimulation of downstream targets in the auditory pathway.

Another embodiment of the present invention is directed toward the treatment of blood pressure disorders, such as hypertension. Baroreceptors and chemoreceptors in regions such as the aorta (aortic bodies and paraaortic bodies) and the carotid arteries (“carotic bodies”) participate the regulation of blood pressure and respiration by sending afferents via the vagus nerve (CN X), and other pathways to the medulla and pons, particularly the solitary tract and nucleus. Optogenetic excitation of the carotid bodies, aortic bodies, paraortic bodies, may be used to send a false message of “hypertension” to the solitary nucleus and tract, causing it to report that blood pressure should be decreased. Optogenetic excitation or stabilization directly to appropriate parts of the brainstem may also be used to lower blood pressure. The opposite modality causes the optogenetic approach to serve as a pressor, raising blood pressure. A similar effect may also be achieved via optogenetic excitation of the Vagus nerve, or by optogenetic stabilization of sympathetic fibers within spinal nerves T1-T4. In an alternative embodiment, hypertension may be treated with optogenetic stabilization of the heart, resulting in decreased cardiac output and lowered blood pressure. According to another embodiment, optogentic stabilization of aldosterone-producing cells within the adrenal cortex may be used to decrease blood pressure. In yet another alternative embodiment, hypertension may be treated by optogenetic stabilization of vascular smooth muscle. Activating light may be passed transcutaneously to the peripheral vascular bed.

Another example embodiment is directed toward the treatment of hypothalamic-pituitary-adrenal axis disorders. In the treatment of hypothyroidism, optogenetic excitation of parvocellular neuroendocrine, neurons in the paraventricular and anterior hypothalamic nuclei can be used to increase secretion of thyrotropin-releasing hormone (TRH). TRH, in turn, stimulates anterior pituitary to secrete TSH. Conversely, hyperthyroidism may be treated with optogenetic stabilization of the provocellular neuroendocrine neurons. For the treatment of adrenal insufficiency, or of Addison's disease, optogenetic excitation of parvocellular neuroendocrine neurons in the supraoptic nucleus and paraventricular nuclei may be used to increase the secretion of vasopressin, which, with the help of corticotropin-releasing hormone (CRH), stimulate anterior pituitary to secrete ACTH. Cushing syndrome, frequently caused by excessive ACTH secretion, may be treated with optogenetic stabilization of the parvocellular neuroendocrine neurons of supraoptic nucleus via the same physiological chain of effects described above. Neuroendocrine neurons of the arcuate nucleus produce dopamine, which inhibits secretion of prolactin from the anterior pituitary. Hyperprolactinemia can therefore be treated via optogenetic excitation, while hypoprolactinemia can be treated with optogenetic stabilization of the neuroendocrine cells of the arcuate nucleus.

In the treatment of hyperautonomic states, for example anxiety disorders, optogenetic stabilization of the adrenal medulla may be used to reduce norepinephrine output. Similarly, optogenetic stimulation of the adrenal medulla may be used in persons with need for adrenaline surges, for example those with severe asthma, or disorders that manifest as chronic sleepiness.

Optogenetic stimulation of the adrenal cortex will cause release of chemicals including cortisol, testosterone, and aldosterone. Unlike the adrenal medualla, the adrenal cortex receives its instructions from neuroendocrine hormones secreted from the pituitary and hypothalamus, the lungs, and the kidneys. Regardless, the adrenal cortex is amenable to optogenetic stimulation. Optogenetic stimulation of the cortisol-producing cells of the adrenal cortex may be used to treat Addison's disease. Optogenetic stabilization of cortisol-producing cells of the adrenal cortex may be used to treat Cushing's disease. Optogenetic stimulation of testosterone-producing cells may be used to treat disorders of sexual interest in women: Optogenetic stabilization of those same cells may be used to decrease facial hair in women. Optogenetic stabilization of aldosterone-producing cells within the adrenal cortex may be used to decrease blood pressure. Optogenetic excitation of aldosterone-producing cells within the adrenal cortex may be used to increase blood pressure.

Ontogenetic excitation stimulation of specific affected brain regions may be used to increase processing speed, and stimulate growth and interconnection of neurons, including spurring the maturation of neural progenitor cells. Such uses can be particularly useful for treatment of mental retardation.

According to another embodiment of the present invention, various muscle diseases and injuries can be treated. Palsies related to muscle damage, peripheral nerve damage and to dystrophic diseases can be treated with optogenetic excitation to cause contraction, and optogenetic stabilization to cause relaxation. This latter relaxation via optogenetic stabilization approach can also be used to prevent muscle wasting, maintain tone, and permit coordinated movement as opposing muscle groups are contracted. Likewise, frank spasticity can be treated via optogenetic stabilization.

In areas as diverse as peripheral nerve truncation, stroke, traumatic brain injury and spinal cord injury, there is a need to foster the growth of new neurons, and assist with their integration into a functional network with other neurons and with their target tissue. Re-growth of new neuronal tracts may be encouraged via optogenetic excitation, which serves to signal stem cells to sprout axons and dendrites, and to integrate themselves with the network. Use of an optogenetic technique (as opposed to electrodes) prevents receipt of signals by intact tissue, and serves to ensure that new target tissue grows by virtue of a communication set up with the developing neurons, and not with an artificial signal like current emanating from an electrode.

Obesity can be treated with optogenetic excitation to the ventromedial nucleus of the hypothalamus, particularly the pro-opiomelanocortin (POMC) and cocaine-and-amphetamine-regulating transcript (CART) of the arcuate nucleus. In an alternative embodiment, obesity can be treated via optogenetic stabilization of the lateral nuclei of the hypothalamus. In another embodiment, optogenetic stimulation to leptin-producing cells, or to cells with leptin receptors within the hypothalamus may be used to decrease appetite and hence treat obesity.

Destructive lesions to the anterior capsule, and analogous DBS to that region are established means of treating severe, intractable obsessive-compulsive disorder 48 (OCD48). Such approaches may be emulated using optogenetic stabilization to the anterior limb of the internal capsule, or to regions such as BA32 and Cg24 which show metabolic decrease as OCD remits.

Chronic Pain can be treated using another embodiment of the present invention. Electrical stimulation methods include local peripheral nerve stimulation, local cranial nerve stimulation and "subthreshold" motor cortex stimulation. Reasonable optogentic approaches include optogenetic stabilization at local painful sites. Attention to promoter selection would ensure that other sensory and motor fibers would be unaffected. Selective optogenetic excitation of interneurons at the primary motor cortex also may provide effective pain relief. Also, optogenetic stabilization at the sensory thalamus, (particularly medial thalamic nuclei), periventricular grey matter, and ventral raphe nuclei, may be used to produce pain relief. In an alternative embodiment, optogenetic stabilization of parvalbumin-expressing cells targeting as targeting strategy, may be used to treat pain by decreasing Substance P production. The release of endogenous opioids may be accomplished by using optogenetic excitation to increase activity in the nucleus accumbens. In an alternative embodiment, when POMC neurons of the arcuate nucleus of the medial hypothalamus are optogenetically excited, beta endorphin are increased, providing viable treatment approaches for depression and for chronic pain.

Parkinson's Disease can be treated by expressing optogenetic stabilization in the glutamatergic neurons in either the subthalamic nucleus (STN) or the globus pallidus interna (GPi) using an excitatory-specific promoter such as CaMKIIα, and apply optogenetic stabilization. Unlike electrical modulation in which all cell-types are affected, only glutamatergic STN neurons would be suppressed.

Certain personality disorders, including the borderline and antisocial types, demonstrate focal deficits in brain disorders including "hypofrontality." Direct or indirect optogenetic excitation of these regions is anticipated to produce improvement of symptoms. Abnormal bursts of activity in the amygdala are also known to precipitate sudden, unprompted flights into rage: a symptom of borderline personality disorder, as well as other conditions, which can benefit from optogenetic stabilization of the amygdala. Optogenetic approaches could improve communication and synchronization between different parts of the brain, including amygdala, striatum, and frontal cortex, which could help in reducing impulsiveness and improving insight.

The amygdalocentric model of post-traumatic-stress disorder (PTSD) proposes that it is associated with hyperarousal of the amygdala and insufficient top-down control by the medial prefrontal cortex and the hippocampus. Accordingly, PTSD may be treated with optoeenetic stabilization of the amyedale or hippocampus.

Schizophrenia is characterized by abnormalities including auditory hallucinations. These might be treated by suppression of the auditory cortex using optogenetic stabilization. Hypofrontality associated with schizophrenia might be treated with optogenetic excitation in the affected frontal regions. Optogenetic approaches could improve communication and synchronization between different parts of the brain which could help in reducing misattribution of self-generated stimuli as foreign.

Optogenetic stabilization of cells within the arcuate nucleus of the medial hypothalamus, which contain peptide products of pro-opiomelanocortin (POMC) and cocaine-and-amphetamine-regulating transcript (CART) can be used to reduce compulsive sexual behavior. Optogentic excitation of cells within the arcuate nucleus of the medial hypothalamus which contain peptide products of pro-opiomelanocortin (POMC) and cocaine-and-amphetamine-regulating transcript (CART) may be used to increase sexual interest in the treatment of cases of disorders of sexual desire. In the treatment of disorders of hypoactive sexual desire testosterone production by the testes and the adrenal glands can be increased through optogenetic excitation of the pituitary gland. Optogentic excitation of the nucleus accumbens can be used for the treatment of anorgasmia.

The suprachiasmatic nucleus secretes melatonin, which serves to regulate sleep/wake cycles. Optogenetic excitation to the suprachiasmic nucleus can be used to increase melatonin production, inducing sleep, and thereby treating insomnia. Orexin (hypocretin) neurons strongly excite numerous brain nuclei in order to promote wakefulness. Optogentetic excitation of orexin-producing cell populations can be used to treat narcolepsy, and chronic daytime sleepiness.

Optogenetic stimulation of the supraoptic nucleus may be used to induce secretion of oxytocin, can be used to promote parturition during childbirth, and can be used to treat disorders of social attachment.

Like muscular palsies, the motor functions that have been de-afferented by a spinal cord injury may be treated with optogenetic excitation to cause contraction, and optogenetic stabilization to cause relaxation. This latter relaxation via optogenetic stabilization approach may also be used to prevent muscle wasting, maintain tone, and permit coordinated movement as opposing muscle groups are contracted. Likewise, frank spasticity may be treated via optogenetic stabilization. Re-growth of new spinal neuronal tracts may be encouraged via optogenetic excitation, which serves to signal stem cells to sprout axons and dendrites, and to integrate themselves with the network.

Stroke deficits include personality change, motor deficits, sensory deficits, cognitive loss, and emotional instability. One strategy for the treatment of stroke deficits is to provide optogenetic stimulation to brain and body structures that have been deafferented from excitatory connections. Similarly, optogenetic stabilization capabilities can be imparted on brain and body structures that have been deafferented from inhibitory connections.

Research indicates that the underlying pathobiology in Tourette's syndrome is a phasic dysfunction of dopamine transmission in cortical and subcortical regions, the thalamus, basal ganglia and frontal cortex. In order to provide therapy, affected areas are preferably first identified using techniques including functional brain imaging and magnetoencephalography (MEG). Whether specifically identified or not, optogenetic stabilization of candidate tracts may be used to suppress motor tics. Post-implantation empirical testing of device parameters reveals which sites of optogenetic stabilization, and which are unnecessary to continue.

In order to treat disorders of urinary or fecal incontinence optogenetic stabilization can be used to the sphincters, for example via optogenetic stabilization of the bladder detrussor smooth muscle or innervations of that muscle. When micturation is necessary, these optogenetic processes are turned off, or alternatively can be reversed, with optogenetic stabilization to the (external) urinary sphincter, and optogenetic excitation of the bladder detrussor muscle or its innervations. When a bladder has been deafferentated, for example, when the sacral dorsal roots are cut or destroyed by diseases of the dorsal roots such as tabes dorsalis in humans, all reflex contractions of the bladder are abolished, and the bladder becomes distended. Optogenetic excitation of the muscle directly can be used to restore tone to the detrussor, prevent kidney damage, and to assist with the micturition process. As the bladder becomes "decentralized" and hypersensitive to movement, and hence prone to incontinence, optogenetic stabilization to the bladder muscle can be used to minimize this reactivity of the organ.

In order to selectively excite/inhibit a given population of neurons, for example those involved in the disease state of an illness, several strategies can be used to target the optogenetic proteins/molecules to specific populations.

For various embodiments of the present invention, genetic targeting may be used to express various optogenetic proteins or molecules. Such targeting involves the targeted expression of the optogenetic proteins/molecules via genetic control elements such as promoters (e.g., Parvalbumin, Somatostatin, Cholecystokinin, GFAP), enhancers/silencers (e.g., Cytomaglovirus Immediate Early Enhancer), and other transcriptional or translational regulatory elements (e.g. Woodchuck Hepatitis Virus Post-transcriptional Regulatory Element). Permutations of the promoter+enhancer+regulatory element combination can be used to restrict the expression of optogenetic probes to genetically-defined populations.

Various embodiments of the present invention may be implemented using spatial/anatomical targeting. Such targeting takes advantage of the fact that projection patterns of neurons, virus or other reagents carrying genetic information (DNA plasmids, fragments, etc), can be focally delivered to an area where a given population of neurons project to. The genetic material will then be transported back to the bodies of the neurons to mediate expression of the optogenetic probes. Alternatively, if it is desired to label cells in a focal region, viruses or genetic material may be focally delivered to the interested region to mediate localized expression.

Various gene delivery systems are useful in implementing one or more embodiments of the present invention. One such delivery system is Adeno-Associated Virus (AAV). AAV can be used to deliver a promoter+optogenetic probe cassett to a specific region of interest. The choice of promoter will drive expression in a specific population of neurons. For example, using the CaMKIIa promoter will drive excitatory neuron specific expression of optogenetic probes. AAV will mediate long-term expression of the optogenetic probe for at least 1 year or more. To achieve more specificity, AAV may be pseudotyped with specific serotypes 1 to 8, with each having different trophism for different cell types. For instance, serotype 2 and 5 is known to have good neuron-specific trophism.

Another gene deliver mechanism is the use of a retrovirus. HIV or other lentivirus-based retroviral vectors may be used to deliver a promoter+optogenetic probe cassette to a specific region of interest. Retroviruses may also be pseudotyped with the Rabies virus envelope glycoprotein to achieve retrograde transport for labeling cells based on their axonal projection patterns. Retroviruses integrate into the host cell's genome, therefore are capable of mediating permanent expression of the optogenetic probes. Non-lentivirus based retroviral vectors can be used to selectively label dividing cells.

Gutless Adenovirus and Herpes Simplex Virus (HSV) are two DNA based viruses that can be used to deliver promoter+optogenetic probe cassette into specific regions of the brain as well. HSV and Adenovirus have much larger packaging capacities and therefore can accommodate much larger promoter elements and can also be used to deliver multiple optogenetic probes or other therapeutic genes along with optogenetic probes.

Focal Electroporation can also be used to transiently transfect neurons. DNA plasmids or fragments can be focally delivered into a specific region of the brain. By applying mild electrical current, surrounding local cells will receive the DNA material and expression of the optogenetic probes.

In another instance, lipofection can be used by mixing genetic material with lipid reagents and then subsequently injected into the brain to mediate transfect of the local cells.

Various embodiments involve the use of various control elements. In addition to genetic control elements, other control elements (particularly promoters and enhancers whose activities are sensitive to chemical, magnetic stimulation, or infrared radiation) can be used to mediate temporally-controlled expression of the optogenetic probes. For example, a promoter whose transcriptional activity is subject to infrared radiation allows one to use focused radiation to fine tune the expression of optogenetic probes in a focal region at only the desired time.

According to one embodiment of the present invention, the invention may be used in animal models of DBS, for example in Parkinsonian rats, to identify the target cell types responsible for therapeutic effects (an area of intense debate and immense clinical importance). This knowledge alone may lead to the development of improved pharmacological and surgical strategies for treating human disease.

According to another embodiment of the present invention, genetically-defined cell types may be linked with complex systems-level behaviors, and may allow the elucidation of the precise contribution of different cell types in many different brain regions to high-level organismal functioning.

Other aspects and embodiments are directed to systems, methods, kits, compositions of matter and molecules for ion pumps or for controlling inhibitory currents in a cell (e.g., in vivo and in vitro environments). As described throughout this disclosure, including the claims, such systems, methods, kits, compositions of matter are realized in manners consistent herewith. For example, in one embodiment, the present invention is directed to an assembly or kit of parts, having a product containing an NpHR-based molecular variant and another opsin-based molecule (ChR2-based and or NpHR-based) as a combined preparation for use in the treatment of disease of a neurological or CNS disorder (as a category of disorder types or a specific disorder as exemplified herein), wherein at least the NpHR-based molecular variant is useful for expressing a light-activated NpHR-based molecule that responds to light by producing an inhibitory current to dissuade depolarization of a cell, and wherein a high expression of the molecule manifests a toxicity level that is less than about 75%.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For instance, such changes may include additional NPHR-based sequences other than those listed in the immediately following Appendix. Such modifications and changes do not depart from the true spirit and scope of the present invention, which is set forth in the following appended claims.

What is claimed is:

1. A method for optically controlling a neuron, the method comprising exposing the neuron to light, wherein the neuron is genetically modified with an isolated nucleic acid comprising a mammalian codon optimized nucleotide sequence that encodes a variant opsin polypeptide derived from *Natromonas pharaonis* (NpHR), wherein the variant NpHR polypeptide comprises a heterologous endoplasmic reticulum (ER) export signal comprising the amino acid sequence set forth in SEQ ID NO:16, wherein the variant NpHR polypeptide inhibits depolarization of a neuron in response to the light, and wherein the variant NpHR polypeptide exhibits reduced toxicity in the neuron compared to toxicity induced by wild-type NpHR.

2. The method of claim 1, wherein the variant NpHR polypeptide comprises a heterologous signal peptide.

3. The method of claim 2, wherein the heterologous signal peptide is a nicotinic acetylcholine receptor signal peptide.

4. The method of claim 3, wherein the heterologous signal peptide comprises the amino acid sequence set forth in SEQ ID NO:13.

5. The method of claim 1, wherein the nucleic acid is present in a recombinant expression vector.

6. The method of claim 5, wherein the nucleotide sequence is operably linked to a neuron-specific promoter.

7. The method of claim 6, wherein the neuron-specific promoter is a CaMKIIα promoter.

8. The method of claim 6, wherein the neuron-specific promoter is a cholinergic neuron-specific promoter.

9. The method of claim 5, wherein the expression vector is a viral expression vector.

10. The method of claim 9, wherein the viral expression vector is an adeno-associated viral vector or a lentivirus vector.

11. The method of claim 10, wherein the viral expression vector is a lentivirus vector.

12. The method of claim 1, wherein the variant NpHR polypeptide is encoded by nucleotides 1-873 of SEQ ID NO:1.

13. The method of claim 1, wherein the neuron is in a brain region selected from the group consisting of amygdala, accumbens, cortex, hippocampus, dopaminergic projection, serotonergic projection, and noradrenergic projection.

14. The method of claim 1, wherein the light has a wavelength of from 573 nm to 613 nm.

15. The method of claim 1, wherein the neuron is further genetically modified to express a channelrhodopsin-2 light-activated polypeptide.

* * * * *